United States Patent
Zhu et al.

(10) Patent No.: US 10,829,492 B2
(45) Date of Patent: Nov. 10, 2020

(54) AMINO PYRAZOLOPYRIMIDINE COMPOUND USED AS NEUROTROPHIC FACTOR TYROSINE KINASE RECEPTOR INHIBITOR

(71) Applicants: CHIA TAI TIANQING PHARMACEUTICAL GROUP CO., LTD., Lianyungang (CN); CENTAURUS BIOPHARMA CO., LTD., Beijing (CN); LIANYUNGANG RUNZHONG PHARMACEUTICAL CO., LTD., Lianyungang (CN)

(72) Inventors: Li Zhu, Beijing (CN); Yuandong Hu, Beijing (CN); Wei Wu, Beijing (CN); Liguang Dai, Beijing (CN); Xiaowei Duan, Beijing (CN); Yanqing Yang, Beijing (CN); Yinghui Sun, Beijing (CN); Yongxin Han, Beijing (CN); Yong Peng, Beijing (CN); Fansheng Kong, Beijing (CN); Hong Luo, Beijing (CN); Ling Yang, Lianyungang (CN); Hongjiang Xu, Lianyungang (CN); Meng Guo, Lianyungang (CN); Zhaobai Zhong, Lianyungang (CN); Shanchun Wang, Lianyungang (CN)

(73) Assignees: CHIA TAI TIANQING PHARMACEUTICAL GROUP CO., LTD., Jiangsu (CN); CENTAURUS BIOPHARMA CO., LTD., Beijing (CN); LIANYUNGANG RUNZHONG PHARMACEUTICAL CO., LTD., Lianyungang (CN)

( * ) Notice: Subject to any disclaimer, the term of this patent is extended or adjusted under 35 U.S.C. 154(b) by 0 days.

(21) Appl. No.: 16/345,679

(22) PCT Filed: Oct. 27, 2017

(86) PCT No.: PCT/CN2017/108100
§ 371 (c)(1),
(2) Date: Apr. 26, 2019

(87) PCT Pub. No.: WO2018/077246
PCT Pub. Date: May 3, 2018

(65) Prior Publication Data
US 2019/0352306 A1 Nov. 21, 2019

(30) Foreign Application Priority Data

Oct. 28, 2016 (CN) .......................... 2016 1 0970314
Jan. 21, 2017 (CN) .......................... 2017 1 0044000

(51) Int. Cl.
C07D 487/04 (2006.01)

(52) U.S. Cl.
CPC .................. *C07D 487/04* (2013.01)

(58) Field of Classification Search
CPC ........................... A61K 31/519; C07D 487/04
USPC ........................................ 514/259.1; 544/281
See application file for complete search history.

(56) References Cited

U.S. PATENT DOCUMENTS

2016/0000783 A1    1/2016  Takeuchi et al.

FOREIGN PATENT DOCUMENTS

| CN | 102056927 A | 5/2011 |
|---|---|---|
| CN | 102264736 A | 11/2011 |
| CN | 102596957 A | 7/2012 |
| CN | 104114553 A | 10/2014 |
| CN | 104650092 A | 5/2015 |
| CN | 104995172 A | 10/2015 |
| WO | 2009/140128 A2 | 11/2009 |
| WO | 2010/048314 A1 | 4/2010 |
| WO | 2011/006074 A1 | 1/2011 |
| WO | 2012/034095 A1 | 3/2012 |
| WO | 2013028263 A1 | 2/2013 |
| WO | 2013/088256 A1 | 6/2013 |
| WO | 2014143242 A1 | 9/2014 |
| WO | 2016/097869 A1 | 6/2016 |

OTHER PUBLICATIONS

International Search Report in PCT/CN2017/108100, dated Feb. 2, 2018.

*Primary Examiner* — Jeffrey H Murray
(74) *Attorney, Agent, or Firm* — Kilpatrick Townsend & Stockton LLP

(57) ABSTRACT

Provided is an amino pyrazolopyrimidine compound as represented by the following structural formula used as a neurotrophic factor tyrosine kinase receptor inhibitor. The compound can inhibit the activity of Trk kinase and can treat diseases mediated by a Trk tyrosine kinase receptor in mammals.

General formula I

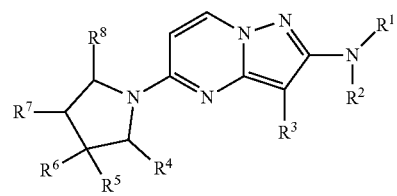

AA

20 Claims, No Drawings

AMINO PYRAZOLOPYRIMIDINE COMPOUND USED AS NEUROTROPHIC FACTOR TYROSINE KINASE RECEPTOR INHIBITOR

CROSS REFERENCE TO RELATED APPLICATION

The present application is a U.S. National Application of PCT/CN2017/108100, International Filing Date Oct. 27, 2017, which claims the priorities and benefits of the Chinese invention patent application Nos. 201610970314.3 and 201710044000.5 filed with the China National Intellectual Property Administration on Oct. 28, 2016 and Jan. 21, 2017, respectively, which are incorporated herein by reference in their entireties.

TECHNICAL FIELD

The present application relates to the field of medical chemistry, and more particularly, to an aminopyrazolopyrimidine compound, a process for preparing the same, a pharmaceutical composition comprising the compound, and a use thereof in the treatment of a disease mediated by Trk kinase.

BACKGROUND

NTRK/TRK (Tropomyosin receptor kinase) is a neurotrophic factor tyrosine kinase receptor, and belongs to a family of receptor tyrosine kinase. The Trk family mainly includes three members, namely, NTRK1/TrkA, NTRK2/TrkB and NTRK3/TrkC. An intact Trk kinase comprises three parts: an extracellular domain, a transmembrane domain, and an intracellular domain. The extracellular domain of Trk kinase binds to a corresponding ligand, and then can cause a change in the conformation of the kinase to form a dimer. The intracellular domain of Trk kinase undergoes autophosphorylation to activate its own kinase activity, which further activates downstream signal transduction pathways (such as MAPK, AKT, PKC, etc.) and produces corresponding biological functions; wherein NGF (nerve growth factor) binds to TrkA, BDNF (derived neurotrophic factor) binds to TrkB, and NT3 (neurotrophic factor 3) binds to TrkC.

Trk kinase plays an important physiological role in the development of nerves, including the growth and function maintenance of neuronal axons, the occurrence and development of memory and the protection of neurons from injury, and so on. Meanwhile, a large number of studies have shown that the activation of Trk signaling pathway is also strongly correlated with the occurrence and development of a tumor. Activated Trk signaling proteins are found in neuroblastoma, prostate cancer and breast cancer, etc. The discovery of various Trk fusion proteins in recent years has further demonstrated their biological function in promoting tumorigenesis. The earliest TPM3-TrkA fusion protein was found in colon cancer cells, with an incidence of about 1.5% in tested clinical patients. Afterwards, different types of Trk fusion proteins, such as CD74-NTRK1, MPRIP-NTRK1, QKI-NTRK2, ETV6-NTRK3, BTB1-NTRK3 and so on, were found in different types of clinical tumor patient samples, such as lung cancer, head and neck cancer, breast cancer, thyroid cancer, glioma, and so on. These different NTRK fusion proteins per se are in a highly activated state of kinase activity without the need to bind to a ligand, and thereby can continuously phosphorylate the downstream signaling pathways, induce cell proliferation, and promote the occurrence and development of a tumor. Therefore, in recent years, Trk fusion proteins have become an effective anti-cancer target and research hotspot. For example, WO2010048314, WO2012116217, WO2010033941 and so on disclose Trk kinase inhibitors having different core structures. In addition, a target mutation that occurs after continuous administration is an important cause of tumor resistance. Recently, there have been NTRK mutation cases in the clinic, such as mutations of NTRK1 G595R and G667C (Russo M et al. Cancer Discovery, 2016, 6(1), 36-44), and mutation of NTRK3 G623R (Drilon A. et al., Annals of Oncology 2016, 27(5), 920-926), and finding a new Trk kinase inhibitor is expected to address the issue of tumor drug resistance caused by NTRK mutation.

SUMMARY OF THE INVENTION

In an aspect, the present application provides a compound of Formula I or a pharmaceutically acceptable salt thereof,

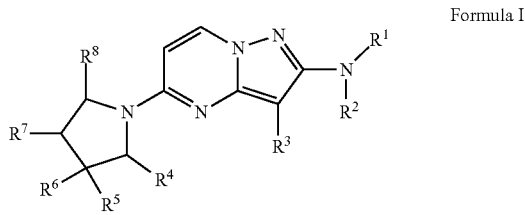

Formula I wherein, $R^1$ and $R^2$ are independently selected from the group consisting of hydrogen, $C_{1-10}$ alkyl, —C(=O)$R^9$, —C(=O)NH$R^9$ and —S(=O)$_2R^9$, wherein the $C_{1-10}$ alkyl is optionally substituted by one or more substituents independently selected from the group consisting of halo, nitro, hydroxy, cyano, $C_{1-6}$ alkyl, $C_{1-6}$ alkoxy, optionally substituted 3- to 6-membered cycloalkyl, optionally substituted 3- to 6-membered aliphatic heterocyclyl, optionally substituted 6- to 10-membered aryl and an optionally substituted 5- to 10-membered aromatic heterocyclyl;

$R^3$ is selected from the group consisting of hydrogen, halo, cyano, hydroxy, nitro, —C(=O)$R^{10}$, —C(=O)NR$^{10}$R$^{11}$, —C(=S)NR$^{10}$R$^{11}$, 6- to 10-membered aryl and 5- to 10-membered aromatic heterocyclyl, wherein the 6- to 10-membered aryl and 5- to 10-membered aromatic heterocyclyl are each independently optionally substituted by one or more substituents independently selected from the group consisting of $C_{1-6}$ alkyl, $C_{1-6}$ alkoxycarbonyl, optionally substituted pyrrolidinyl, optionally substituted morpholinyl and optionally substituted pyrrolidinylcarbonyl;

$R^4$ and $R^7$ are independently selected from the group consisting of hydrogen, halo, nitro, hydroxy, amino and cyano;

$R^5$ and $R^6$ are independently selected from the group consisting of hydrogen, halo, nitro, hydroxy, amino and cyano, or $R^5$ and $R^6$ together form oxo;

$R^8$ is selected from the group consisting of 5- to 10-membered aromatic heterocyclyl and 6- to 10-membered aryl, wherein the 5- to 10-membered aromatic heterocyclyl and the 6- to 10-membered aryl are each independently optionally substituted by one or more substituents independently selected from the group consisting of halo, nitro, oxygen, hydroxy, cyano, $C_{1-6}$ alkyl and $C_{1-6}$ alkoxy;

$R^9$ is selected from the group consisting of $C_{1-10}$ alkyl and phenyl, wherein the $C_{1-10}$ alkyl and phenyl are each independently optionally substituted by one or more substituents independently selected from the group consisting of halo, nitro, hydroxy, cyano, $C_{1-6}$ alkyl and $C_{1-6}$ alkoxy;

$R^{10}$ and $R^{11}$ are independently selected from the group consisting of hydrogen, hydroxy, $C_{1-6}$ alkyl, $C_{1-6}$ alkoxy, 3- to 6-membered cycloalkyl and 6- to 10-membered aryl, wherein the $C_{1-6}$ alkyl, $C_{1-6}$ alkoxy, 3- to 6-membered cycloalkyl and 6- to 10-membered aryl are each independently optionally substituted by one or more substituents independently selected from the group consisting of halo, hydroxy, nitro, cyano, $C_{1-4}$ alkyl, hydroxy($C_{1-6}$ alkyl), 2,2-dimethyl-1,3-dioxolan-4-yl and N,N-di($C_{1-4}$ alkyl)amino; or $R^{10}$ and $R^{11}$ taken together with the N to which they are attached form a 5- to 10-membered alicyclic heterocyclyl, wherein the 5- to 10-membered alicyclic heterocyclyl is optionally substituted by one or more substituents independently selected from the group consisting of halo, hydroxy, nitro and cyano.

In another aspect, the present application provides a pharmaceutical composition comprising the compound of Formula I, or a pharmaceutically acceptable salt thereof.

In a further aspect, the present application provides a method for treating a disease mediated by Trk tyrosine kinase receptor in a mammal, comprising administering to the mammal in need thereof a therapeutically effective amount of the compound of Formula I or a pharmaceutically acceptable salt thereof, or a pharmaceutical composition thereof.

In still another aspect, the present application provides a use of the compound of Formula I or a pharmaceutically acceptable salt thereof, or a pharmaceutical composition thereof in the preparation of a medicament for the prophylaxis or treatment of a disease mediated by Trk tyrosine kinase receptor.

In yet another aspect, the present application provides a use of the compound of Formula I or a pharmaceutically acceptable salt thereof, or a pharmaceutical composition thereof in the prophylaxis or treatment of a disease mediated by Trk tyrosine kinase receptor.

In a further aspect, the present application provides the compound of Formula I or a pharmaceutically acceptable salt thereof, or a pharmaceutical composition thereof for use in the prophylaxis or treatment of a disease mediated by Trk tyrosine kinase receptor.

DETAILED DESCRIPTION OF THE INVENTION

The following description includes specific details to provide a thorough understanding of various disclosed embodiments. However, the relevant person skilled in the art will recognize that, using other methods, components, materials and the like instead of one or more of these specific details disclosed herein can achieve the embodiments.

Throughout this specification the phrase "one embodiment" or "an embodiment" or "in another embodiment" or "in some embodiments" means at least one embodiment includes particular reference element, structure, or characteristic relevant to the embodiment. Thus, the phrase which appears in different locations throughout the specification, "in one embodiment" or "in an embodiment" or "in another embodiment" or "in some embodiments" is not necessarily all referring to the same embodiment. Furthermore, the particular element, structures, or characteristics may be optionally combined in any suitable manner in one or more embodiments.

It should be understood that the singular form of the articles "a" used in this specification and the appended claims (corresponding to the English "a", "an" and "the") includes plural object, unless the context clearly rules. Thus, for example, reaction including the "catalyst" mentioned includes a catalyst, or two or more catalysts. It should also be understood that the term "or" generally includes "and/or" meaning and then used, unless the context clearly defined.

In an aspect, the present application relates to a compound of Formula I, or a pharmaceutically acceptable salt thereof,

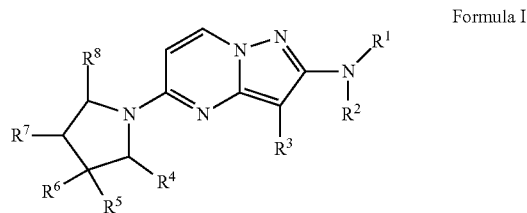

Formula I wherein, $R^1$ and $R^2$ are independently selected from the group consisting of hydrogen, $C_{1-10}$ alkyl, —C(=O)$R^9$, —C(=O)NHR$^9$ and —S(=O)$_2$R$^9$, wherein the $C_{1-10}$ alkyl is optionally substituted by one or more substituents independently selected from the group consisting of halo, nitro, hydroxy, cyano, $C_{1-6}$ alkyl, $C_{1-6}$ alkoxy, optionally substituted 3- to 6-membered cycloalkyl, optionally substituted 3- to 6-membered aliphatic heterocyclyl, optionally substituted 6- to 10-membered aryl and an optionally substituted 5- to 10-membered aromatic heterocyclyl;

$R^3$ is selected from the group consisting of hydrogen, halo, cyano, hydroxy, nitro, —C(=O)$R^{10}$, —C(=O)NR$^{10}$R$^{11}$, —C(=S)NR$^{10}$R$^{11}$, 6- to 10-membered aryl and 5- to 10-membered aromatic heterocyclyl, wherein the 6- to 10-membered aryl and 5- to 10-membered aromatic heterocyclyl are each independently optionally substituted by one or more substituents independently selected from the group consisting of $C_{1-6}$ alkyl, $C_{1-6}$ alkoxycarbonyl, optionally substituted pyrrolidinyl, optionally substituted morpholinyl and optionally substituted pyrrolidinylcarbonyl;

$R^4$ and $R^7$ are independently selected from the group consisting of hydrogen, halo, nitro, hydroxy, amino and cyano;

$R^5$ and $R^6$ are independently selected from the group consisting of hydrogen, halo, nitro, hydroxy, amino and cyano, or $R^5$ and $R^6$ together form oxo;

$R^8$ is selected from the group consisting of 5- to 10-membered aromatic heterocyclyl and 6- to 10-membered aryl, wherein the 5- to 10-membered aromatic heterocyclyl and the 6- to 10-membered aryl are each independently optionally substituted by one or more substituents independently selected from the group consisting of halo, nitro, oxygen, hydroxy, cyano, $C_{1-6}$ alkyl and $C_{1-6}$ alkoxy;

$R^9$ is selected from the group consisting of $C_{1-10}$ alkyl and phenyl, wherein the $C_{1-10}$ alkyl and phenyl are each independently optionally substituted by one or more substituents independently selected from the group consisting of halo, nitro, hydroxy, cyano, $C_{1-6}$ alkyl and $C_{1-6}$ alkoxy;

$R^{10}$ and $R^{11}$ are independently selected from the group consisting of hydrogen, hydroxy, $C_{1-6}$ alkyl, $C_{1-6}$ alkoxy, 3- to 6-membered cycloalkyl and 6- to 10-membered aryl, wherein the $C_{1-6}$ alkyl, $C_{1-6}$ alkoxy, 3- to 6-membered cycloalkyl and 6- to 10-membered aryl are each independently optionally substituted by one or more substituents independently selected from the group consisting of halo, hydroxy, nitro, cyano, $C_{1-4}$ alkyl, $C_{1-6}$ alkyl substituted by hydroxy, 2,2-dimethyl-1,3-dioxolan-4-yl and —N($C_{1-4}$ alkyl)$_2$;

or $R^{10}$ and $R^{11}$ taken together with the N to which they are attached form a 5- to 10-membered alicyclic heterocyclyl, wherein the 5- to 10-membered alicyclic heterocyclyl is optionally substituted by one or more substituents independently selected from the group consisting of halo, hydroxy, nitro and cyano.

In some embodiments of the present application, $R^8$ is selected from the group consisting of 5- to 10-membered aromatic heterocyclyl and 6- to 10-membered aryl, wherein the 5- to 10-membered aromatic heterocyclyl and the 6- to 10-membered aryl are each independently optionally substituted by one or more substituents independently selected from the group consisting of halo, nitro, hydroxy, cyano, $C_{1-6}$ alkyl and $C_{1-6}$ alkoxy;

In some embodiments of the present application, $R^1$ and $R^2$ are independently selected from the group consisting of hydrogen, $C_{1-6}$ alkyl, —C(=O)$R^9$, —C(=O)NH$R^9$ and —S(=O)$_2R^9$, wherein the $C_{1-6}$ alkyl is optionally substituted by one or more substituents independently selected from the group consisting of halo, nitro, hydroxy, cyano, $C_{1-4}$ alkyl, $C_{1-4}$ alkoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholinyl, thiomorpholinyl, tetrahydrothiophenyl, phenyl, 4-methylphenyl, 4-methoxyphenyl, furyl, pyrrolyl and pyrazinyl;

$R^3$ is selected from the group consisting of hydrogen, halo, cyano, hydroxy, nitro, —C(=O)$R^{10}$, —C(=O)N$R^{10}R^{11}$, —C(=S)N$R^{10}R^{11}$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of $C_{1-4}$ alkyl, $C_{1-4}$ alkoxycarbonyl, pyrrolidin-1-yl, 3-hydroxypyrrolidin-1-yl, morpholin-4-yl and 3-hydroxypyrrolidin-1-ylcarbonyl;

$R^4$ and $R^7$ are independently selected from the group consisting of hydrogen, fluoro, chloro, bromo, iodo, nitro, hydroxy, amino and cyano;

$R^5$ and $R^6$ are independently selected from the group consisting of hydrogen, fluoro, chloro, bromo, iodo, nitro, hydroxy, amino and cyano, or $R^5$ and $R^6$ together form oxo;

$R^8$ is selected from the group consisting of phenyl, furyl, pyrrolyl, thienyl, oxazolyl, isoxazolyl, thiazolyl, pyridyl, pyridonyl and pyrazinyl, wherein the phenyl, furyl, pyrrolyl, thienyl, oxazolyl, isoxazolyl, thiazolyl, pyridyl, pyridonyl and pyrazinyl are each independently optionally substituted by one or more substituents independently selected from the group consisting of halo, nitro, hydroxy, cyano, $C_{1-4}$ alkyl and $C_{1-4}$ alkoxy;

$R^9$ is selected from the group consisting of $C_{1-6}$ alkyl and phenyl, wherein the $C_{1-6}$ alkyl and phenyl are each independently optionally substituted by one or more substituents independently selected from the group consisting of halo, nitro, hydroxy, cyano, $C_{1-4}$ alkyl and $C_{1-4}$ alkoxy;

$R^{10}$ and $R^{11}$ are independently selected from the group consisting of hydrogen, hydroxy, methyl, ethyl, n-propyl, isopropyl, methoxy, ethoxy, n-propoxy, cyclopropyl, cyclobutyl, cyclopentyl, cyclohexyl and phenyl, wherein methyl, ethyl, n-propyl, isopropyl, methoxy, ethoxy, n-propoxy, cyclopropyl, cyclobutyl, cyclopentyl, cyclohexyl and phenyl are each independently optionally substituted by one or more substituents independently selected from the group consisting of halo, hydroxy, nitro, cyano, methyl, ethyl, n-propyl, isopropyl, hydroxymethyl, 2-hydroxyethyl, 3-hydroxy-n-propyl, 2,2-dimethyl-1,3-dioxolan-4-yl, N,N-dimethylamino and N,N-diethylamino;

or $R^{10}$ and $R^{11}$ taken together with the N to which they are attached form pyrrolidin-1-yl, wherein the pyrrolidin-1-yl is optionally substituted by one or more substituents independently selected from the group consisting of halo, and hydroxy.

In some embodiments of the present application, $R^1$ and $R^2$ are independently selected from the group consisting of hydrogen, methyl, ethyl, n-propyl, isopropyl, —C(=O)$R^9$, —C(=O)NH$R^9$ and —S(=O)$_2R^9$, wherein methyl, ethyl, n-propyl and isopropyl are each independently optionally substituted by one or more substituents independently selected from the group consisting of fluoro, chloro, bromo, iodo, nitro, hydroxy, cyano, methyl, ethyl, methoxy, ethoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholin-4-yl, thiomorpholin-4-yl, tetrahydrothiophenyl, phenyl, 4-methylphenyl, 4-methoxyphenyl, furanyl, pyrrolyl and pyrazinyl;

$R^3$ is selected from the group consisting of hydrogen, fluoro, chloro, bromo, iodo, cyano, hydroxy, nitro, —C(=O)$R^{10}$, —C(=O)N$R^{10}R^{11}$, C(=S)NH$_2$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of methyl, ethyl, n-propyl, isopropyl, methoxycarbonyl, ethoxycarbonyl, pyrrolidin-1-yl, 3-hydroxypyrrolidin-1-yl, morpholin-4-yl and 3-hydroxypyrrolidin-1-ylcarbonyl;

$R^4$ and $R^7$ are independently selected from the group consisting of hydrogen, fluoro, chloro, bromo, iodo, and hydroxy;

$R^5$ and $R^6$ are independently selected from the group consisting of hydrogen, fluoro, chloro, bromo, iodo, and hydroxy, or $R^5$ and $R^6$ together form oxo;

$R^8$ is selected from the group consisting of phenyl, pyridyl, pyridonyl and pyrazinyl, wherein the phenyl, pyridyl, pyridonyl and pyraziny are each independently optionally substituted by one or more substituents independently selected from the group consisting of fluoro, chloro, bromo, iodo, hydroxy, methoxy and ethoxy;

$R^9$ is selected from the group consisting of methyl, ethyl, n-propyl, isopropyl and phenyl, wherein the methyl, ethyl, n-propyl, isopropyl and phenyl are each independently optionally substituted by one or more substituents independently selected from the group consisting of fluoro, chloro, bromo, iodo, methyl, ethyl, methoxy and ethoxy;

$R^{10}$ and $R^{11}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, chloro, bromo, iodo, hydroxy, methyl, ethyl, hydroxymethyl, 2-hydroxyethyl, 2,2-dimethyl-1,3-dioxolan-4-yl, N,N-dimethylamino and N,N-diethylamino;

or $R^{10}$ and $R^{11}$ taken together with the N to which they are attached form pyrrolidin-1-yl, wherein the pyrrolidin-1-yl is optionally substituted by one or more substituents independently selected from the group consisting of fluoro, chloro, bromo, iodo, and hydroxy.

In some embodiments of the present application, $R^8$ is phenyl, wherein the phenyl is optionally substituted by one or more fluoro; preferably, $R^8$ is 2,5-difluorophenyl.

In some embodiments of the present application, $R^1$ and $R^2$ are independently selected from the group consisting of hydrogen, methyl, ethyl, —C(=O)$R^9$, —C(=O)NH$R^9$ and —S(=O)$_2R^9$, wherein the methyl and ethyl are each independently optionally substituted by one or more substituents independently selected from the group consisting of morpholin-4-yl and 4-methoxyphenyl;

$R^3$ is selected from the group consisting of hydrogen, bromo, cyano, —C(=O)$R^{10}$, —C(=O)N$R^{10}R^{11}$, C(=S)NH$_2$, phenyl, oxazolyl, thiazolyl and pyrazolyl, wherein the phenyl, oxazolyl, thiazolyl and pyrazolyl are each independently optionally substituted by one or more substituents independently selected from the group consisting of methyl, ethoxycarbonyl, morpholin-4-yl and 3-hydroxypyrrolidin-1-ylcarbonyl;

$R^5$ and $R^6$ are independently selected from the group consisting of hydrogen, fluoro and hydroxy, or $R^5$ and $R^6$ together form oxo;

$R^9$ is selected from the group consisting of methyl, ethyl and phenyl, wherein the phenyl is optionally substituted by one or more methyl;

$R^{10}$ and $R^{11}$ are independently selected from the group consisting of hydrogen, hydroxy, methyl, ethyl, methoxy, ethoxy, cyclopropyl, cyclohexyl and phenyl, wherein ethyl, methoxy, ethoxy, cyclopropyl, cyclohexyl and phenyl are each independently optionally substituted by one or more substituents independently selected from the group consisting of fluoro, hydroxy, methyl, hydroxymethyl, 2,2-dimethyl-1,3-dioxolan-4-yl and N,N-dimethylamino;

or $R^{10}$ and $R^{11}$ taken together with the N to which they are attached form pyrrolidin-1-yl, wherein the pyrrolidin-1-yl is optionally substituted by one or more hydroxy.

In some embodiments of the present application, the compound of Formula I has a structure represented by Formula II,

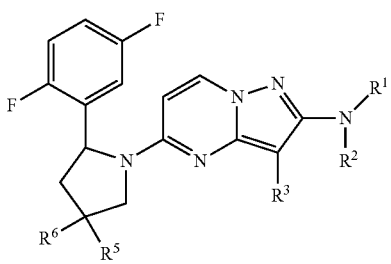

Formula II

Wherein $R^1$, $R^2$, $R^3$, $R^5$ and $R^6$ are as defined in the compound of Formula I.

In some embodiments of the present application, the compound of Formula II has a structure represented by Formula III,

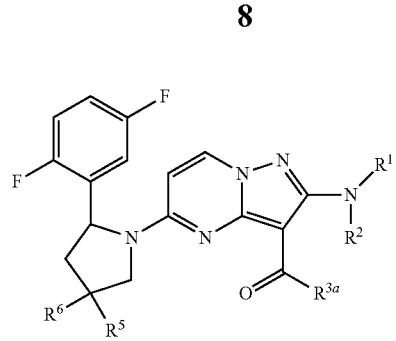

Formula III wherein, $R^1$, $R^2$, $R^5$ and $R^6$ are as defined in the compound of Formula II;

$R^{3a}$ is selected from the group consisting of $R^{7a}$ and N$R^{7a}R^{8a}$;

$R^{7a}$ and $R^{8a}$ are independently selected from the group consisting of hydrogen, hydroxy, $C_{1-6}$ alkyl, $C_{1-6}$ alkoxy, 3- to 6-membered cycloalkyl and 6- to 10-membered aryl, wherein the $C_{1-6}$ alkyl, $C_{1-6}$ alkoxy, 3- to 6-membered cycloalkyl and 6- to 10-membered aryl are each independently optionally substituted by one or more substituents independently selected from the group consisting of halo, hydroxy, nitro, cyano, $C_{1-4}$ alkyl, $C_{1-6}$ alkyl substituted by hydroxy, 2,2-dimethyl-1,3-dioxolan-4-yl and —N($C_{1-4}$ alkyl)$_2$;

or $R^{7a}$ and $R^{8a}$ taken together with the N to which they are attached form a 5- to 10-membered aliphatic heterocyclyl, wherein the 5- to 10-membered aliphatic heterocyclyl is optionally substituted by one or more substituents independently selected from the group consisting of halo, hydroxy, nitro and cyano.

In some embodiments, $R^{7a}$ and $R^{8a}$ are independently selected from the group consisting of hydrogen, hydroxy, methyl, ethyl, n-propyl, isopropyl, methoxy, ethoxy, n-propoxy, cyclopropyl, cyclobutyl, cyclopentyl, cyclohexyl and phenyl, wherein the methyl, ethyl, n-propyl, isopropyl, methoxy, ethoxy, n-propoxy, cyclopropyl, cyclobutyl, cyclopentyl, cyclohexyl and phenyl are each independently optionally substituted by one or more substituents independently selected from the group consisting of halo, hydroxy, nitro, cyano, methyl, ethyl, n-propyl, isopropyl, hydroxymethyl, 2-hydroxyethyl, 3-hydroxy-n-propyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more substituents independently selected from the group consisting of halo and hydroxy.

In some embodiments, $R^{7a}$ and $R^{8a}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, chloro, bromo, iodo, hydroxy, methyl, ethyl, hydroxymethyl, 2-hydroxyethyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more substituents independently selected from the group consisting of fluoro, chloro, bromo, iodo, and hydroxy.

In some embodiments, $R^1$ and $R^2$ are independently selected from the group consisting of hydrogen, methyl, ethyl, —C(=O)$R^{6a}$, —C(=O)NH$R^{6a}$, and —S(=O)$_2R^{6a}$, wherein the methyl and ethyl are each independently optionally substituted by one or more substituents independently selected from the group consisting of pyrrolidin-1-yl, piperidin-1-yl, piperidin-4-yl, morpholin-4-yl, thiomorpholin-4-yl, phenyl, 4-methylphenyl and 4-methoxyphenyl;

$R^{3a}$ is selected from the group consisting of $R^{7a}$ and $NR^{7a}R^{8a}$;

$R^5$ and $R^6$ are independently selected from the group consisting of hydrogen, fluoro and hydroxy, or $R^5$ and $R^6$ together form oxo;

$R^{6a}$ is selected from the group consisting of methyl, ethyl and 4-methylphenyl;

$R^{7a}$ and $R^{8a}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, hydroxy, methyl, hydroxymethyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more hydroxy.

In some embodiments of the present application, $R^{7a}$ and $R^{8a}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclohexyl and phenyl are each independently optionally substituted by one or more substituents independently selected from the group consisting of fluoro, hydroxy, methyl, hydroxymethyl, 2,2-dimethyl-1,3-dioxolan-4-yl, N,N-dimethyl amino and N,N-diethylamino.

In some embodiments of the present application, the compound of Formula III has a structure represented by Formula IIIa,

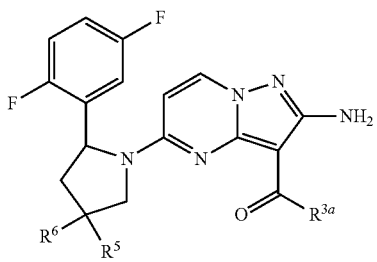

Formula IIIa wherein $R^{3a}$, $R^5$ and $R^6$ are as defined in the compound of Formula III.

In some embodiments of the present application, the compound of Formula II has a structure represented by Formula IV,

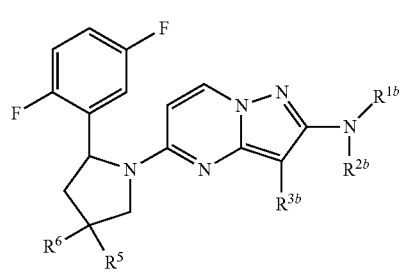

Formula IV wherein, $R^5$ and $R^6$ are as defined in the aforementioned compound of Formula II;

$R^{1b}$ and $R^{2b}$ are independently selected from the group consisting of hydrogen and $C_{1-10}$ alkyl, wherein the $C_{1-10}$ alkyl is optionally substituted by one or more substituents independently selected from the group consisting of halo, nitro, hydroxy, cyano, $C_{1-6}$ alkyl, $C_{1-6}$ alkoxy, optionally substituted 3- to 6-membered cycloalkyl, optionally substituted 3- to 6-membered alicyclic heterocyclyl, optionally substituted 6- to 10-membered aryl and optionally substituted 5- to 10-membered aromatic heterocyclyl;

$R^{3b}$ is selected from the group consisting of hydrogen, halo, cyano, hydroxy, nitro, —C(=S)NH$_2$, 6- to 10-membered aryl and 5- to 10-membered aromatic heterocyclyl, wherein the 6- to 10-membered aryl and 5- to 10-membered aromatic heterocyclyl are each independently optionally substituted by one or more substituents independently selected from the group consisting of $C_{1-6}$ alkyl, $C_{1-6}$ alkoxycarbonyl, optionally substituted pyrrolidinyl, optionally substituted morpholinyl and optionally substituted pyrrolidinylcarbonyl.

In some embodiments of the present application, $R^{1b}$ and $R^{2b}$ are independently selected from the group consisting of hydrogen and $C_{1-6}$ alkyl, wherein the $C_{1-6}$ alkyl is optionally substituted by one or more substituents independently selected from the group consisting of halo, nitro, hydroxy, cyano, $C_{1-4}$ alkyl, $C_{1-4}$ alkoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholinyl, thiomorpholinyl, tetrahydrothiophenyl, phenyl, 4-methylphenyl, 4-methoxyphenyl, furyl, pyrrolyl and pyrazinyl;

$R^{3b}$ is selected from the group consisting of hydrogen, halo, cyano, hydroxy, nitro, —C(=S)NH$_2$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of $C_{1-4}$ alkyl, $C_{1-4}$ alkoxycarbonyl, pyrrolidin-1-yl, 3-hydroxypyrrolidin-1-yl, morpholin-4-yl and 3-hydroxypyrrolidin-1-ylcarbonyl.

In some embodiments of the present application, $R^{1b}$ and $R^{2b}$ are independently selected from the group consisting of hydrogen, methyl and ethyl, wherein the methyl and ethyl are each independently optionally substituted by phenyl, 4-methylphenyl or 4-methoxyphenyl;

$R^{3b}$ is selected from the group consisting of hydrogen, fluoro, chloro, bromo, iodo, cyano, —C(=S)NH$_2$, phenyl,

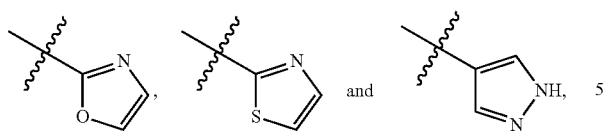

wherein the phenyl,

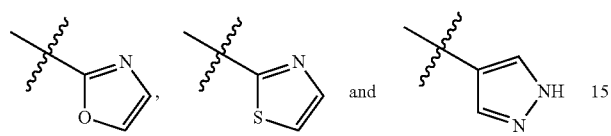

are each independently optionally substituted by one or more substituents independently selected from the group consisting of methyl, ethyl, methoxycarbonyl, ethoxycarbonyl, pyrrolidin-1-yl, morpholin-4-yl and 3-hydroxypyrrolidin-1-ylcarbonyl.

In some embodiments of the present application, the compound of Formula I or a pharmaceutically acceptable salt thereof according to the present application is selected from the following compounds:

1

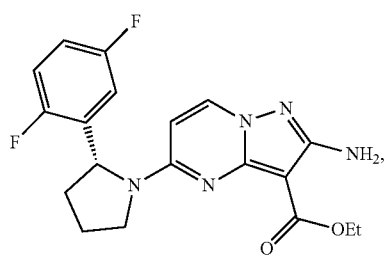

2

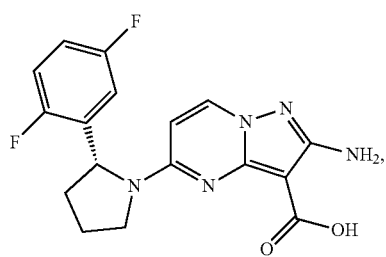

3

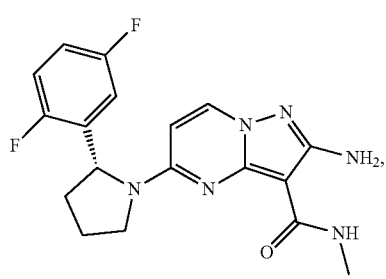

4

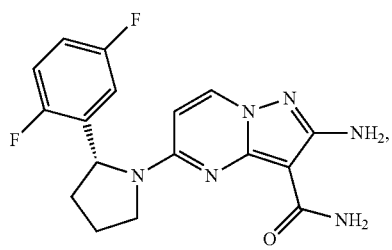

5

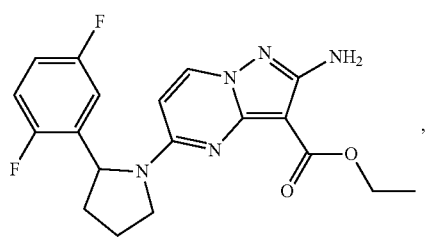

6

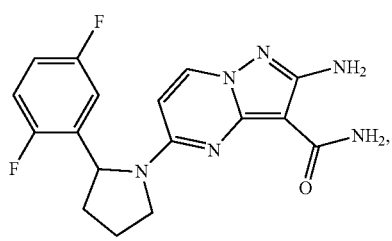

7

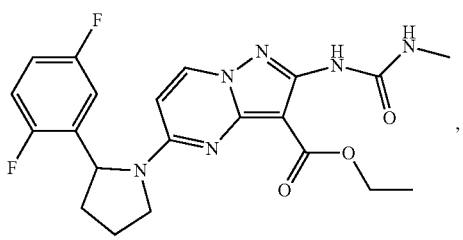

8

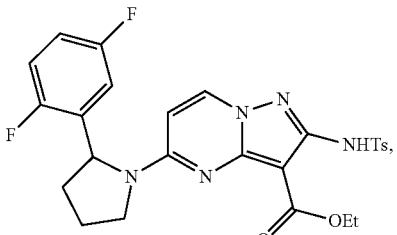

9

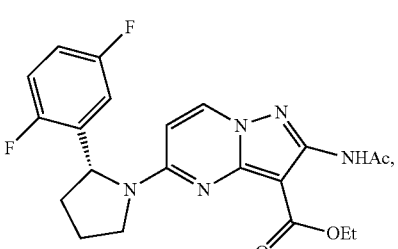

13
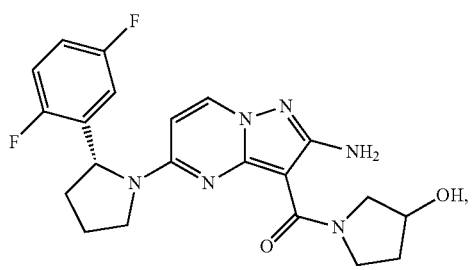
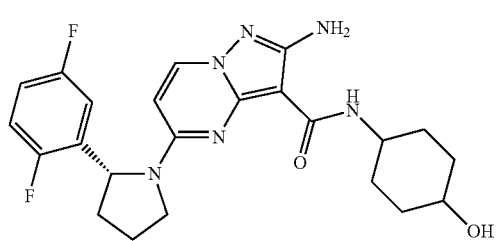
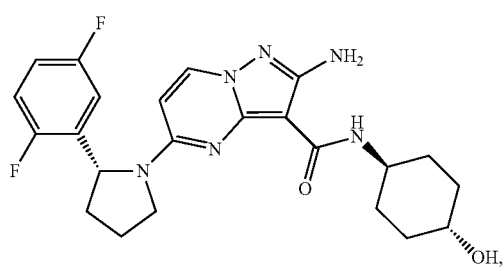
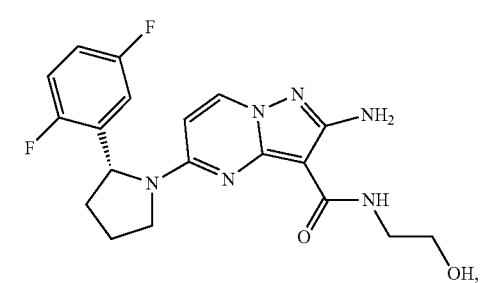
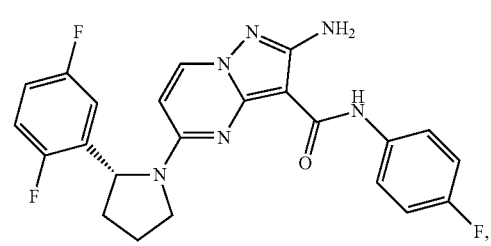
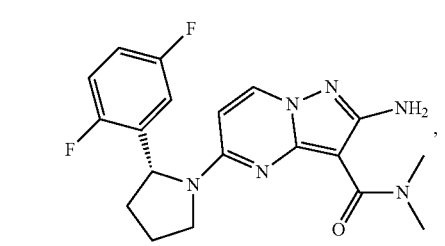
14
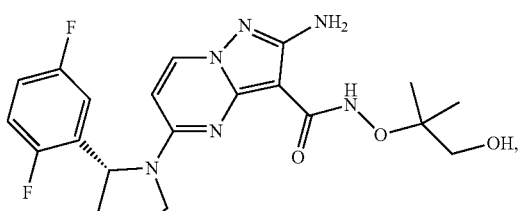
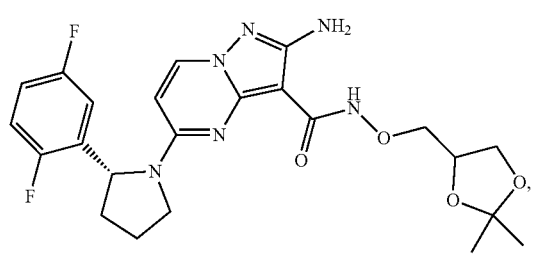
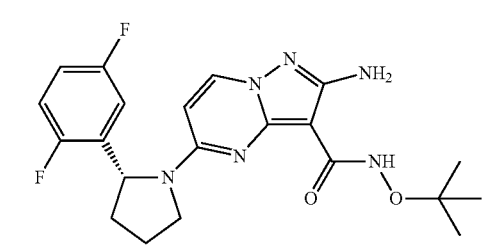
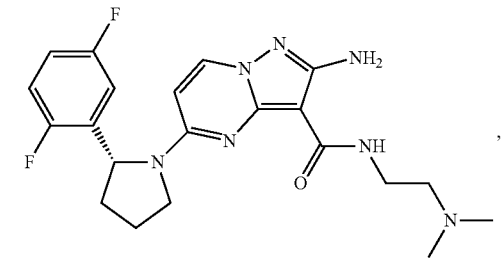
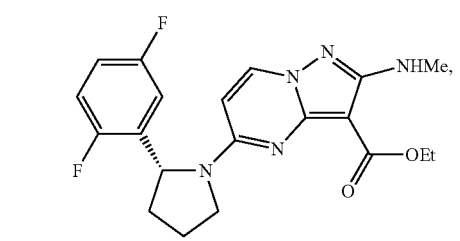
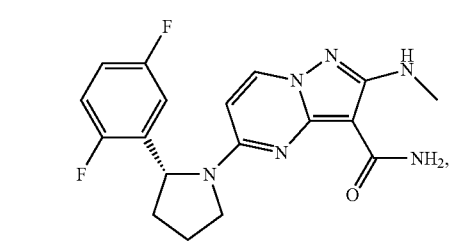

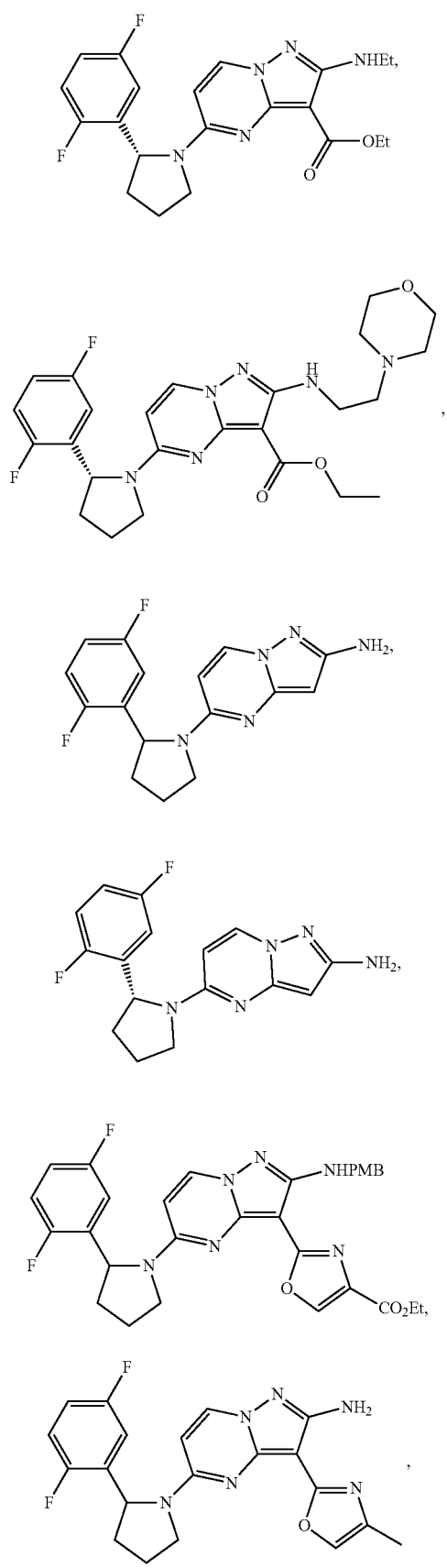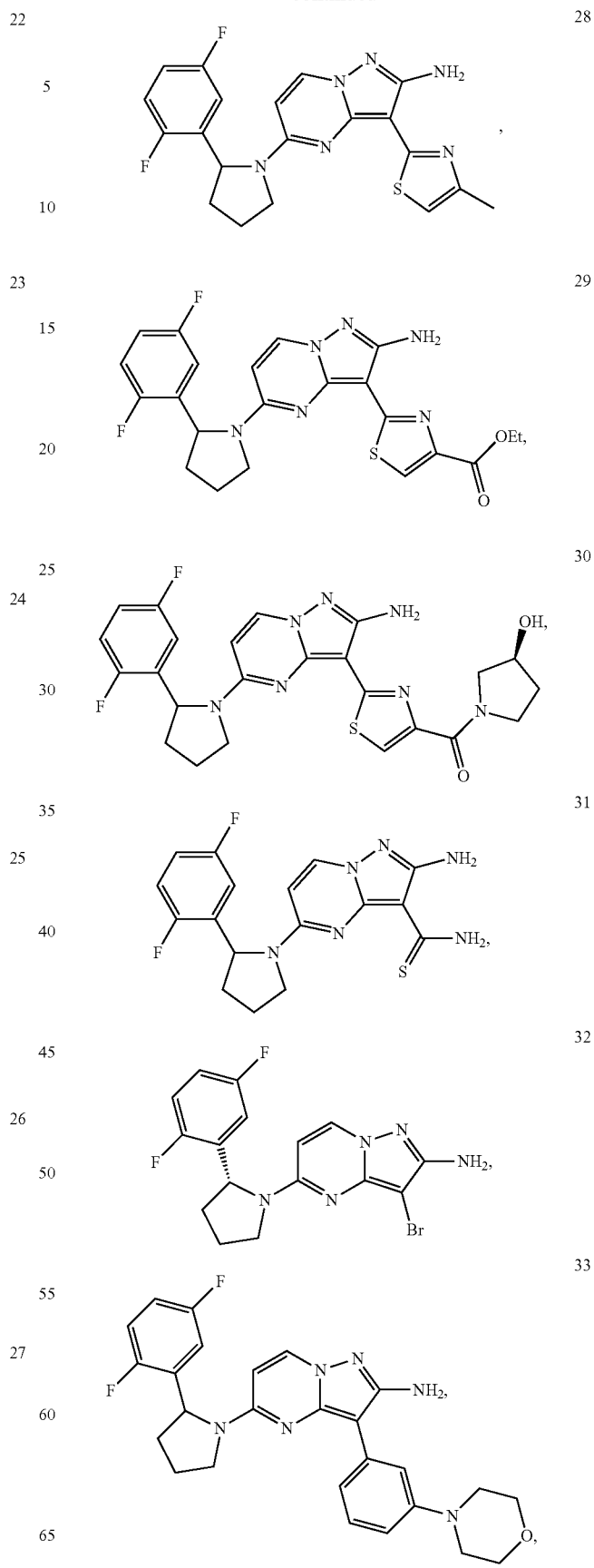

34
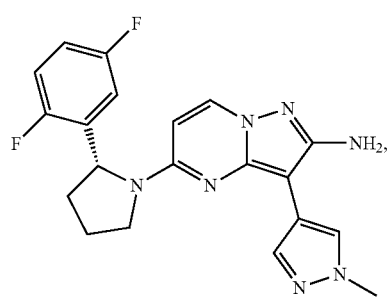
35
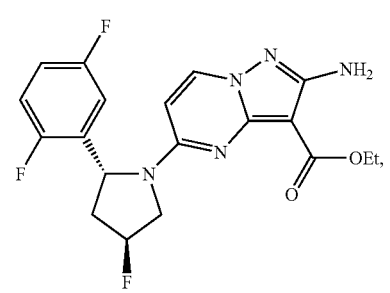
36
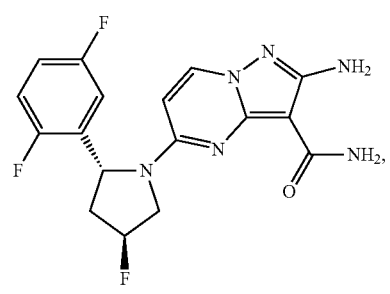
37
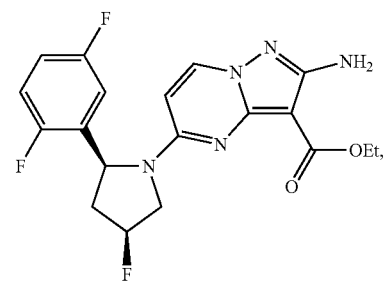
38
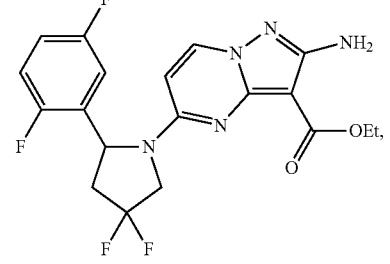
39
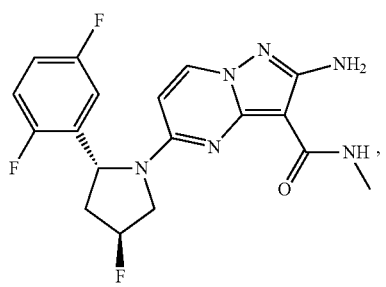
40
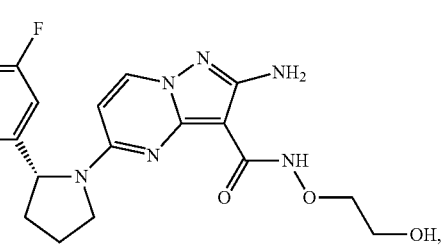
41
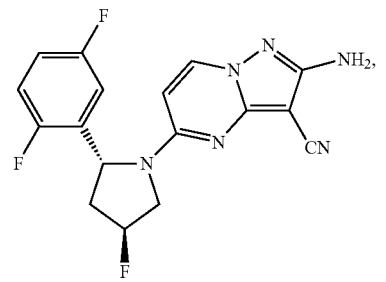
42
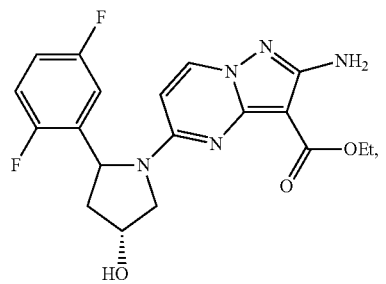
43
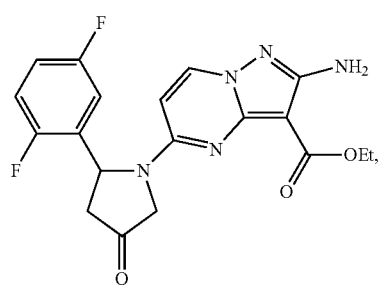

44

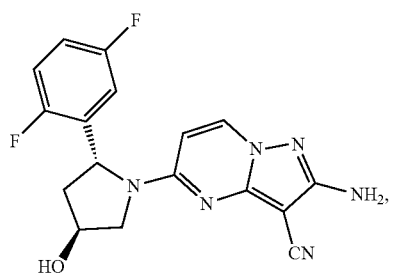

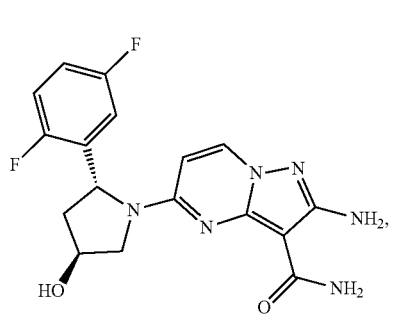

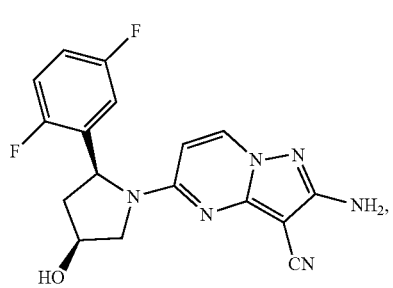

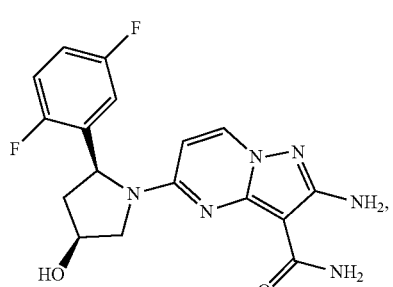

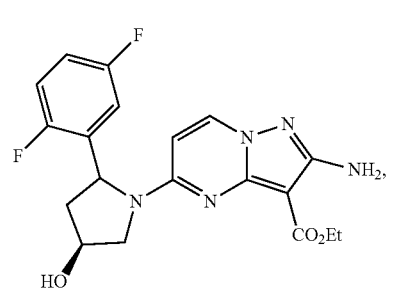

49

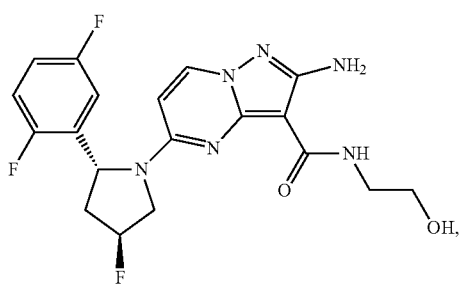

50

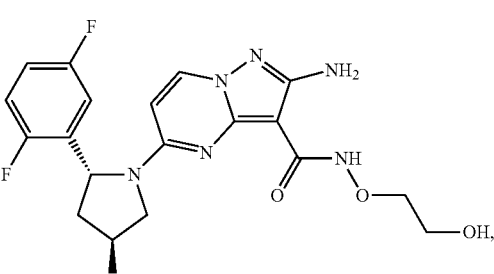

51

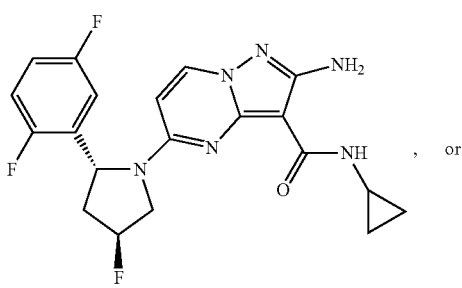

52

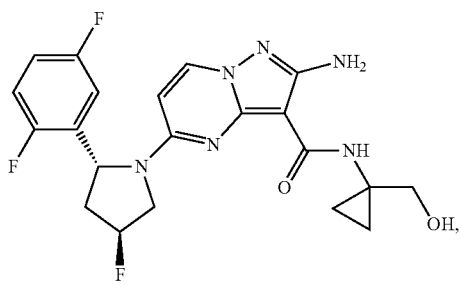

or a pharmaceutically acceptable salt thereof.

In another aspect, the present application relates to a pharmaceutical composition comprising the compound of Formula I or a pharmaceutically acceptable salt thereof according to the present application. In some embodiments, the pharmaceutical composition according to the present application further comprises pharmaceutically acceptable excipient(s).

The pharmaceutical composition according to the present application may be prepared by combining the compound according to the present application with appropriate pharmaceutically acceptable excipient(s). For example, the pharmaceutical compositions of the present application may be formulated into solid, semi-solid, liquid or gaseous formulations, such as tablets, pills, capsules, powders, granules, lozenges, ointments, emulsions, suspensions, solutions, syrups, pastes, suppositories, injections, inhalants, gels, microspheres, aerosols, and the like.

Typical administration routes of the compound according to the present application or a pharmaceutically acceptable salt thereof, or the pharmaceutical composition thereof include, but are not limited to, oral, rectal, topical, inhalation, parenteral, sublingual, intravaginal, intranasal, intraocular, intraperitoneal, intramuscular, subcutaneous, transdermal, and intravenous administration.

The pharmaceutical compositions of the present application can be prepared by using well-known methods in the art, such as conventional mixing method, dissolution method, granulation method, dragee manufacture method, grinding method, emulsification method, freeze-drying method, and the like.

In some embodiments of the present application, the pharmaceutical composition is in oral form. For oral administration, the pharmaceutical composition may be formulated by mixing the active compound(s) with pharmaceutically acceptable excipient(s) well-known in the art. Such excipients enable the compounds of the present application to be formulated into tablets, pills, lozenges, dragees, capsules, liquids, gels, syrups, emulsions, suspensions and the like, for oral administration to patients.

A solid oral pharmaceutical composition can be prepared by a conventional mixing, filling or tabletting method. For example, it can be obtained by mixing the active compound with a solid excipient, optionally grinding the resulting mixture, adding other suitable excipients, if necessary, and then processing the mixture into granules to obtain cores of tablets or dragees. Suitable excipients include, but are not limited to, binders, diluents, disintegrants, lubricants, glidants, sweeting agents, flavoring agents, and the like.

The pharmaceutical compositions of the present application can also be suitable for parenteral administration, such as sterile solutions, suspensions or lyophilized products in a suitable unit dosage form.

In a further aspect, the present application relates to a method for treating a disease mediated by Trk tyrosine kinase receptor in a mammal, comprising administering to the mammal in need thereof, preferably a human, a therapeutically effective amount of the compound of Formula I or a pharmaceutically acceptable salt thereof, or a pharmaceutical composition thereof.

In some embodiments, a daily administration dose of the compound of Formula I according to the present application in all the administration manners is from 0.01 mg/kg body weight to 300 mg/kg body weight, preferably from 10 mg/kg body weight to 300 mg/kg body weight, and more preferably from 25 mg/kg body weight to 200 mg/kg body weight, in the form of a single dose or a divided dose.

In another aspect, the present application relates to a use of the compound of Formula I or a pharmaceutically acceptable salt thereof, or a pharmaceutical composition thereof in the preparation of a medicament for the prophylaxis or treatment of a disease mediated by Trk tyrosine kinase receptor.

In a further aspect, the present application provides the compound of Formula I or a pharmaceutically acceptable salt thereof, or a pharmaceutical composition thereof for use in the prophylaxis or treatment of a disease mediated by Trk tyrosine kinase receptor.

Definition

Unless stated otherwise, the following terms used herein have the following meanings. A specific term shall not be considered unclear or indefinite when it is not specially defined. It should be understood according to its general meaning. A trade name used herein refers to a corresponding product or an active ingredient thereof.

The term "substituted" means that one or more hydrogen atoms on a given atom are replaced with a substituent, provided that the given atom has a normal valence state and the compound after substitution is stable. When the substituent is an oxo (i.e., =O), which means that two hydrogen atoms are replaced, the oxo substitution will not occur on an aromatic group.

The term "optional" or "optionally" means that the subsequently described event or circumstance may or may not occur, and that the description includes instances where said event or circumstance occurs and instances where said event or circumstance does not occurs. For example, ethyl group is "optionally" substituted with one or more fluorine or chlorine atoms, which means that ethyl group may be unsubstituted ($CH_2CH_3$), mono-substituted (such as $CH_2CH_2F$, $CHClCH_3$), multiple-substituted (such as $CHFCH_2F$, $CHClCHF_2$, $CH_2CHF_2$, and so on) or fully substituted ($CCl_2CF_3$, $CF_2CF_3$). A person skilled in the art will understand that in respect to any group containing one or more substituents, any substitution or substitution mode that is spatially impossible and/or not synthesizable will not be introduced.

The term "optionally substituted" as used herein means that a group can be optionally substituted by one or more substituents independently selected from the group consisting of alkyl, alkenyl, halo, haloalkyl, haloalkenyl, alkoxy, alkylthio, cyano, nitro, hydroxy, mercapto, —C(=S)OH, —C(=S)O-alkyl, —C(=S)—H, —C(=S)-alkyl, aryl, aryloxy, aralkyl, cycloalkyl, cycloalkyloxy, cycloalkylalkyl, cycloalkenyl, cycloalkenyloxy, cycloalkenylalkyl, aliphatic heterocyclyl, aliphatic heterocyclyloxy, aliphatic heterocyclylalkyl, aromatic heterocyclyl, aromatic heterocyclyloxy, aromatic heterocyclylalkyl, hydroxyamino, alkoxyamino, —OC(O)—$R^{14}$, —N($R^{14}$)$_2$, C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$) (wherein t is 1 or 2), —S(O)$_t$O$R^{16}$ (wherein t is 1 or 2), —S(O)$_t$$R^{16}$ (wherein t is 0, 1, or 2) and —S(O)$_t$N($R^{14}$)$^2$ (wherein t is 1 or 2), wherein each $R^{14}$ and each $R^{16}$ are independently hydrogen, alkyl, cycloalkyl, cycloalkenyl, aryl, arylalkyl, aliphatic heterocyclyl, aliphatic heterocyclylalkyl, aromatic heterocyclyl, or aromatic heterocyclylalkyl. Preferably, the substituents are independently selected from the group consisting of alkyl, halo and hydroxy.

The expression $C_{m-n}$ as used herein means that this moiety has an integer number of carbon atoms within a given range. For example, "$C_{1-6}$" means that this group may have 1 carbon atom, 2 carbon atoms, 3 carbon atoms, 4 carbon atoms, 5 carbon atoms or 6 carbon atoms.

When any variant (such as, R) occurs more than one times at the composition or structure of a compound, it is defined independently in each case. Therefore, for example, if a group is substituted with two Rs, then each R has an independent option.

The term "halogen" or "halo" refers to fluoro, chloro, bromo and iodo.

The term "hydroxy" refers to —OH group.

The term "cyano" refers to —CN group.

The term "amino" refers to —NH$_2$ group.

The term "nitro" refers to —NO$_2$ group.

The term "hydroxyalkyl" refers to —$C_nH_{2n}OH$. For example, hydroxymethyl refers to —CH$_2$OH and 2-hydroxyethyl refers to —CH$_2$CH$_2$OH.

The term "alkyl" refers to a hydrocarbyl group of Formula $C_nH_{2n+1}$. The alkyl group can be straight or branched. For example, the term "$C_{1-6}$ alkyl" refers to an alkyl group having 1 to 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) in an alkoxy group, a monoalkylamino group, a dialkylamino group, an alkylsulfonyl group, an alkoxycarbonyl group, and an alkylthio group has the same definition as defined above.

The term "alkoxy" refers to —O-alkyl.

The term "cycloalkyl" refers to an all-carbon ring that is fully saturated and can exist in the form of a monocyclic ring, bridged ring or spirocyclic ring. Unless otherwise indicated, the carbocycle is typically a 3- to 10-membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl etc.

The term "aliphatic heterocyclyl" refers to a fully saturated or partially unsaturated (but not fully unsaturated heteroaromatic) non-aromatic ring that can be exist in the form of a monocyclic ring, bicyclic ring or spirocyclic ring. Unless otherwise indicated, the aliphatic heterocyclic ring is typically a 3- to 6-membered ring containing 1 to 3 heteroatoms (preferably 1 or 2 heteroatoms) independently selected from sulfur, oxygen, and/or nitrogen. Non-limiting examples of aliphatic heterocyclyl include, but are not limited to oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl, etc.

The term "aryl" refers to a group of an all-carbon monocyclic or fused polycyclic aromatic ring having a conjugated π-electron system. For example, an aryl may have 6 to 20, 6 to 14, or 6 to 12 carbon atoms. Aryl may have at least one aromatic ring, and non-limiting examples thereof include, but are not limited to, phenyl, naphthyl, anthryl and 1,2,3,4-tetrahydronaphthalene, etc.

The term "aromatic heterocyclyl" refers to a monocyclic or fused polycyclic system containing at least one ring atom selected from N, O, and S with remaining ring atoms being C, and having at least one aromatic ring. Preferred aromatic heterocyclyl has a single 4- to 8-membered ring, especially single 5- to 8-membered ring, or has a fused polycyclic ring containing 6 to 14, especially 6 to 10 rings atoms. Non-limiting examples of aromatic heterocyclyl include, but are not limited to, pyrrolyl, furyl, thienyl, thiazolyl imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

The term "treatment" or "treating" refers to the administration of the compounds or preparations of the present application for preventing, ameliorating or eliminating diseases or one or more symptoms associated with the diseases, comprising:

(i) prophylaxis of occurrence of diseases or conditions in mammals, particularly when the mammals are susceptible to the conditions, but have not been diagnosed with them;

(ii) inhibition of diseases or conditions, i.e. restraining their development; or (iii) relief of diseases or conditions, i.e. recovering from the diseases or conditions.

The term "therapeutically effective amount" means an amount of a compound of the present application that (i) treats or prevents a particular disease, condition, or disorder, (ii) attenuates, ameliorates, or eliminates one or more symptoms of a particular disease, condition, or disorder, or (iii) prevents or retards the onset of one or more symptoms of a particular disease, condition, or disorder as described herein.

The amount of the compounds of the present application constituting so-called "therapeutically effective amount" depends on the compound, disease condition and severity thereof, the way of administration and age of the mammal to be treated, but can be routinely determined by those skilled in the art on the basis of their knowledge and the disclosure herein.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The term "pharmaceutically acceptable salt" includes, but is not limited to, an acid addition salt formed from the compound of Formula I and an inorganic acid, an acid addition salt formed from the compound of Formula I and an organic acid, or an addition salt formed from the compound of Formula I and an acidic amino acid, etc. The term "pharmaceutical composition" refers to a mixture of one or more compounds of the present application or pharmaceutically acceptable salts thereof and a pharmaceutically acceptable excipient. The purpose of pharmaceutical composition is to facilitate the administration of the compounds of the present application to the organism.

The term "pharmaceutical acceptable excipient" refers to those excipients which do not cause significant stimulation to an organism, and will not impair the bioactivity and properties of an active compound. Suitable excipients are well known to those skilled in the art, such as carbohydrates, waxes, water-soluble and/or water-swellable polymers, hydrophilic or hydrophobic materials, gelatin, oils, solvents, water, and the like.

The phrase "comprise" and English variations thereof, such as "comprises" and "comprising", should be construed in an open and inclusive sense, that is as, "including, but not limited to" Unless indicated otherwise, the abbreviations used herein have the following meanings.

Min refers to minute;
h refers to hour;
DCM refers to dichloromethane;
THF refers to tetrahydrofuran;
DMF refers to N,N-dimethylformamide;
DMSO refers to dimethylsulphoxide;
MeOH refers to methanol;
$H_2O$ refers to water;
PE refers to petroleum ether;
EA refers to ethyl acetate;
$Ti(OEt)_4$ refers to tetraethyl titanate;
DMAP refers to 4-dimethylaminopyridine;
TFA refers to trifluoroacetic acid;
TBDMSCl refers to tert-butyldimethylchlorosilane;
$NaBH_4$ refers to sodium borohydride;
NaHMDS refers to sodium hexamethyldisilazide;
$(BOC)_2O$ refers to di-tert-butyl dicarbonate;
NBS refers to N-bromosuccinimide;
Lawson's reagent refers to 2,4-bis(4-methoxyphenyl)-1,3-dithia-2,4-diphosphetane-2,4-disulfide;
DBU refers to 1,8-diazabicyclo[5.4.0]undec-7-ene;
DAST refers to diethylaminosulfur trifluoride;
HATU refers to O-(7-azabenzotriazol-1-yl)-N,N,N',N'-tetramethyluronium hexafluorophosphate;
DIEA refers to N,N-diisopropylethylamine;
DME refers to dimethyl ether;
TLC refers to thin layer chromatography;

M refers to molar concentration unit mol/L, for example, 2M refers to 2 mol/L;

N refers to an equivalent concentration, for example, 1N HCl refers to hydrochloric acid with a concentration of 1 mol/L; 2N NaOH refers to sodium hydroxide with a concentration of 2 mol/L;

Ts refers to p-methylbenzenesulfonyl;

TsCl refers to p-toluenesulfonyl chloride;

Et refers to ethyl;

Me refers to methyl;

Ac refers to acetyl;

PMB refers to p-methoxybenzyl;

TB S refers to tert-butyldimethylsilyl.

The intermediates and compounds according to the present application may also exist in the form of different tautomers, and all such forms are included in the scope of the present application. The term "tautomer" or "tautomeric form" refers to structural isomers with different energies which are interconvertible via a low energy barrier. For example, proton tautomers (also known as prototropic tautomers) include interconversions via migration of a proton, such as keto-enol and imine-enamine isomerizations. A specific example of proton tautomers is an imidazole moiety, in which a proton can migrate between the two ring nitrogen atoms. Valence tautomers include interconversions by reorganization of some of the bonding electrons. Exemplary enol tautomers are shown in the below, but are not limited thereto.

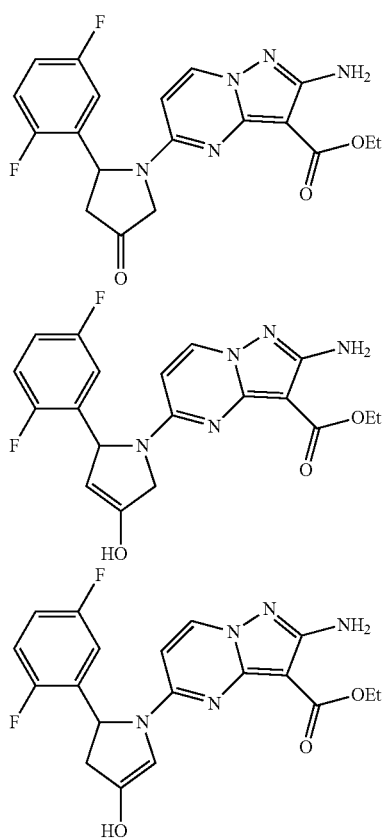

The compounds of the present application also include isotopically-labeled compounds of the present application which are identical to those recited herein in structure, but for the fact that one or more atoms are replaced by an atom having an atomic mass or mass number different from the atomic mass or mass number usually found in nature. Examples of isotopes that can be incorporated into the compounds of the present application include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present application (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Positron emitting isotopes such as $^{15}O$, $^{13}N$, $^{11}C$, and $^{18}F$ are useful for positron emission tomography (PET) studies to examine substrate occupancy. Isotopically labeled compounds of the present application can generally be prepared by following procedures analogous to those disclosed in the Schemes and/or Examples herein below, by substituting an isotopically labeled reagent for a non-isotopically labeled reagent.

Further, substitution with heavier isotopes (such as deuterium, i.e. $^2H$) may afford certain therapeutic advantages resulting from greater metabolic stability, for example, increasing in vivo half-life or reducing dosage requirements, and hence may be preferred in some circumstances, in which the deuteration may be partial or complete, and partial deuteration means that at least one hydrogen is replaced with at least one deuterium. Exemplary deuterated compounds are shown in the below, but are not limited thereto.

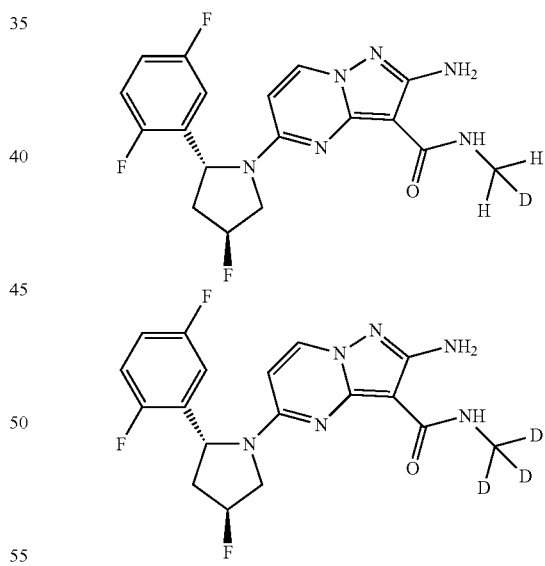

The compounds of the present application may be asymmetric, for example, having one or more stereoisomers. Unless otherwise indicated, all stereoisomers, such as enantiomers and diastereomers, are included therein. Compounds containing asymmetric carbon atom(s) of the present application can be isolated in an optically active pure form or a racemic form. The optically active pure form can be resolved from a racemic mixture, or synthesized by using chiral raw material(s) or chiral reagent(s). Non-limiting examples of stereoisomers include, but are not limited to:

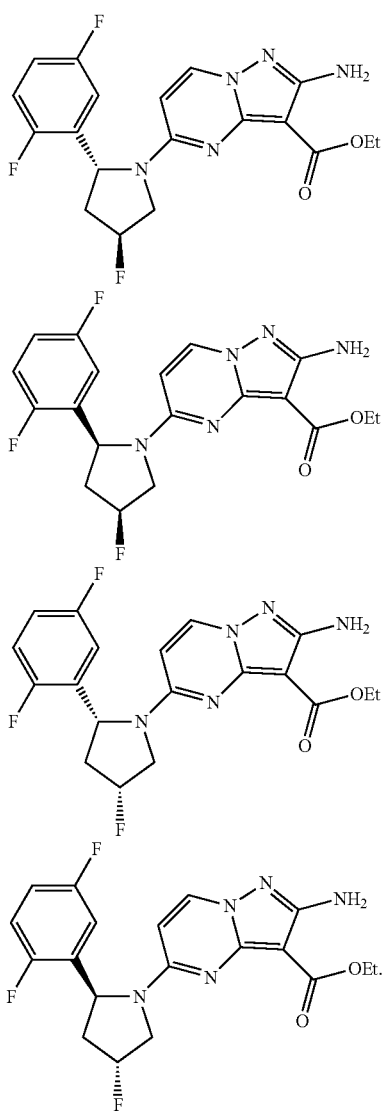

The compounds of the present application can be prepared through various synthetic methods well-known to a person skilled in the art, including specific embodiments illustrated below, embodiments formed by a combination of such specific embodiments with other chemical synthetic methods, and equivalents well-known to a person skilled in the art. Preferable embodiments include, but are not limited to, the working Examples in the present application.

A chemical reaction in the specific embodiments of the present application is carried out in an appropriate solvent which should be suitable for the chemical change(s) and required reagent(s) and material(s) in the present application. In order to obtain the compounds of the present application, a person skilled in the art sometimes needs to make a modification or selection to synthesis step(s) or reaction procedure(s) on the basis of the existing embodiments.

An important consideration in the design of a synthetic route in the art is the selection of a suitable protecting group for a reactive functional group, such as an amino group in the present application. For example, reference may be made to Greene's Protective Groups in Organic Synthesis (4th Ed). Hoboken, N.J.: John Wiley & Sons, Inc. All references cited herein are incorporated herein in their entireties.

In some embodiments, the compound of Formula III of the present application may be prepared by a person skilled in the field of organic synthesis using a standard method through general Scheme 1:

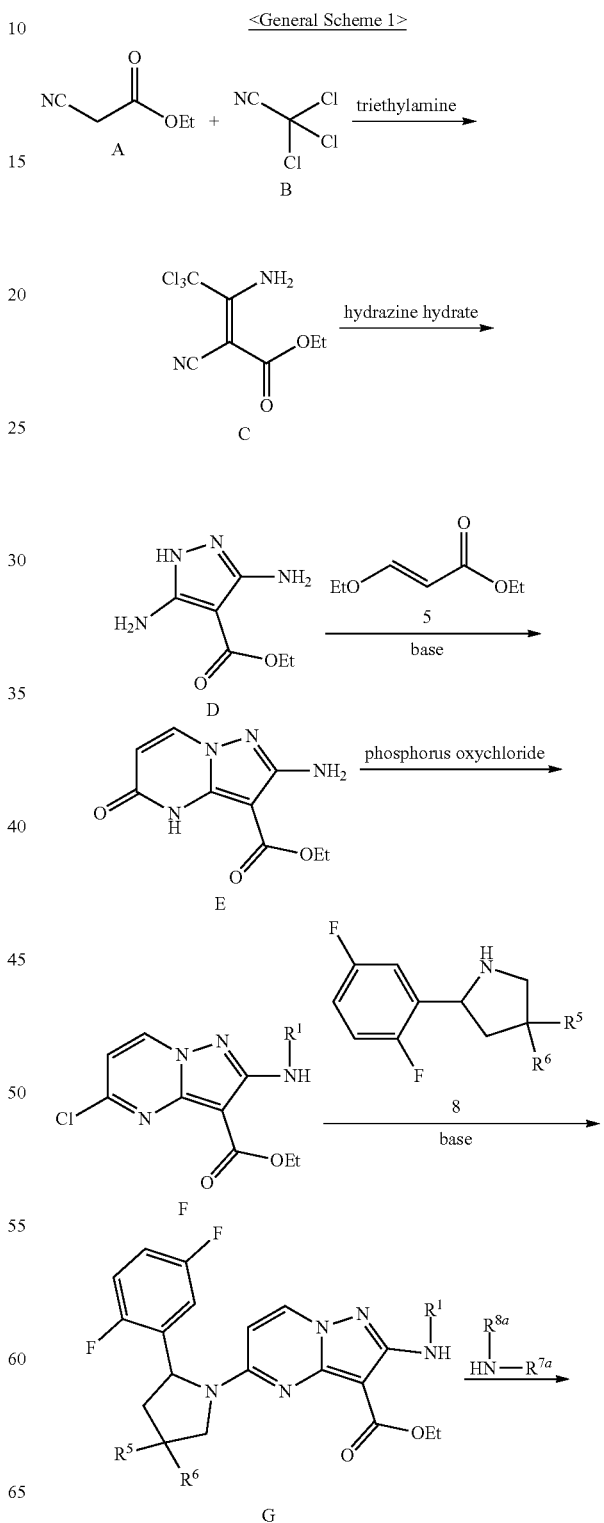

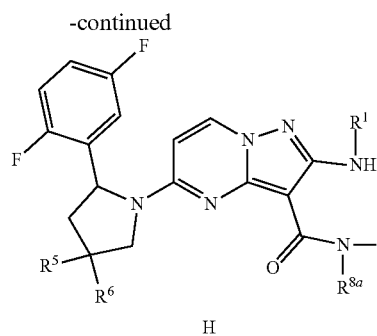

H wherein $R^1$ is hydrogen or acetyl; and $R^5$, $R^6$, $R^{7a}$ and $R^{8a}$ are as defined in the compound of Formula III.

In some embodiments, the compound of Formula III of the present application may be prepared by a person skilled in the field of organic synthesis using a standard method through general Scheme 2:

<General Scheme 2>

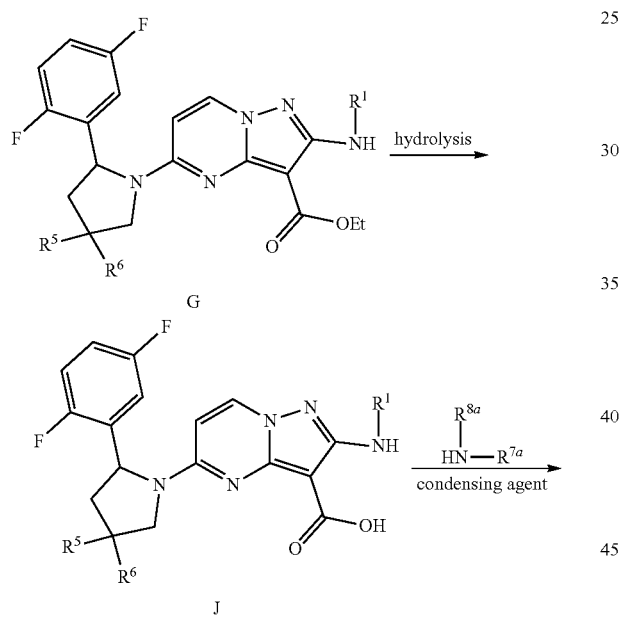

wherein $R^1$ is hydrogen or acetyl; and $R^5$, $R^6$, $R^{7a}$ and $R^{8a}$ are as defined in the compound of Formula III.

In some embodiments, the compound of Formula III of the present application may be prepared by a person skilled in the field of organic synthesis using a standard method through general Scheme 3:

<General Scheme 3>

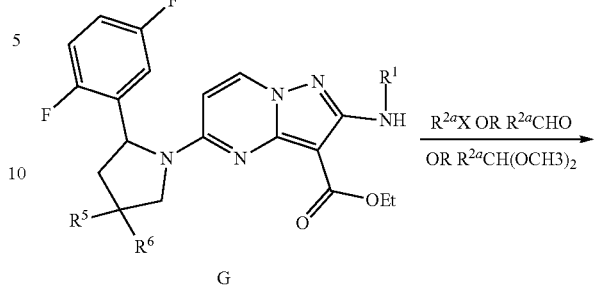

wherein X is halo, for example, including fluoro, chloro, bromo, and iodo; $R^1$ is hydrogen or acetyl; and $R^2$, $R^5$, $R^6$, $R^{7a}$ and $R^{8a}$ are as defined in the compound of Formula III.

In some embodiments, the compound of Formula IV of the present application may be prepared by a person skilled in the field of organic synthesis using a standard method through general Scheme 4:

<General Scheme 4>

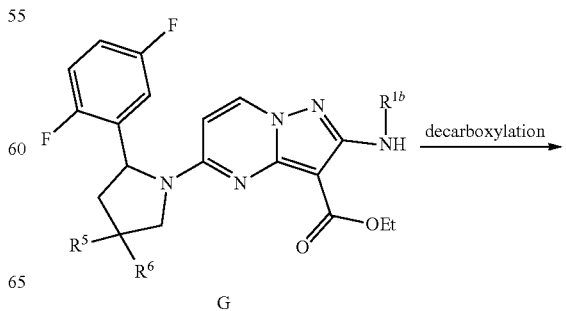

G

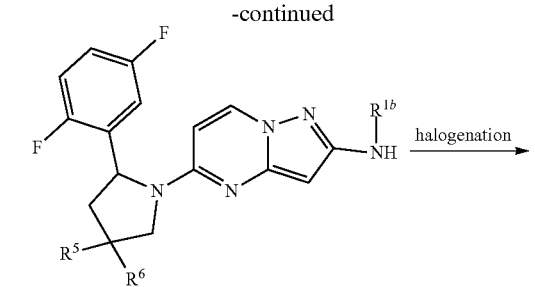

M

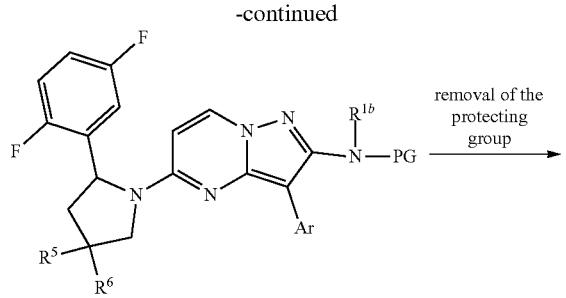

P

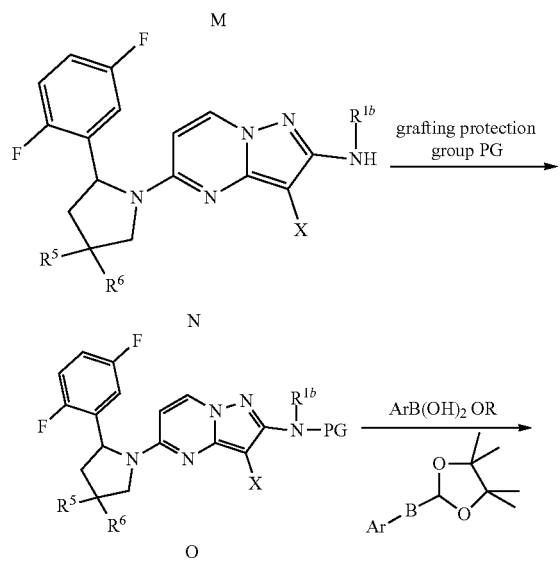

N

O

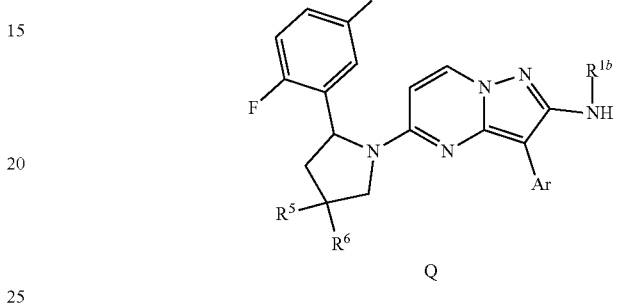

Q wherein X is a halo, for example, including fluoro, chloro, bromo, and iodo; $R^{1b}$ is hydrogen or acetyl; and $R^5$ and $R^6$ are as defined in the compound of Formula IV.

In some embodiments, the compound of Formula IV of the present application may be prepared by a person skilled in the field of organic synthesis using a standard method through general Scheme 5:

<General Scheme 5>

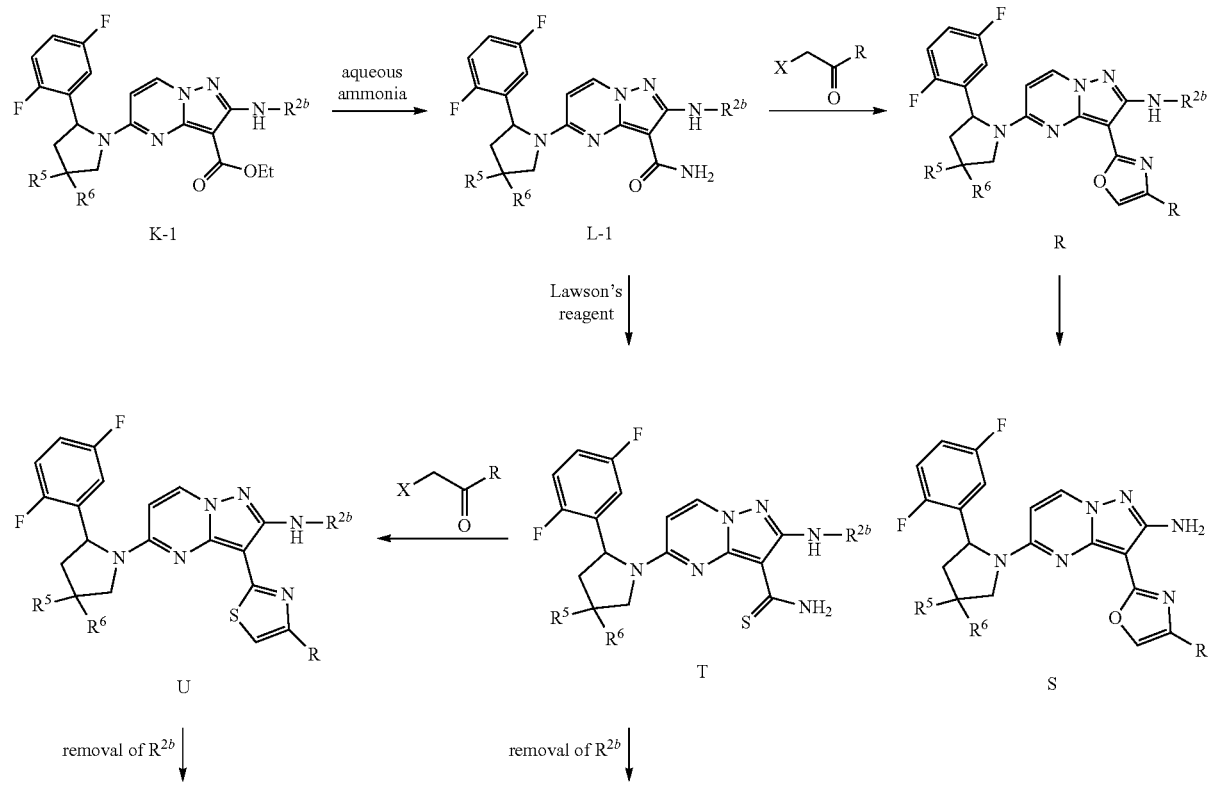

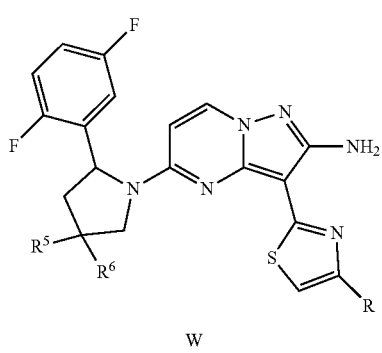

W

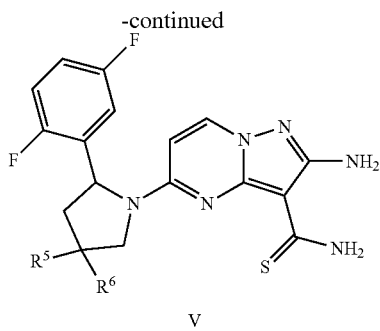

V wherein X is a halo, for example, including fluoro, chloro, bromo, and iodo; $R^{2b}$, $R^5$, and $R^6$ are as defined in the compound of Formula IV; and the compound of Formula K-1 can be prepared with reference to the method for preparing a compound of Formula K.

For clarity, the present invention is further illustrated by the following examples, but the examples are not intended to limit the scope of the present application. All reagents used in the present application are commercially available and can be used without further purification.

EXAMPLE

Preparation of Intermediates

Preparation Example 1
(R)-2-(2,5-difluorophenyl)pyrrolidine (Compound I1)

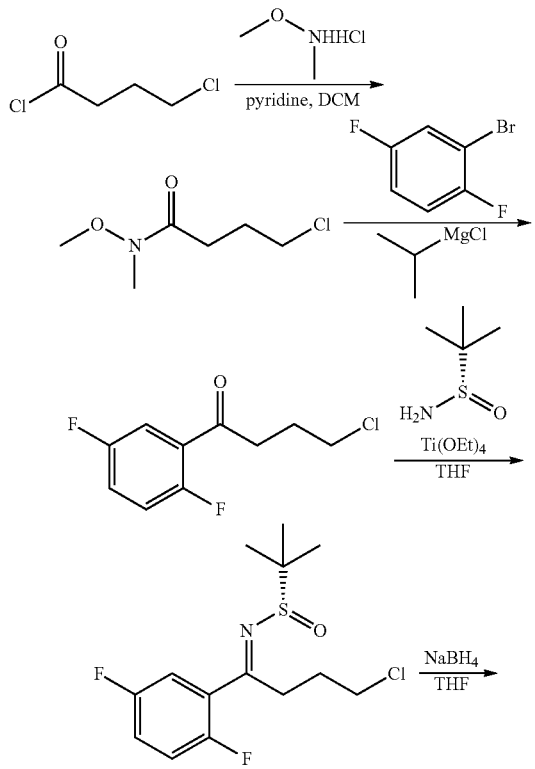

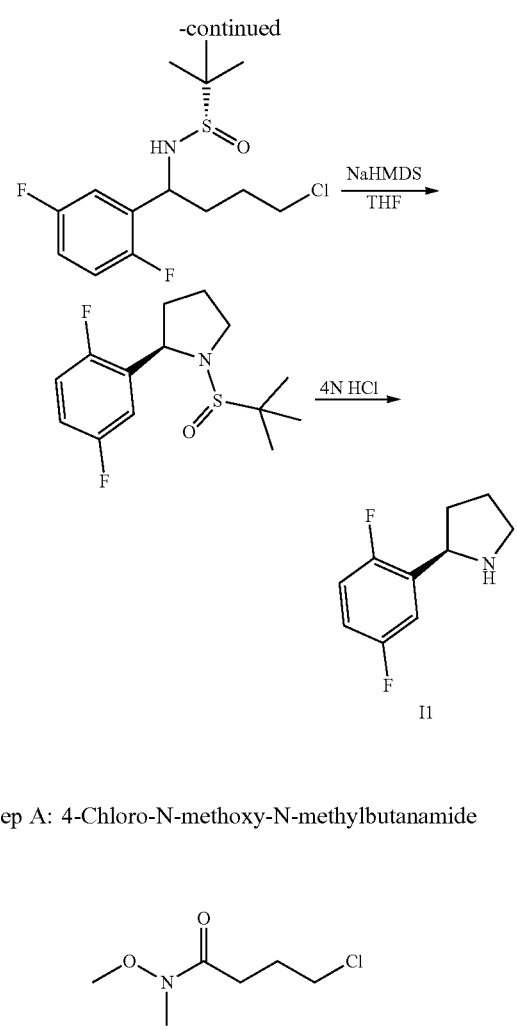

Step A: 4-Chloro-N-methoxy-N-methylbutanamide

To a solution of N,O-dimethylhydroxyamine hydrochloride (69.1 g) in DCM (200 mL) was added pyridine (150 mL) and stirred at 0° C. for 15 min, and then to the resulting mixture was added 4-chlorobutyryl chloride (100 g) and continuously stirred at 0° C. for 2 h. The reaction mixture was diluted with DCM, and the organic phase was washed with water and then a saturated saline solution. The organic phase was separated, dried over anhydrous sodium sulfate and filtered, and the filtrate was concentrated under reduced pressure to afford a crude product of the title compound (125.1 g), which was used in a next step without purification.

Step B: 4-Chloro-1-(2,5-difluorophenyl)butan-1-one

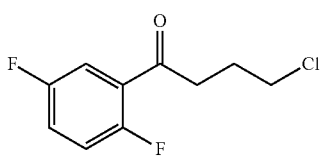 [SMILES: O=C(CCCCl)c1cc(F)ccc1F]

A solution of isopropylmagnesium chloride in THF (2M, 604 mL) was added dropwise to a solution of 2-bromo-1,4-difluorobenzene (244.7 g) in THF (1 L) that had been cooled to −50° C. After completion of the dropwise addition, the temperature was warmed to 0° C. while stirring for 1 h. The reaction mixture was cooled to −50° C. again. To the reaction mixture was added a solution of 4-chloro-N-methoxy-N-methylbutyramide (100 g) in THF (200 mL) dropwise under stirring, and gradually warmed to 30° C. and then continuously stirred at 30° C. for 3 h. The reaction mixture was quenched with a saturated aqueous ammonium chloride solution and extracted with ethyl acetate. The collected organic phase was washed with water and then a saturated saline solution. The organic layer was separated, dried over anhydrous sodium sulfate, and filtered. The filtrate was concentrated under reduced pressure, and the residue was purified by silica gel column chromatography to afford the title compound (101 g).

$^1$H NMR (400 MHz, CDCl$_3$) δ 7.59-7.55 (m, 1H), 7.26-7.20 (m, 1H), 7.17-7.11 (m, 1H), 3.68-3.65 (m, 2H), 3.20-3.16 (m, 2H), 2.25-2.19 (m, 2H). m/z=219[M+1]$^+$.

Step C: (S,E)-N-(4-chloro-1-(2,5-difluorophenyl)butylene)-2-methylpropane-2-sulfinamide

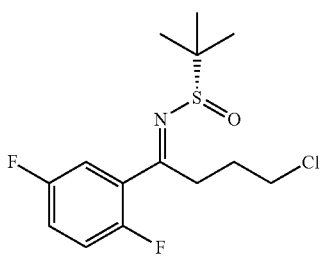 [SMILES: CC(C)(C)[S@](=O)/N=C(\CCCCl)c1cc(F)ccc1F]

To a solution of 4-chloro-1-(2,5-difluorophenyl)butan-1-one (155.4 g) and (S)-2-methylpropane-2-sulfinamide (129.2 g) in THF (1.0 L) was added tetraethyl titanate (243.2 g) under stirring. The mixture was stirred at 70° C. for an additional 16 h. The reaction mixture was then cooled to room temperature, quenched with a saturated aqueous ammonium chloride solution, diluted with ethyl acetate and filtered. The filtrate was washed with water and then a saturated saline solution. The organic layer was separated, dried over anhydrous sodium sulfate, and filtered. The filtrate was concentrated under reduced pressure, and the residue was purified by silica gel column chromatography to afford the title compound (207 g).

$^1$H NMR (400 MHz, CDCl$_3$) δ 7.38-6.90 (m, 3H), 3.66-3.58 (m, 2H), 3.44-3.22 (m, 1H), 3.0-2.80 (m, 1H), 2.25-2.01 (m, 2H), 1.30 (s, 9H). m/z=322 [M+1]$^+$.

Step D: (S)—N-(4-chloro-1-(2,5-difluorophenyl)butyl)-2-methylpropane-2-sulfinamide

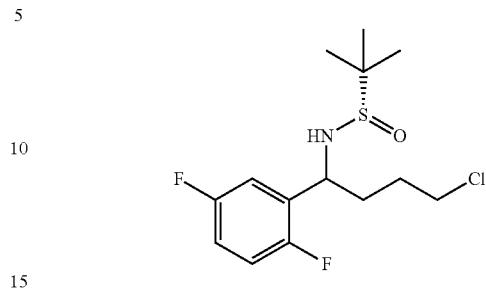

To a solution of (S,E)-N-(4-chloro-1-(2,5-difluorophenyl)butyl ene)-2-methylpropane-2-sulfenamide (177.5 g) in THF (1.5 L) was slowly added NaBH$_4$ (18.78 g) in portions at −65° C., meanwhile maintaining the temperature of the reaction system not exceeding −60° C. during the addition. After completion of the addition, the resulting mixture was stirred at −60° C. for 30 min and slowly warmed to −40° C. TLC revealed the disappearance of the starting materials. The reaction solution was slowly poured into ice water and quenched, and then extracted with ethyl acetate to afford a crude product of the title compound (173.2 g), which was used in a next step without purification.

Step E: (R)-1-((S)-tert-butylsulfinyl)-2-(2,5-difluorophenyl)pyrrolidine and (S)-1-((S)-tert-butyl sulfinyl)-2-(2,5-difluorophenyl)pyrrolidine

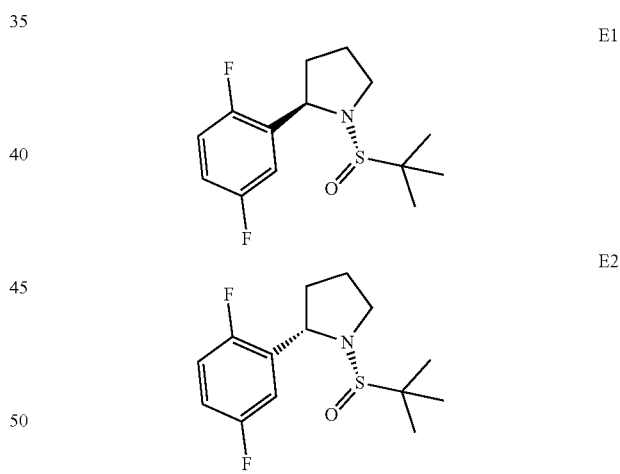

To a solution of (S)—N-(4-chloro-1-(2,5-difluorophenyl)butyl)-2-methylpropane-2-sulfenamide (193.2 g) in THF (1.8 L) was slowly added a solution of NaHMDS (2 M) in THF (343 mL) dropwise at −78° C., meanwhile maintaining the temperature of the reaction system not exceeding −75° C. during the addition. After completion of the addition, the resulting mixture was stirred at −60° C. for 30 min, slowly warmed to room temperature and stirred at room temperature for 1 h. TLC revealed the disappearance of the starting materials. The reaction solution was quenched with a saturated aqueous ammonium chloride solution, extracted with ethyl acetate, dried over anhydrous sodium sulfate, and then filtered. The filtrate was concentrated under reduced pressure, and the residue was purified by silica gel column chromatography to afford (R)-1-((S)-tert-butylsulfinyl)-2-(2,5-difluorophenyl)pyrrolidine (100 g) and (S)-1-((S)-tert-butyl sulfinyl)-2-(2,5-difluorophenyl)pyrrolidine (59 g).

E1: ¹H NMR (400 MHz, CDCl₃) δ 7.06-6.88 (m, 3H), 4.96 (d, J=7.2 Hz, 1H), 3.93-3.87 (m, 1H), 3.01-2.95 (m, 1H), 2.30-2.24 (m, 1H), 1.97-1.71 (m, 3H), 1.16 (s, 9H). m/z=288 [M+1]⁺.

E2: ¹H NMR (400 MHz, CDCl₃) δ 7.04-6.87 (m, 3H), 5.32 (d, J=7.2 Hz, 1H), 3.67-3.55 (m, 2H), 2.20-2.16 (m, 1H), 1.94-1.89 (m, 1H), 1.82-1.74 (m, 2H), 1.10 (s, 9H). m/z=288 [M+1]⁺.

Step F: (R)-2-(2,5-difluorophenyl)pyrrolidine

I1

4M HCl solution in 1,4-dioxane (27 mL) was slowly added to a solid of (R)-1-((S)-tert-butylsulfinyl)-2-(2,5-difluorophenyl)pyrrolidine (5.2 g) dropwise at −10° C., warmed to room temperature and stirred for 1 h. The reaction mixture was concentrated under reduced pressure, made basic with NaOH solution, and then extracted with ethyl acetate. The organic phrase was dried over anhydrous sodium sulfate, and filtered. The filtrate was concentrated under reduced pressure to afford the title compound (3.3 g).

¹H NMR (400 MHz, CDCl₃) δ 7.31-7.26 (m, 1H), 6.99-6.93 (m, 1H), 6.91-6.85 (m, 1H), 4.46 (t, J=7.6 Hz, 1H), 4.20-3.60 (m, 1H), 3.27-3.21 (m, 1H), 3.15-3.10 (m, 1H), 2.31-2.25 (m, 1H), 2.05-1.85 (m, 2H), 1.75-1.67 (m, 1H). m/z=184[M+1]⁺.

Preparation Example 2
2-(2,5-difluorophenyl)pyrrolidine (Compound I2)

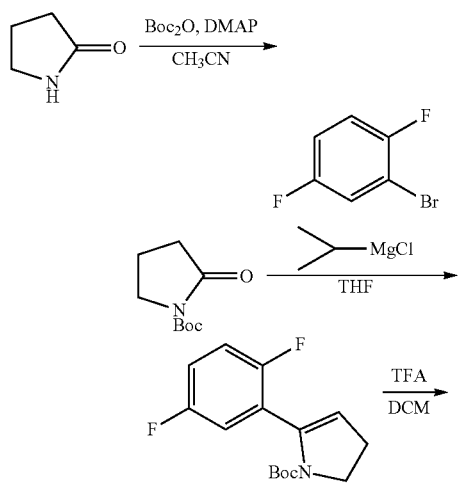

I2

Step A: tert-butyl 2-oxopyrrolidine-1-carboxylate

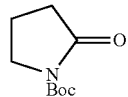

To a solution of 2-pyrrolidone (100 g) and DMAP (72 g) in acetonitrile (1.0 L) was added di-tert-butyl dicarbonate (308 g) at 0~5° C., and stirred at 20~35° C. for 2 h. The reaction mixture was concentrated under reduced pressure, and the resulting residue was diluted with ethyl acetate and then washed with water. The organic phase was dried over anhydrous sodium sulfate, and filtered. The filtrate was concentrated under reduced pressure, and the residue was purified and separated by silica gel column chromatography to afford tert-butyl 2-oxopyrrolidine-1-carboxylate (215.5 g).

¹H NMR (400 MHz, CDCl₃) δ 3.75 (t, J=7.2 Hz, 2H), 2.52 (t, J=8.0 Hz, 2H), 2.00 (dd, J=15.2 Hz, J=7.2 Hz, 2H), 1.53 (s, 9H).

Step B: tert-butyl 5-(2,5-difluorophenyl)-2,3-dihydro-1H-pyrrole-1-carboxylate

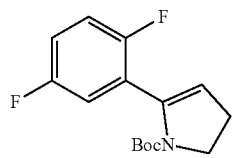 [SMILES: CC(C)(C)OC(=O)N1CCC=C1c1cc(F)ccc1F]

To a solution of 2-bromo-1,4-difluorobenzene (186 g) in THF (1.0 L) was added 2.0M isopropylmagnesium chloride solution in THF (482 mL) at −40° C., and continuously stirred at 5° C. for 1 h. To the above reaction mixture was added a solution of tert-butyl 2-oxopyrrolidine-1-carboxylate (215.5 g) in THF (250 mL) dropwise, and continuously stirred at 10° C. for 2 h. The reaction mixture was quenched with a saturated aqueous ammonium chloride solution and extracted with ethyl acetate. The organic phase was dried over anhydrous sodium sulfate and filtered, and the filtrate was concentrated under reduced pressure to afford a crude product of the title compound (323.4 g), which was used in a next step without purification.

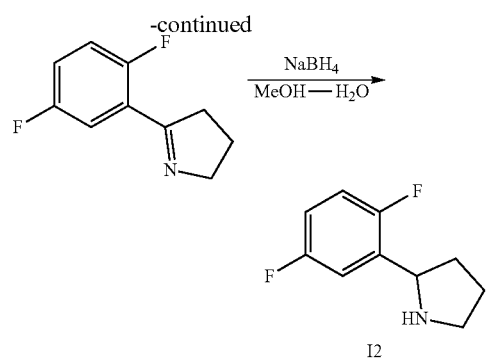

Step C:
5-(2,5-difluorophenyl)-3,4-dihydro-2H-pyrrole

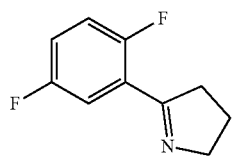 [SMILES: Fc1ccc(F)c(C2=NCCC2)c1]

To a solution of tert-butyl 5-(2,5-difluorophenyl)-2,3-dihydro-1H-pyrrole-1-carboxylate (318.4 g) in DCM (1.0 L) was added TFA (421 mL) at −40° C. and stirred at 20-35° C. for 2 h. The reaction mixture was concentrated under reduced pressure, and the resulting residue was diluted with ethyl acetate and then washed with a saturated sodium bicarbonate solution. The organic phase was dried over anhydrous sodium sulfate and filtered, and the filtrate was concentrated under reduced pressure to afford a crude product of the title compound (224.4 g), which was used in a next step without purification.

$^1$H NMR (400 MHz, CDCl$_3$) δ 7.68-7.64 (m, 1H), 7.08-7.04 (m, 2H), 4.04-3.99 (m, 2H), 3.02-2.97 (m, 2H), 2.08-2.00 (m, 2H). m/z=182[M+1]$^+$.

Step D: 2-(2,5-difluorophenyl)pyrrolidine

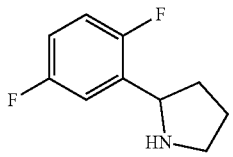

I2

To a solution of 5-(2,5-difluorophenyl)-3,4-dihydro-2H-pyrrole (224.4 g) in a mixture of MeOH/H$_2$O(V/V=4/1, 2.0 L) was added NaBH$_4$ (93.82 g), and stirred at 20~35° C. for 2 h. The reaction mixture was quenched with a 1N aqueous HCl solution, and basified with a 2N aqueous NaOH solution, then extracted with DCM, dried over anhydrous sodium sulfate. The filtrate was concentrated under reduced pressure to afford the title compound (171.3 g).

$^1$H NMR (400 MHz, CDCl$_3$) δ 7.28-7.19 (m, 1H), 6.97-6.91 (m, 1H), 6.87-6.82 (m, 1H), 4.39 (t, J=7.5 Hz, 1H), 3.18-3.12 (m, 1H), 3.04 (dd, J=14.8 Hz, J=8.0 Hz, 1H), 2.31-2.19 (m, 1H), 2.01-1.75 (m, 3H), 1.65-1.58 (m, 1H). m/z=184[M+1]$^+$.

Preparation Example 3 (2R,4S)-2-(2,5-difluorophenyl)-4-fluoropyrrolidine (Compound I3) and (2S,4S)-2-(2,5-difluorophenyl)-4-fluoropyrrolidine (Compound I4)

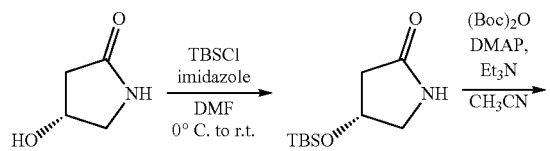

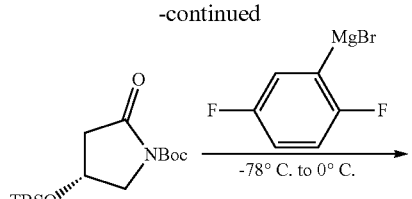

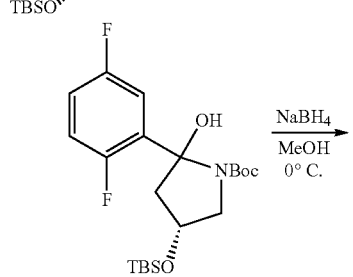

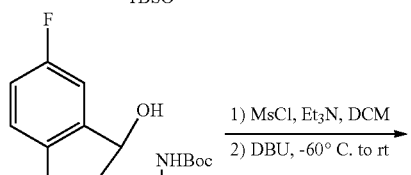

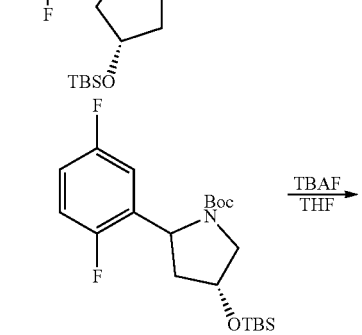

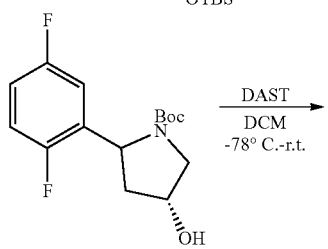

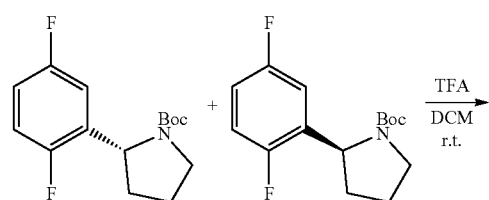

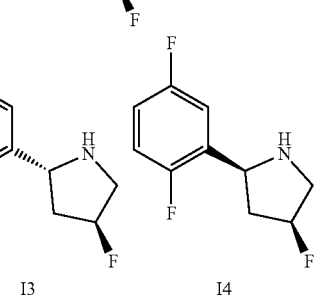

Step A: (R)-4-((tert-butyldimethylsilyl)oxy)pyrrolidin-2-one

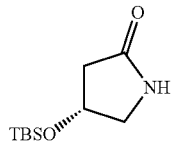 [SMILES: CC(C)(C)[Si](C)(C)O[C@H]1CNC(=O)C1]

(R)-4-hydroxy-2-pyrrolidone (6.0 g) was dissolved in DMF (60 mL), and thereto were added TBDMSCl (9.8 g) and imidazole (6.05 g) at 0° C., and the resulting mixture was warmed to room temperature and stirred for 3 h. After monitoring the completion of the reaction, water was added to the reaction system, and a solid was precipitated, filtered, and dried overnight under an infrared lamp to afford (R)-4-((tert-butyldimethylsilyl)oxy) pyrrolidin-2-one (10.7 g).

$^1$H NMR (400 MHz, CDCl$_3$) δ 7.45 (s, 1H), 4.44 (m, 1H), 3.42 (m, 1H), 2.93 (m, 1H), 2.40 (m, 1H), 1.85 (m, 1H), 0.79 (s, 9H), 0.00 (s, 6H).

Step B: tert-butyl (R)-4-((tert-butyldimethylsilyl)oxy)-2-oxopyrrolidine-1-carboxylate

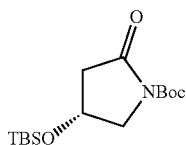 [SMILES: CC(C)(C)OC(=O)N1C[C@H](O[Si](C)(C)C(C)(C)C)CC1=O]

To a solution of (R)-4-((tert-butyldimethylsilyl)oxy)pyrrolidin-2-one (10.67 g) in acetonitrile (150 mL) were added triethylamine (8.26 mL) and DMAP (3.0 g) at 0° C., and thereto was added (Boc)$_2$O (15 mL) dropwise under the protection of nitrogen gas. After completion of the addition, the resulting mixture was stirred for 5 min, and then warmed to room temperature and stirred overnight. The reaction system was poured into water, extracted with ethyl acetate, and purified by silica gel column chromatography (V/V:PE/EA=10/1) to afford tert-butyl (R)-4-((tert-butyldimethylsilyl)oxy)-2-oxopyrrolidine-1-carboxylate (14.5 g).

$^1$H NMR (400 MHz, CDCl$_3$) δ 4.38-4.40 (m, 1H), 3.86 (dd, J=11.4, 5.6 Hz, 1H), 3.62 (dd, J=11.4, 3.2 Hz, 1H), 2.71 (dd, J=15.6, 5.6 Hz, 1H), 2.48 (dd, J=3.4, 5.6 Hz, 1H), 1.56 (s, 9H), 0.89 (m, 9H), 0.08 (m, 6H).

Step C: tert-butyl ((2R)-2-((tert-butyldimethylsilyl)oxy)-4-(2,5-difluorophenyl)-4-hydroxybutyl)carbamate

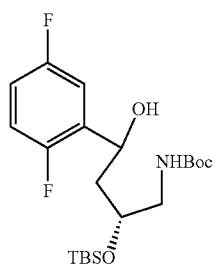 [SMILES: CC(C)(C)OC(=O)NC[C@@H](CC(O)c1cc(F)ccc1F)O[Si](C)(C)C(C)(C)C]

2,5-Difluorobromobenzene (14.8 g) was dissolved in dried tetrahydrofuran (100 mL) and cooled to −78° C., and then thereto was added 2 M isopropylmagnesium chloride solution in THF (35 mL). The reaction system was gradually warmed to 0° C., stirred for 2 h, and then cooled to −78° C. again. To the reaction system was added a solution of tert-butyl (R)-4-((tert-butyldimethylsilyl)oxy)-2-oxopyrrolidine-1-carboxylate (15.6 g) in tetrahydrofuran (50 mL), warmed to 0° C. again and stirred for 3.5 h. To the resulting mixture were added methanol and then sodium borohydride (4.46 g) at 0° C., and stirred for 1 h. After completion of the reaction, the reaction mixture was quenched with a saturated aqueous ammonium chloride solution, extracted with ethyl acetate, and purified by silica gel column chromatography (V/V:PE/EA=5/1) to afford tert-butyl ((2R)-2-((tert-butyldimethylsilyl)oxy)-4-(2,5-difluorophenyl)-4-hydroxybutyl)carbamate (15.4 g).

$^1$H NMR (400 MHz, CDCl$_3$) δ 7.22-7.30 (m, 1H), 6.87-6.97 (m, 2H), 5.16-5.30 (m, 1H), 4.79 (s, 1H), 4.08-4.13 (m, 1H), 3.21-3.37 (m, 2H), 1.92-1.78 (m, 2H), 1.45 (s, 9H), 1.30-1.21 (m, 1H), 0.92 (s, 9H), 0.13 (s, 6H).

Step D: tert-butyl (4R)-4-((tert-butyldimethylsilyl)oxy)-2-(2,5-difluorophenyl) pyrrolidine-1-carboxylate

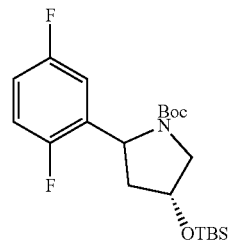 [SMILES: CC(C)(C)OC(=O)N1C[C@H](O[Si](C)(C)C(C)(C)C)CC1c1cc(F)ccc1F]

Tert-butyl ((2R)-2-((tert-butyldimethylsilyl)oxy)-4-(2,5-difluorophenyl)-4-hydroxy butyl)carbamate (15.4 g) was dissolved in dichloromethane and cooled to −60° C., and thereto were added triethylamine (14.8 mL) and methanesulfonyl chloride (3 mL) dropwise, and stirred for 2 h while maintaining the same temperature. Then, DBU (8 mL) was added, warmed to room temperature and stirred overnight. After monitoring the completion of the reaction, the reaction system was poured into water, and extracted with dichloromethane (50 mL×3). The organic phase was washed with a saturated saline solution, dried over sodium sulfate and filtered. The filtrate was concentrated under reduced pressure, and the residue was purified by silica gel column chromatography (V/V:PE/EA=25/1) to afford tert-butyl (4R)-4-((tert-butyldimethylsilyl)oxy)-2-(2,5-difluoro phenyl)pyrrolidine-1-carboxylate (11.28 g).

$^1$H NMR (400 MHz, CDCl$_3$) δ 6.98-7.33 (m, 3H), 5.17-5.49 (m, 1H), 4.50-4.55 (m, 1H), 3.60-3.93 (m, 2H), 2.40-2.60 (m, 1H), 1.92-2.01 (m, 1H), 1.30-1.21 (m, 9H), 0.86-1.08 (m, 9H), 0.08-0.21 (m, 6H).

Step E: tert-butyl (4R)-2-(2,5-difluorophenyl)-4-hydroxypyrrolidine-1-carboxylate

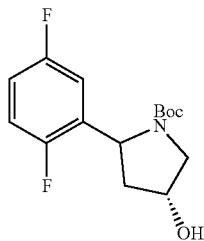 [SMILES: CC(C)(C)OC(=O)N1C[C@H](O)CC1c1cc(F)ccc1F]

Tert-butyl (4R)-4-((tert-butyldimethylsilyl)oxy)-2-(2,5-difluorophenyl)pyrrolidine-1-carboxylate (11.3 g) was dissolved in an appropriate amount of tetrahydrofuran (150 mL), and tetrabutylammonium fluoride (13.0 g) was added at room temperature and stirred for 1 h. After monitoring the completion of the reaction, the reaction system was poured into ice water, extracted with ethyl acetate (×2), and purified by silica gel column chromatography (V/V:PE/EA=3/1) to afford the title compound (6.5 g).

$^1$H NMR (400 MHz, CDCl$_3$) δ 6.80-7.16 (m, 3H), 5.02-5.20 (m, 1H), 4.43-4.51 (m, 1H), 3.57-3.85 (m, 2H), 2.04-2.60 (m, 1H), 1.95-2.02 (m, 1H), 1.58-1.72 (m, 1H), 1.20-1.42 (m, 9H).

Step F: tert-butyl (2R,4S)-2-(2,5-difluorophenyl)-4-fluoropyrrolidine-1-carboxylate (a) and tert-butyl (2S,4S)-2-(2,5-difluorophenyl)-4-fluoropyrrolidine-1-carboxylate (b)

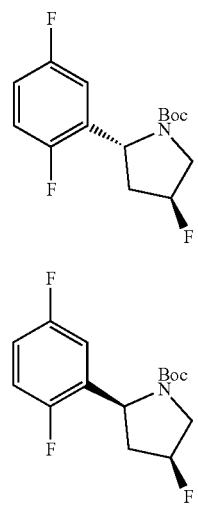

To a solution of tert-butyl (4R)-tert-butyl-2-(2,5-difluorophenyl)-4-hydroxy pyrrolidine-1-carboxylate (1.0 g) in dichloromethane (50 mL) was added DAST (0.883 mL) reagent dropwise at −78° C. and stirred for 2 h while maintaining the same temperature. The resulting mixture was gradually warmed to room temperature and stirred overnight. The reaction mixture was quenched with a saturated aqueous sodium bicarbonate solution at 0° C., and extracted with dichloromethane (×2). The organic phase was washed with a saturated saline solution, dried over sodium sulfate, and purified by silica gel column chromatography (V/V:PE/EA=25/1) to afford tert-butyl (2R,4S)-2-(2,5-difluorophenyl)-4-fluoropyrrolidine-1-carboxylate a (478 mg) and tert-butyl (2S,4S)-2-(2,5-difluoro phenyl)-4-fluoropyrrolidine-1-carboxylate b (311 mg).

Tert-butyl (2R,4S)-2-(2,5-difluorophenyl)-4-fluoropyrrolidine-1-carboxylate (a): $^1$H NMR (400 MHz, CDCl$_3$) δ 6.91-7.00 (m, 3H), 5.12-5.30 (m, 2H), 4.05-4.10 (m, 1H), 3.61-3.71 (m, 1H), 2.71-2.75 (m, 1H), 1.97-2.07 (m, 1H), 1.21-1.62 (m, 9H).

Tert-butyl (2S,4S)-2-(2,5-difluorophenyl)-4-fluoropyrrolidine-1-carboxylate (b)

$^1$H NMR (400 MHz, CDCl$_3$) δ 6.87-7.00 (m, 3H), 5.19-5.32 (m, 2H), 3.70-3.96 (m, 2H), 2.40-2.26 (m, 2H), 1.20-1.65 (m, 9H).

Step G1: (2R,4S)-2-(2,5-difluorophenyl)-4-fluoropyrrolidine (Compound I3)

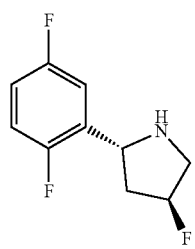

To a solution of tert-butyl (2R,4S)-2-(2,5-difluorophenyl)-4-fluoropyrrolidine-1-carboxylate (478 mg) in dichloromethane (20 mL) was added trifluoroacetic acid (3 mL) at room temperature, and stirred for 1 h. After monitoring the completion of the reaction, the solvent was removed, and to the concentrated mixture was added a saturated aqueous sodium bicarbonate solution. The resulting mixture was extracted with ethyl acetate, and the organic phase was washed with a saturated saline solution, and dried over sodium sulfate. The solvent was removed to afford (2R,4S)-2-(2,5-difluorophenyl)-4-fluoropyrrolidine (299 mg) without further purification.

$^1$H NMR (400 MHz, CDCl$_3$) δ 6.85-7.26 (m, 3H), 5.20-5.35 (m, 1H), 4.71-4.75 (m, 1H), 3.16-3.40 (m, 2H), 2.58-2.69 (m, 1H), 1.66-1.83 (m, 2H).

Step G2: (2S,4S)-2-(2,5-difluorophenyl)-4-fluoropyrrolidine (Compound I4)

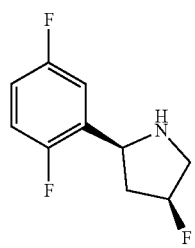

(2S,4S)-2-(2,5-difluorophenyl)-4-fluoropyrrolidine (167 mg) was prepared from the compound b as obtained in step F through the same procedure as in step G1.

$^1$H NMR (400 MHz, CDCl$_3$) δ 6.89-7.26 (m, 3H), 5.20-5.35 (m, 1H), 4.41-4.45 (m, 1H), 3.44-3.53 (m, 1H), 3.00-3.12 (m, 1H), 2.57-2.65 (m, 1H), 1.70-2.04 (m, 2H).

Preparation Example 4
2-(2,5-difluorophenyl)-4,4-difluoropyrrolidine
(Compound I5)

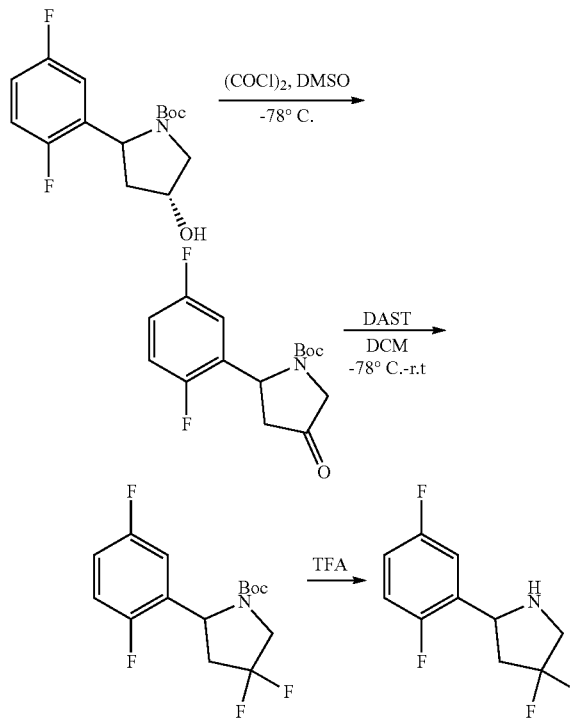

Step A: tert-butyl 2-(2,5-difluorophenyl)-4-oxopyrrolidine-1-carboxylate

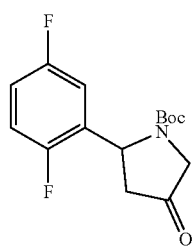 [SMILES: CC(C)(C)OC(=O)N1CC(=O)CC1c1cc(F)ccc1F]

To a solution of oxalyl chloride (195 mg) in dichloromethane (5 mL) was added a solution of DMSO (225 mg) in dichloromethane (1 mL) dropwise at −78° C., and reacted for 30 min while maintaining the same temperature. Then, to the reaction system was added a solution of tert-butyl (4R)-2-(2,5-difluorophenyl)-4-hydroxypyrrolidine-1-carboxylate (Step E in Preparation Example 3, 115 mg) in dichloromethane (3 mL) dropwise, and reacted for 1.5 h while maintaining the same temperature. Triethylamine (0.9 mL) was added to the reaction system dropwise and stirred for 5 min. The resulting mixture was then warmed to room temperature and stirred for 2 h. Then, the reaction mixture was quenched with water, extracted with ethyl acetate, and purified by silica gel column chromatography (V/V:PE/EA=5/1) to afford tert-butyl 2-(2,5-difluorophenyl)-4-oxopyrrolidine-1-carboxylate (31 mg).

$^1$H NMR (400 M Hz, CDCl$_3$) δ 7.05-6.88 (m, 3H), 5.4 (s, 1H), 4.06 and 3.92 (d, J=19.1, 2H), 3.20 (dd, J=19.1, 10.6 Hz, 1H), 2.61 (d, J=19.1 Hz, 1H), 1.42 (s, 9H).

Step B: tert-butyl 2-(2,5-difluorophenyl)-4,4-difluoropyrrolidine-1-carboxylate

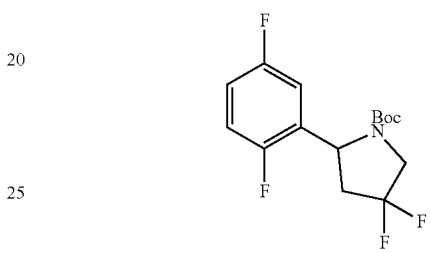

Tert-butyl 2-(2,5-difluorophenyl)-4-oxopyrrolidine-1-carboxylate (50 mg) was dissolved in dichloromethane (10 mL) and cooled to −78° C., and thereto was added DAST (0.1 mL) reagent dropwise, and reacted for 2 h while maintaining the same temperature. Then, the resulting mixture was warmed to room temperature and stirred overnight, and then quenched with a saturated aqueous sodium bicarbonate solution and extracted with dichloromethane. The organic phase was dried over sodium sulfate, and purified by silica gel column chromatography (V/V:PE/EA=15/1) to afford tert-butyl 2-(2,5-difluorophenyl)-4,4-difluoropyrrolidine-1-carboxylate (24 mg).

$^1$H NMR (400 MHz, CDCl$_3$) δ 7.08-6.84 (m, 3H), 5.30-5.20 (m, 1H), 4.14-3.79 (m, 2H), 2.98-2.76 (m, 1H), 2.44-2.21 (m, 1H), 1.46-1.25 (m, 9H).

Step C:
2-(2,5-difluorophenyl)-4,4-difluoropyrrolidine

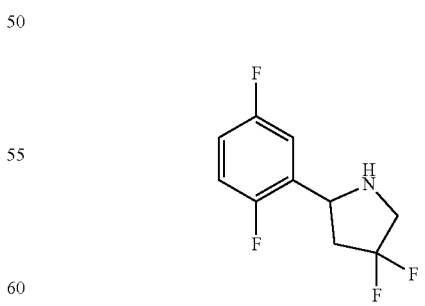

Compound I5 (288 mg) was prepared from tert-butyl 2-(2,5-difluorophenyl)-4,4-difluoropyrrolidine-1-carboxylate (460 mg) through the same procedure as in step G1 of Preparation Example 3 (1 mL of trifluoroacetic acid and 15 mL of dichloromethane).

¹H NMR (400 MHz, CDCl₃) δ 7.40-7.27 (m, 1H), 7.11-6.89 (m, 2H), 4.77-4.60 (m, 1H), 3.49-3.29 (m, 2H), 2.78-2.69 (m, 1H), 2.19-2.05 (m, 1H), 1.79-1.98 (s, 1H).

Preparation Example 5 (3R)-5-(2,5-difluorophenyl)-3-hydroxypyrrolidine (Compound I6)

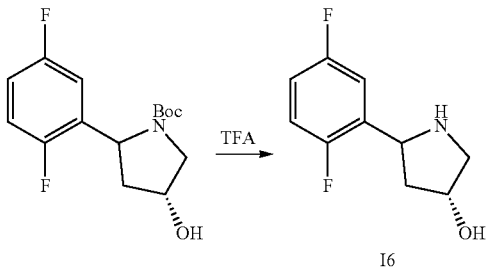

Compound I6 (1.21 g) was prepared from tert-butyl (4R)-2-(2,5-difluorophenyl)-4-hydroxypyrrolidine-1-carboxylate (2.15 g) through the same procedure as in step G1 of Preparation Example 3 (12 mL of trifluoroacetic acid and 80 mL of dichloromethane).

¹H NMR (400 MHz, CDCl₃) δ 7.37-7.23 (m, 1H), 7.01-6.83 (m, 2H), 4.77-4.66 (t, J=8.0 Hz, 0.5H), 4.56-4.42 (m, 1H), 4.37 (t, J=8.0 Hz, 0.5H), 3.27-3.12 (m, 1H), 3.10-3.02 (m, 1H), 2.67-2.57 (m, 0.5H), 2.34-2.29 (0.5H), 1.92-1.59 (m, 3H).

Preparation Example 6
5-(2,5-difluorophenyl)-pyrrolidin-3-one (Compound I7)

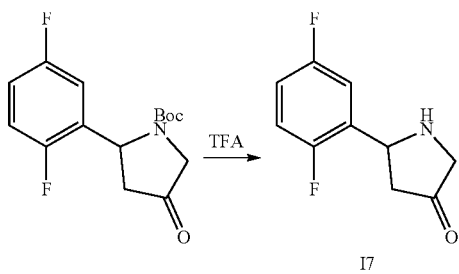

To a solution of tert-butyl 2-(2,5-difluorophenyl)-4-oxopyrrolidine-1-carboxylate (Step A in Preparation Example 4, 100 mg) in dichloromethane (10 mL) was added trifluoroacetic acid (1 mL) at room temperature and stirred for 1 h. The solvent was removed by evaporation under reduced pressure to afford Compound I7, which was directly used in a next reaction.

Example 1 ethyl (R)-2-amino-5-(2-(2,5-difluorophenyl)pyrrolidin-1-yl)pyrazolo[1,5-a]pyrimidine-3-carboxylate

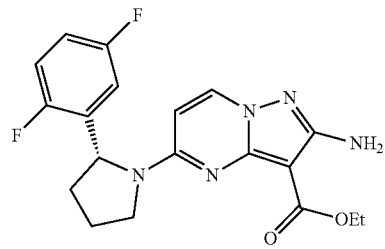 [SMILES: CCOC(=O)c1c(N)nn2ccc(N3CCC[C@@H]3c3cc(F)ccc3F)nc12]

Step A: ethyl (Z)-3-amino-4,4,4-trichloro-2-cyano-butenoate

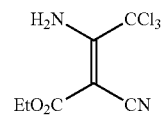

To a solution of ethyl cyanoacetate (41.22 g) and trichloroacetonitrile (100 g) in ethanol (120 mL) was added triethylamine (2.0 g) dropwise at 0° C. After completion of the addition, the resulting mixture was reacted at 0° C. for 2 hours, and was gradually warmed to room temperature and continuously reacted for 30 minutes. After the completion of the reaction, the solvent was removed by concentration, and the residue was dissolved in dichloromethane, and then purified by silica gel column chromatography (eluting with dichloromethane) to afford the title compound (93.0 g).

¹H NMR (400 MHz, CDCl₃) δ 10.20 (brs, 1H), 6.93 (brs, 1H), 4.30 (q, J=7.2 Hz, 2H), 1.33 (t, J=7.2 Hz, 3H).

Step B: ethyl 3,5-diamino-1H-pyrazole-4-carboxylate

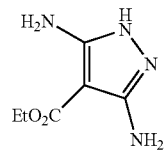

To a solution of ethyl (Z)-3-amino-4,4,4-trichloro-2-cyano-butenoate (92.1 g) in DMF (250 mL) was slowly added hydrazine hydrate (50 g) dropwise, and the reaction mixture was heated to 100° C. and reacted for 1.5 hours under stirring. The solvent was removed by concentration, and the residue was slurried with dichloromethane and then allowed to stand overnight. The resulting mixture was suction-filtered, and the solid was collected, rinsed with dichloromethane and dried to afford the title compound (41.0 g).

¹H NMR (400 MHz, DMSO-d₆) δ 10.4 (brs, 1H), 5.35 (brs, 4H), 4.13 (q, J=7.2 Hz, 2H), 1.24 (t, J=7.2 Hz, 3H). m/z=171[M+1]⁺.

Step C: ethyl 2-amino-5-oxo-4,5-dihydropyrazolo[1,5-a]pyrimidine-3-carboxylate

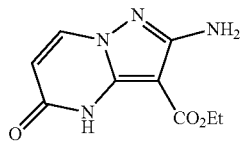 [SMILES: CCOC(=O)c1c(N)nn2ccc(=O)[nH]c12]

To a solution of sodium ethoxide (33.2 g) in ethanol (500 mL) were sequentially added ethyl 3,5-diamino-1H-pyrazole-4-carboxylate (20.8 g) and 1,3-dimethyl pyrimidine-2,4(1H,3H)-dione (17.0 g) at room temperature. Then, the resulting mixture was warmed to 90° C. and reacted for 12 hours. After the completion of the reaction, the mixture was cooled to room temperature, and adjusted to pH=7 with 1N hydrochloric acid solution. The solid was collected and rinsed with ethanol to afford the title compound (18.4 g).

$^1$H NMR (400 MHz, DMSO-$d_6$) δ 11.17 (brs, 1H), 8.24 (d, J=8.0 Hz, 1H), 5.93 (s, 2H), 5.90 (d, J=8.0 Hz, 1H), 4.26 (q, J=7.2 Hz, 2H), 1.27 (t, J=7.2 Hz, 3H). m/z=223[M+1]$^+$.

Step D: ethyl 2-amino-5-chloropyrazolo[1,5-a]pyrimidine-3-carboxylate and ethyl 2-acetamido-5-chloropyrazolo[1,5-a]pyrimidine-3-carboxylate

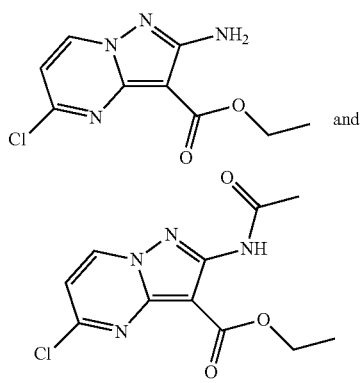

To a solution of ethyl 2-amino-5-oxo-4,5-dihydropyrazolo[1,5-a]pyrimidine-3-carboxylate (33.6 g) in acetonitrile (500 mL) was added phosphorus oxychloride (110 mL) at room temperature. The resulting mixture was heated to 40° C. and reacted for 5 hours. After cooling, the mixture was concentrated under reduced pressure. To the residue were added a saturated aqueous sodium bicarbonate solution and ethyl acetate. The mixed solution was layered, and the aqueous phase was extracted once with ethyl acetate. The ethyl acetate phase was combined, washed with a saturated aqueous sodium chloride solution, dried over anhydrous sodium sulfate and filtered. The filtrate was concentrated to afford a brown oil. Then the brown oil was purified by silica gel column chromatography (eluting with ethyl acetate/petroleum ether (V/V=2/1)) to afford ethyl 2-amino-5-chloropyrazolo[1,5-a]pyrimidine-3-carboxylate (4.5 g) and ethyl 2-acetamido-5-chloropyrazolo[1,5-a]pyrimidine-3-carboxylate (3.0 g)

Ethyl 2-amino-5-chloropyrazolo[1,5-a]pyrimidine-3-carboxylate: $^1$H NMR (400 MHz, CDCl$_3$) δ 8.29 (d, J=7.2 Hz, 1H), 6.80 (d, J=7.2 Hz, 1H), 5.51 (brs, 2H), 4.43 (q, J=7.2 Hz, 2H), 1.44 (t, J=7.2 Hz, 3H). m/z=241[M+1]$^+$.

Ethyl 2-acetamido-5-chloropyrazolo[1,5-a]pyrimidine-3-carboxylate: $^1$H NMR (400 MHz, DMSO-$d_6$) δ 10.10 (s, 1H), 8.65 (d, J=7.2 Hz, 1H), 6.98 (d, J=7.2 Hz, 1H), 4.47 (q, J=7.2 Hz, 2H), 2.35 (s, 3H), 1.47 (t, J=7.2 Hz, 3H). m/z=283 [M+1]$^+$.

Step E: ethyl (R)-2-amino-5-(2-(2,5-difluorophenyl)pyrrolidin-1-yl)pyrazolo[1,5-a]pyrimidine-3-carboxylate

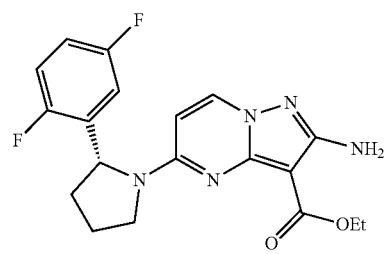

To a solution of ethyl 2-amino-5-chloropyrazolo[1,5-a]pyrimidine-3-carboxylate (300 mg) and (R)-2-(2,5-difluorophenyl)pyrrolidine (275 mg) in n-butanol (2.5 mL) was added N,N-dimethylisopropylamine (324.0 mg), and the mixture was reacted in a sealed tube at 160° C. for 5 hours. The reaction mixture was cooled to room temperature, and suction-filtered under reduced pressure. The filter cake was rinsed with ethanol and dried to afford the title compound (365 mg).

$^1$H NMR (400 MHz, DMSO-$d_6$) δ 8.52-8.16 (m, 1H), 7.41-6.82 (m, 3H), 6.44-6.28 (m, 1H), 5.96 (s, 2H), 5.63-5.20 (m, 1H), 4.24-3.86 (m, 3H), 3.62-3.40 (m, 1H), 2.48-2.28 (m, 1H), 2.08-1.78 (m, 3H), 1.38-1.01 (m, 3H).

$^1$H NMR (400 MHz, CDCl$_3$) δ 8.20-7.81 (m, 1H), 7.12-6.65 (m, 3H), 6.24-5.50 (m, 1H), 5.45-4.98 (m, 3H), 4.48-3.46 (m, 4H), 2.63-2.26 (m, 1H), 2.19-1.92 (m, 3H), 1.53-1.05 (m, 3H). m/z=388[M+1]$^+$.

Example 2 (R)-2-amino-5-(2-(2,5-difluorophenyl)pyrrolidin-1-yl)pyrazolo[1,5-a]pyrimidine-3-carboxylic Acid

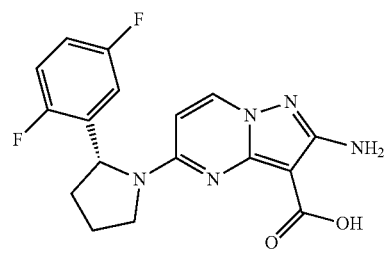

To a solution of ethyl (R)-2-amino-5-(2-(2,5-difluorophenyl)pyrrolidin-1-yl)pyrazolo[1,5-a]pyrimidine-3-carboxylate (144 mg) in methanol/water (V/V=1/10, 3.0 mL) was added 4N sodium hydroxide solution (0.95 mL) dropwise at room temperature. After completion of the dropwise addition, the resulting mixture was warmed to 90° C. and reacted for 12 hours. After the completion of the reaction, the mixture was adjusted to about pH=7 with a 1N hydrochloric acid solution, and the precipitate was collected, washed with water and dried to afford the title compound (80.0 mg).

¹H NMR (400 MHz, CDCl₃) δ 10.50 (brs, 1H), 8.55-8.15 (m, 1H), 7.40-6.88 (m, 3H), 6.51-6.20 (m, 1H), 5.95 (s, 2H), 5.54-5.15 (m, 1H), 4.05-3.88 (m, 1H), 3.80-3.51 (m, 1H), 2.55-2.35 (m, 1H), 2.11-1.80 (m, 3H). m/z=360[M+1]⁺.

Example 3 (R)-2-amino-5-(2-(2,5-difluorophenyl) pyrrolidin-1-yl)-N-methylpyrazolo[1,5-a]pyrimidine-3-carboxamide

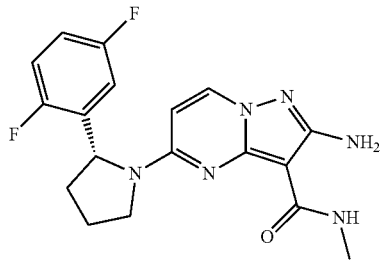 [SMILES: CNC(=O)c1c(N)nn2ccc(N3CCC[C@@H]3c3cc(F)ccc3F)nc12]

To a solution of (R)-2-amino-5-(2-(2,5-difluorophenyl) pyrrolidin-1-yl)pyrazolo[1,5-a]pyrimidine-3-carboxylic acid (20.0 mg), methylamine hydrochloride (5.0 mg) and HATU (25 mg) in dried DMF (1.0 mL) was added N,N-dimethyl isopropylamine (16.9 mg) dropwise under N₂ protection. After completion of the dropwise addition, the resulting mixture was reacted for 5 hours at room temperature. After the completion of the reaction, water and ethyl acetate were added to the mixture, and stirred for 15 minutes. The mixed solution was layered, and the aqueous phase was extracted once with ethyl acetate. Then the ethyl acetate phase was combined, washed with a saturated sodium chloride solution, dried over anhydrous sodium sulfate and filtered. The filtrate was concentrated to afford a light yellow residue, which was then purified by silica gel column chromatography (eluting with dichloromethane/methanol V/V=25/1) to afford the title compound (8.0 mg).

¹H NMR (400 MHz, CDCl₃) δ 8.13-7.88 (m, 1H), 7.13-6.86 (m, 3H), 6.75-6.64 (m, 1H), 6.14-5.95 (m, 1H), 5.60-5.20 (m, 3H), 3.95-3.74 (m, 2H), 3.10-2.70 (m, 3H), 2.60-2.43 (m, 1H), 2.23-1.95 (m, 3H). m/z=373[M+1]⁺.

Example 4 (R)-2-amino-5-(2-(2,5-difluorophenyl) pyrrolidin-1-yl)pyrazolo[1,5-a]pyrimidine-3-carboxamide

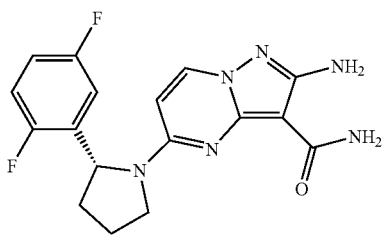

To a solution of ethyl (R)-2-amino-5-(2-(2,5-difluorophenyl)pyrrolidin-1-yl)pyrazolo[1,5-a]pyrimidine-3-carboxylate (310 mg) in methanol (5.0 mL) was added aqueous ammonia (5.0 mL), and the mixture was reacted in a sealed tube at 150° C. for 48 hours. Then, water and ethyl acetate were added to the mixture, and stirred for 5 minutes. The mixed solution was layered, and the aqueous phase was extracted once with ethyl acetate. Then the ethyl acetate phase was combined, washed with a saturated sodium chloride solution, dried over anhydrous sodium sulfate and filtered.

The filtrate was concentrated to afford a light yellow residue, which was then purified by silica gel column chromatography (eluting with petroleum ether/ethyl acetate V/V=1/1) to afford the title compound (45.0 mg).

¹H NMR (400 MHz, CDCl₃) δ 8.18-7.88 (m, 1H), 7.10-6.67 (m, 3H), 6.21-5.98 (m, 1H), 5.65-4.98 (m, 5H), 4.05-3.58 (m, 2H), 2.60-2.40 (m, 1H), 2.24-1.95 (m, 3H). m/z=359[M+1]⁺.

Example 5 ethyl 2-amino-5-(2-(2,5-difluorophenyl) pyrrolidin-1-yl)pyrazolo[1,5-a]pyrimidine-3-carboxylate

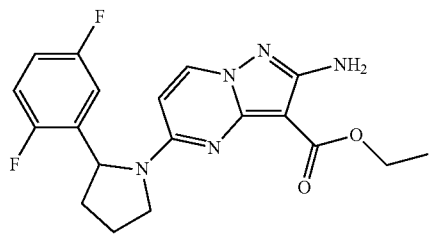 [SMILES: CCOC(=O)c1c(N)nn2ccc(N3CCCC3c3cc(F)ccc3F)nc12]

2-(2,5-Difluorophenyl)pyrrolidine (365 mg) and ethyl 2-amino-5-chloropyrazolo[1,5-a]pyrimidine-3-carboxylate (400 mg) were added into n-butanol, and reacted overnight in a sealed tube at 160° C., and then purified by silica gel column chromatography (V/V:PE/EA=1/3) to afford the title compound (607 mg).

¹H NMR (400 MHz, CDCl₃) δ 7.90 (s, 1H), 7.10-6.70 (m, 3H), 6.20-5.00 (m, 4H), 4.23-3.40 (m, 4H), 2.60-2.30 (m, 1H), 2.18-1.90 (m, 3H), 1.50-1.33 (m, 3H). m/z=388[M+1]⁺.

Example 6 2-amino-5-(2-(2,5-difluorophenyl)pyrrolidin-1-yl)pyrazolo[1,5-a]pyrimidine-3-carboxamide

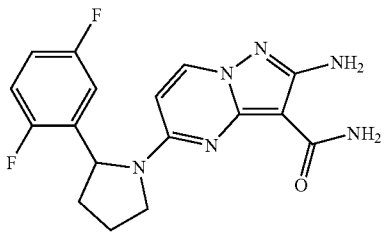 [SMILES: NC(=O)c1c(N)nn2ccc(N3CCCC3c3cc(F)ccc3F)nc12]

To a sealed tube made of iron and filled with a solution of ethyl 2-amino-5-(2-(2,5-difluorophenyl)pyrrolidin-1-yl) pyrazolo[1,5-a]pyrimidine-3-carboxylate (200 mg) in n-butanol (6 mL) was added aqueous ammonia (10 mL) at room temperature, and refluxed at 160° C. for 36 h under stirring. The resulting mixture was concentrated under reduced pressure, and then silica gel was directly added thereto to obtain the sample, which was purified by silica gel column chromatography to afford the title compound (25 mg).

$^1$H NMR (400 MHz, CDCl$_3$) δ 8.18-7.83 (m, 1H), 7.15-6.66 (m, 3H), 6.24-5.56 (m, 2H), 5.52-4.70 (m, 4H), 4.06-3.53 (m, 2H), 2.59-2.42 (m, 1H), 2.27-1.92 (m, 3H). m/z=359[M+1]$^+$.

Example 7 ethyl 5-(2-(2,5-difluorophenyl)pyrrolidin-1-yl)-2-(3-methylureido)pyrazolo[1,5-a]pyrimidine-3-carboxylate

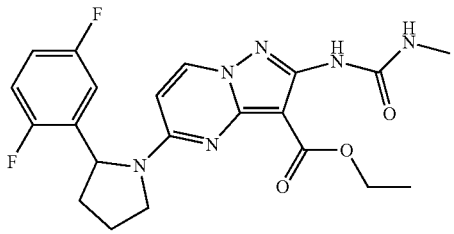 [SMILES: CCOC(=O)c1c(NC(=O)NC)nn2ccc(N3CCCC3c3cc(F)ccc3F)nc12]

Step A: ethyl 5-(2-(2,5-difluorophenyl)pyrrolidin-1-yl)-2-(((4-nitrophenoxy)carbonyl) amino)pyrazolo[1,5-c]pyrimidine-3-carboxylate

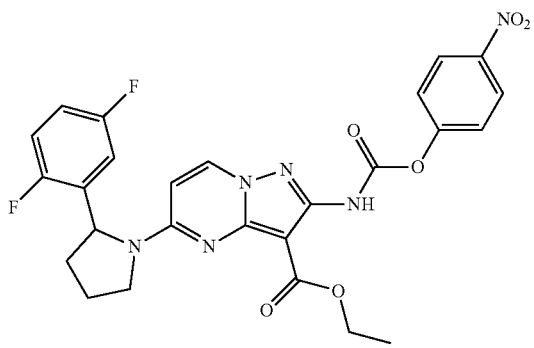 [SMILES: CCOC(=O)c1c(NC(=O)Oc2ccc([N+](=O)[O-])cc2)nn2ccc(N3CCCC3c3cc(F)ccc3F)nc12]

To a solution of ethyl 2-amino-5-(2-(2,5-difluorophenyl)pyrrolidin-1-yl)pyrazolo[1,5-a]pyrimidine-3-carboxylate (337 mg) in THF (15 mL) was slowly added in portions 57% of sodium hydride (74 mg) at 0° C., warmed to room temperature and stirred for 1 h. The reaction system was cooled to 0° C. again, and to the reaction mixture was added p-nitrophenylchloroformate (264 mg). Then, the reaction mixture was warmed to room temperature and stirred for 2 h. The reaction mixture was then quenched with water and extracted with ethyl acetate. The organic layer was separated, dried over anhydrous sodium sulfate, and filtered. The filtrate was concentrated under reduced pressure to afford a crude product of the title compound, which was used directly in a next step without purification.

Step B: ethyl 5-(2-(2,5-difluorophenyl)pyrrolidin-1-yl)-2-(3-methylureido)pyrazolo[1,5-c]pyrimidine-3-carboxylate

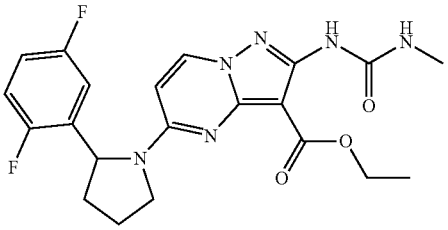 [SMILES: CCOC(=O)c1c(NC(=O)NC)nn2ccc(N3CCCC3c3cc(F)ccc3F)nc12]

The crude product of ethyl 5-(2-(2,5-difluorophenyl)pyrrolidin-1-yl)-2-(((4-nitrophenoxy)carbonyl)amino)pyrazolo[1,5-a]pyrimidine-3-carboxylate obtained in the above step A was dissolved in THF (10 mL) at room temperature. Methylamine (4 mL) was added to the reaction solution and stirred for 10 min. After the competition of the reaction, silica gel was added thereto to obtain the sample. Then the resulting mixture was concentrated under reduced pressure, and the residue purified by dry silica gel column chromatography to afford the title compound (281 mg).

$^1$H NMR (400 MHz, CDCl$_3$) δ 8.91-8.63 (m, 1H), 8.20-8.71 (m, 2H), 7.19-6.80 (m, 3H), 6.26 (s, 0.5H), 5.95-5.62 (m, 1H), 5.15 (s, 0.5H), 4.52-3.44 (m, 4H), 2.94 (d, J=7.2 Hz, 3H), 2.62-2.28 (m, 1H), 2.19-1.95 (m, 3H), 1.57-1.42 (m, 2H), 1.37-1.05 (m, 1H). m/z=445[M+1]$^+$.

Example 8 ethyl 5-(2-(2,5-difluorophenyl)pyrrolidin-1-yl)-2-((4-methylphenyl) sulfonylamino)pyrazolo[1,5-a]pyrimidine-3-carboxylate

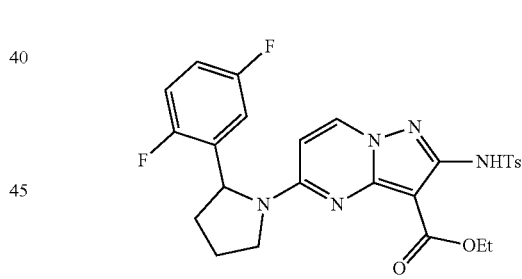

To a solution of ethyl 2-amino-5-(2-(2,5-difluorophenyl)pyrrolidin-1-yl)pyrazolo[1,5-a]pyrimidine-3-carboxylate (389 mg) in pyridine (1.5 mL) was added TsCl (475 mg), and reacted at 90° C. for 8 hours. After the completion of the reaction, a saturated aqueous sodium bicarbonate solution and ethyl acetate were added, and stirred for 15 minutes. The mixed solution was layered, and the aqueous phase was extracted once with ethyl acetate. The ethyl acetate phase was combined, washed with a saturated sodium chloride solution, dried over anhydrous sodium sulfate and filtered. The filtrate was concentrated to afford a light yellow residue, which was then purified by silica gel column chromatography (eluting with dichloromethane/methanol V/V=30/1) to afford the title compound (350 mg).

$^1$H NMR (400 MHz, CDCl$_3$) δ 9.52-9.31 (m, 1H), 8.28-8.01 (m, 1H), 7.94 (d, J=8.0 Hz, 2H), 7.22 (d, J=8.0 Hz, 2H), 7.13-6.60 (m, 3H), 5.81-5.60 (m, 1H), 5.20-5.13 (m, 1H), 4.41-4.10 (m, 2H), 4.05-3.48 (m, 2H), 2.60-2.40 (m, 1H), 2.20-1.92 (m, 3H), 1.45-1.12 (m, 6H). m/z=542[M+1]⁺.

Example 9 ethyl (R)-2-acetylamino-5-(2-(2,5-difluorophenyl)pyrrolidin-1-yl)pyrazolo[1,5-a]pyrimidine-3-carboxylate

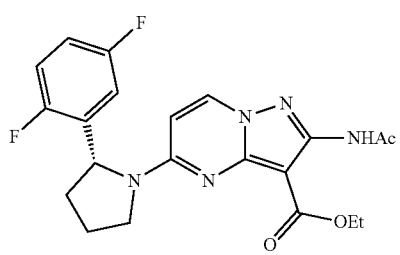 [SMILES: CCOC(=O)c1c(NC(C)=O)nn2ccc(N3CCC[C@@H]3c3cc(F)ccc3F)nc12]

To a solution of ethyl 2-acetamido-5-chloropyrazolo[1,5-a]pyrimidine-3-carboxylate (50.0 mg) and (R)-2-(2,5-difluorophenyl)pyrrolidine (40.0 mg) in n-butanol (1.5 mL) was added N,N-dimethylisopropylamine (45.0 mg), and then reacted in a sealed tube at 160° C. for 5 hours. The reaction mixture was cooled to room temperature, and suction-filtered under reduced pressure. The filter cake was rinsed with ethanol and dried to afford the title compound (25.0 mg).

$^1$H NMR (400 MHz, CDCl$_3$) δ 10.13-9.88 (m, 1H), 8.40-8.12 (m, 1H), 7.15-6.65 (m, 3H), 5.89-5.78 (m, 1H), 5.21-5.11 (m, 1H), 4.48-4.16 (m, 2H), 4.14-3.51 (m, 2H), 2.60-2.20 (m, 4H), 2.18-1.97 (m, 3H), 1.45-1.17 (m, 3H). m/z=430[M+1]⁺.

Example 10 (2-amino-5-((R)-2-(2,5-difluorophenyl)pyrrolidin-1-yl)pyrazolo[1,5-a]pyrimidin-3-yl)(3-hydroxypyrrolidin-1-yl)methanone

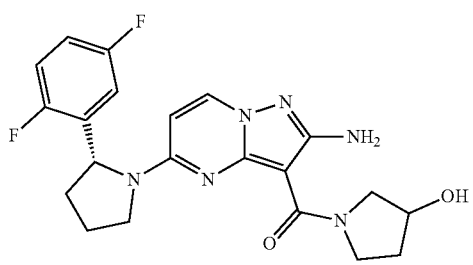 [SMILES: Nc1nn2ccc(N3CCC[C@@H]3c3cc(F)ccc3F)nc2c1C(=O)N1CCC(O)C1]

Referring to Example 3, the title compound (9.0 mg) was prepared from (R)-2-amino-5-(2-(2,5-difluorophenyl)pyrrolidin-1-yl)pyrazolo[1,5-c]pyrimidine-3-carboxylic acid (20.0 mg) and 3-hydroxypyrrolidine (8.0 mg).

$^1$H NMR (400 MHz, CDCl$_3$) δ 8.13-7.91 (m, 1H), 7.10-6.60 (m, 3H), 6.20-5.00 (m, 4H), 4.56-4.35 (m, 1H), 4.08-3.30 (m, 6H), 2.51-2.31 (m, 1H), 2.15-1.71 (m, 6H). m/z=429[M+1]⁺.

Example 11 (R)-2-amino-5-(2-(2,5-difluorophenyl)pyrrolidin-1-yl)-N-(4-hydroxycyclohexyl)pyrazolo[1,5-c]pyrimidine-3-carboxamide

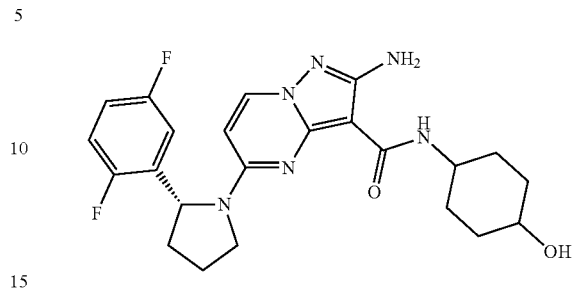

Referring to Example 3, the title compound (3.0 mg) was prepared from (R)-2-amino-5-(2-(2,5-difluorophenyl)pyrrolidin-1-yl)pyrazolo[1,5-c]pyrimidine-3-carboxylic acid (13.0 mg) and 4-aminocyclohexanol (6.21 mg).

$^1$H NMR (400 MHz, CDCl$_3$) δ 8.40-8.01 (m, 1H), 7.78-7.58 (m, 1H), 7.13-6.58 (m, 3H), 6.22-6.08 (m, 1H), 5.53-5.50 (m, 2H), 5.25-5.05 (m, 1H), 4.02-3.51 (m, 4H), 2.60-2.38 (m, 1H), 2.20-1.15 (m, 12H). m/z=457[M+1]⁺.

Example 12 2-amino-5-((R)-2-(2,5-difluorophenyl)pyrrolidin-1-yl)-N-((trans)-4-hydroxycyclohexyl)pyrazolo[1,5-a]pyrimidine-3-carboxamide

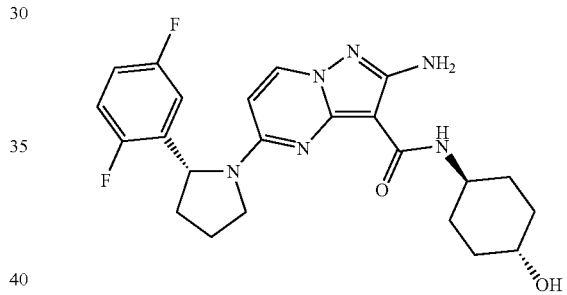

Referring to Example 3, the title compound (12.0 mg) was prepared from (R)-2-amino-5-(2-(2,5-difluorophenyl)pyrrolidin-1-yl)pyrazolo[1,5-a]pyrimidine-3-carboxylic acid (30.0 mg) and (trans)-4-aminocyclohexanol (6.21 mg).

$^1$H NMR (400 MHz, CDCl$_3$) δ 8.21-7.85 (m, 1H), 7.80-7.58 (m, 1H), 7.15-6.58 (m, 3H), 6.22-6.00 (m, 1H), 5.82-5.05 (m, 3H), 4.02-3.48 (m, 4H), 2.60-2.38 (m, 1H), 2.20-1.10 (m, 12H). m/z=457[M+1]⁺.

Example 13 (R)-2-amino-5-(2-(2,5-difluorophenyl)pyrrolidin-1-yl)-N-(2-hydroxyethyl)pyrazolo[1,5-a]pyrimidine-3-carboxamide

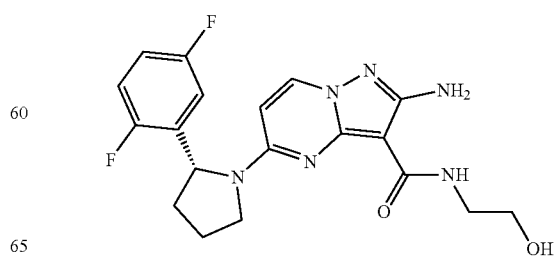

Referring to Example 3, the title compound (5.0 mg) was prepared from (R)-2-amino-5-(2-(2,5-difluorophenyl)pyrrolidin-1-yl)pyrazolo[1,5-a]pyrimidine-3-carboxylic acid (30.0 mg) and 2-aminoethanol (7.56 mg).

$^1$H NMR (400 MHz, CDCl$_3$) δ 8.20-7.80 (m, 1H), 7.55-7.35 (m, 1H), 7.10-6.65 (m, 3H), 6.20-6.00 (m, 1H), 5.65-5.30 (m, 3H), 4.00-3.20 (m, 6H), 2.60-2.40 (m, 1H), 2.23-1.92 (m, 4H). m/z=403[M+1]$^+$.

Example 14 (R)-2-amino-5-(2-(2,5-difluorophenyl)pyrrolidin-1-yl)-N-(4-fluorophenyl)pyrazolo[1,5-a]pyrimidine-3-carboxamide

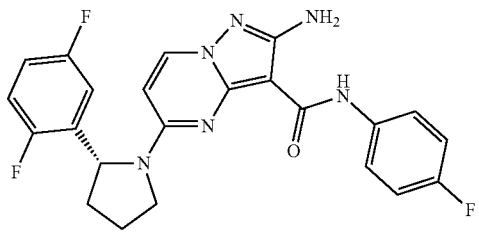 [SMILES: Nc1nn2ccc(N3CCC[C@@H]3c3cc(F)ccc3F)nc2c1C(=O)Nc1ccc(F)cc1]

Referring to Example 3, the title compound (11.0 mg) was prepared from (R)-2-amino-5-(2-(2,5-difluorophenyl)pyrrolidin-1-yl)pyrazolo[1,5-a]pyrimidine-3-carboxylic acid (30.0 mg) and p-fluoroaniline (13.98 mg).

$^1$H NMR (400 MHz, CDCl$_3$) δ 9.88-9.60 (m, 1H), 9.05-8.80 (m, 1H), 8.21-7.80 (m, 1H), 7.71-7.48 (m, 1H), 7.36-6.53 (m, 5H), 6.28-6.03 (m, 1H), 5.80-5.55 (m, 1H), 4.18-3.20 (m, 4H), 2.68-2.38 (m, 1H), 2.03-1.91 (m, 3H). m/z=453[M+1]$^+$.

Example 15 (R)-2-amino-5-(2-(2,5-difluorophenyl)pyrrolidin-1-yl)-N,N-dimethylpyrazolo[1,5-c]pyrimidine-3-carboxamide

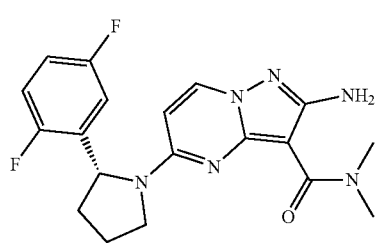 [SMILES: CN(C)C(=O)c1c(N)nn2ccc(N3CCC[C@@H]3c3cc(F)ccc3F)nc12]

Referring to Example 3, the title compound (8.0 mg) was prepared from (R)-2-amino-5-(2-(2,5-difluorophenyl)pyrrolidin-1-yl)pyrazolo[1,5-a]pyrimidine-3-carboxylic acid (30.0 mg) and N,N-dimethylamine (5.67 mg).

$^1$H NMR (400 MHz, CDCl$_3$) δ 8.21-7.93 (m, 1H), 7.11-6.60 (m, 3H), 6.20-5.01 (m, 4H), 3.98-3.53 (m, 2H), 3.30-2.60 (m, 6H), 2.52-2.38 (m, 1H), 2.14-1.96 (m, 3H). m/z=387[M+1]$^+$.

Example 16 (R)-2-amino-5-(2-(2,5-difluorophenyl)pyrrolidin-1-yl)-N-((1-hydroxy-2-methylpropan-2-yl)oxy)pyrazolo[1,5-c]pyrimidine-3-carboxamide

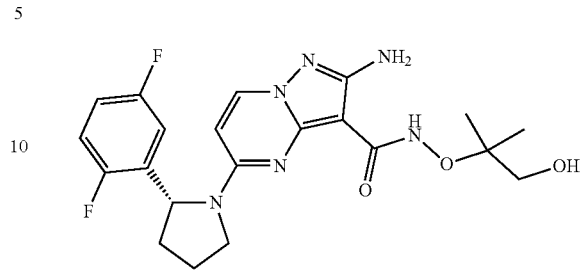

Referring to Example 3, the title compound (3.0 mg) was prepared from (R)-2-amino-5-(2-(2,5-difluorophenyl)pyrrolidin-1-yl)pyrazolo[1,5-c]pyrimidine-3-carboxylic acid (13.0 mg) and 2-(aminooxy)-2-methyl-1-propanol hydrochloride (prepared with reference to WO2010003025, 5.67 mg).

$^1$H NMR (400 MHz, CDCl$_3$) δ 9.20-9.01 (m, 1H), 8.18-7.85 (m, 1H), 7.19-6.58 (m, 3H), 5.80-5.03 (m, 4H), 4.05-3.20 (m, 4H), 2.60-2.38 (m, 1H), 2.21-2.00 (m, 3H), 1.40-1.15 (m, 7H). m/z=447[M+1]$^+$.

Example 17 2-amino-5-((R)-2-(2,5-difluorophenyl)pyrrolidin-1-yl)-N-((2,2-dimethyl-1,3-dioxolan-4-yl)methoxy)pyrazolo[1,5-c]pyrimidine-3-carboxamide

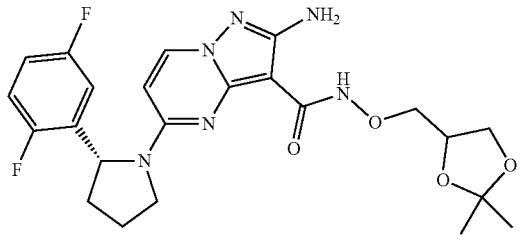 [SMILES: CC1(C)OCC(CONC(=O)c2c(N)nn3ccc(N4CCC[C@@H]4c4cc(F)ccc4F)nc23)O1]

Referring to Example 3, the title compound (6.0 mg) was prepared from (R)-2-amino-5-(2-(2,5-difluorophenyl)pyrrolidin-1-yl)pyrazolo[1,5-c]pyrimidine-3-carboxylic acid (13.0 mg) and O-((2,2-dimethyl-1,3-dioxolan-4-yl)methyl)hydroxyamine (7.94 mg).

$^1$H NMR (400 MHz, CDCl$_3$) δ 9.43-9.30 (m, 1H), 8.40-7.80 (m, 1H), 7.15-6.65 (m, 3H), 5.78-5.06 (m, 4H), 4.60-4.32 (m, 1H), 4.12-3.60 (m, 5H), 2.60-2.40 (m, 1H), 2.28-2.00 (m, 4H), 1.47 (s, 3H), 1.40 (s, 3H). m/z=489[M+1]$^+$.

Example 18 (R)-2-amino-N-(tert-butoxy)-5-(2-(2,5-difluorophenyl)pyrrolidin-1-yl)pyrazolo[1,5-c]pyrimidine-3-carboxamide

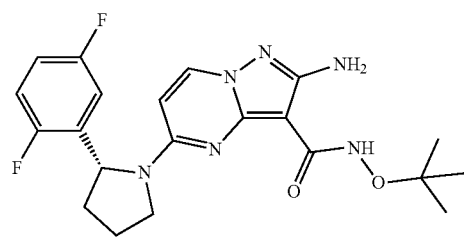 [SMILES: CC(C)(C)ONC(=O)c1c(N)nn2ccc(N3CCC[C@@H]3c3cc(F)ccc3F)nc12]

Referring to Example 3, the title compound (6.5 mg) was prepared from (R)-2-amino-5-(2-(2,5-difluorophenyl)pyrrolidin-1-yl)pyrazolo[1,5-c]pyrimidine-3-carboxylic acid (13.0 mg) and tert-butylhydroxyamine (4.81 mg).

$^1$H NMR (400 MHz, CDCl$_3$) δ 9.89-9.60 (m, 1H), 8.20-7.85 (m, 1H), 7.15-6.45 (m, 3H), 5.80-5.02 (m, 3H), 4.05-3.40 (m, 2H), 2.60-2.35 (m, 1H), 2.20-1.95 (m, 4H), 1.30 (s, 9H). m/z=431[M+1]$^+$.

Example 19 (R)-2-amino-5-(2-(2,5-difluorophenyl)pyrrolidin-1-yl)-N-(2-(dimethyl amino)ethyl)pyrazolo[1,5-a]pyrimidine-3-carboxamide

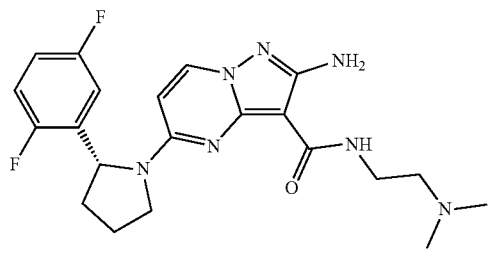 [SMILES: CN(C)CCNC(=O)c1c(N)nn2ccc(N3CCC[C@@H]3c3cc(F)ccc3F)nc12]

Referring to Example 3, the title compound (25.0 mg) was prepared from (R)-2-amino-5-(2-(2,5-difluorophenyl)pyrrolidin-1-yl)pyrazolo[1,5-c]pyrimidine-3-carboxylic acid (50.0 mg) and N,N-dimethylethylenediamine (17.5 mg).

$^1$H NMR (400 MHz, CDCl$_3$) δ 8.20-7.80 (m, 1H), 7.45-7.05 (m, 1H), 7.01-6.65 (m, 2H), 5.80-5.51 (m, 1H), 5.48-5.03 (m, 3H), 4.20-3.40 (m, 5H), 3.05-2.81 (m, 3H), 2.66 (s, 6H), 2.25-1.97 (m, 3H). m/z=430[M+1]$^+$.

Example 20 ethyl (R)-5-(2-(2,5-difluorophenyl)pyrrolidin-1-yl)-2-(methyl amino)pyrazolo[1,5-a]pyrimidine-3-carboxylate

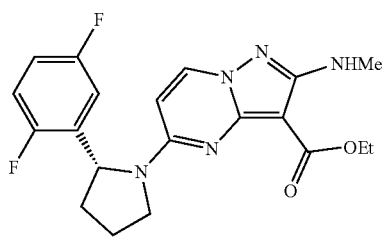 [SMILES: CCOC(=O)c1c(NC)nn2ccc(N3CCC[C@@H]3c3cc(F)ccc3F)nc12]

To a solution of ethyl (R)-2-amino-5-(2-(2,5-difluorophenyl)pyrrolidin-1-yl)pyrazolo[1,5-a]pyrimidine-3-carboxylate (260.0 mg) in methanol (3.0 mL) was added an aqueous formaldehyde solution (0.2 mL) at room temperature, and thereto sodium cyanoborohydride (127 mg) was added in portions, and stirred at room temperature for 12 h. After the completion of the reaction, the reaction solution was poured into ice water, made weakly basic with an aqueous sodium hydroxide solution, and then extracted with ethyl acetate. The organic phase was separated, dried over anhydrous sodium sulfate, and filtered. The filtrate was concentrated under reduced pressure, and the residue was purified and separated by silica gel column chromatography to afford the title compound (180 mg).

$^1$H NMR (400 MHz, CDCl$_3$) δ 8.20-7.90 (m, 1H), 7.15-6.60 (m, 3H), 6.21-6.05 (m, 1H), 5.80-5.55 (m, 1H), 5.21-5.01 (m, 1H), 4.40-3.60 (m, 4H), 2.99 (m, 3H), 2.60-2.38 (m, 1H), 2.18-1.95 (m, 3H), 1.46-1.20 (m, 3H). m/z=402 [M+1]$^+$.

Example 21 (R)-5-(2-(2,5-difluorophenyl)pyrrolidin-1-yl)-2-(methylamino)pyrazolo[1,5-a]pyrimidine-3-carboxamide

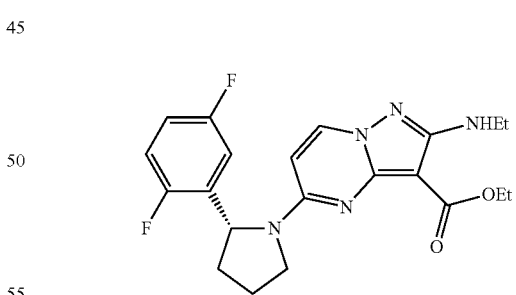

Referring to Example 4, the title compound (20 mg) was prepared from ethyl (R)-5-(2-(2,5-difluorophenyl)pyrrolidin-1-yl)-2-(methylamino)pyrazolo[1,5-a]pyrimidine-3-carboxylate (150.0 mg).

$^1$H NMR (400 MHz, CDCl$_3$) δ 8.20-7.90 (m, 1H), 7.15-6.65 (m, 4H), 6.48-6.30 (m, 1H), 6.15-5.96 (m, 1H), 5.70-4.95 (m, 2H), 4.00-3.58 (m, 2H), 2.97 (d, J=4.4 Hz, 3H), 2.60-2.40 (m, 1H), 2.20-1.85 (m, 3H). m/z=373[M+1]$^+$.

Example 22 ethyl (R)-5-(2-(2,5-difluorophenyl)pyrrolidin-1-yl)-2-(ethylamino)pyrazolo[1,5-a]pyrimidine-3-carboxylate Referring to Example 20, ethyl (R)-2-amino-5-(2-(2,5-difluorophenyl)pyrrolidin-1-yl)pyrazolo[1,5-a]pyrimidine-3-carboxylate (50.0 mg) reacted with 40% of aqueous acetaldehyde solution (0.051 mL) to afford the title compound (40.0 mg).

$^1$H NMR (400 MHz, CDCl$_3$) δ 8.20-7.90 (m, 1H), 7.18-6.68 (m, 3H), 6.21-6.01 (m, 1H), 5.82-5.52 (m, 1H), 5.22-5.01 (m, 1H), 4.50-3.72 (m, 4H), 3.38 (dq, J=7.2, 5.6 Hz, 2H), 2.59-2.32 (m, 1H), 2.15-1.90 (m, 3H), 1.45-1.10 (m, 6H). m/z=416[M+1]$^+$.

Example 23 ethyl (R)-5-(2-(2,5-difluorophenyl)pyrrolidin-1-yl)-2-((2-morpholinylethyl)amino)pyrazolo[1,5-a]pyrimidine-3-carboxylate

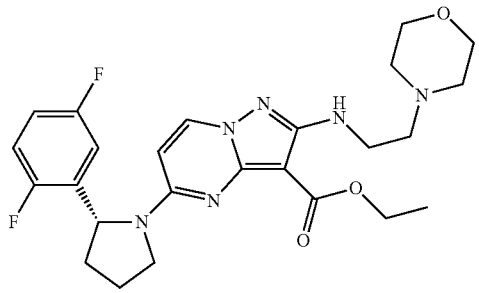 [SMILES: CCOC(=O)c1c(NCCN2CCOCC2)nn2ccc(N3CCC[C@@H]3c3cc(F)ccc3F)nc12]

Referring to Example 20, the title compound (4.4 mg) was prepared from ethyl (R)-2-amino-5-(2-(2,5-difluorophenyl)pyrrolidin-1-yl)pyrazolo[1,5-a]pyrimidine-3-carboxylate (20.0 mg) and 4-(2,2-dimethoxyethyl)morpholine (14.7 mg).

$^1$H NMR (400 MHz, CDCl$_3$) δ 8.18-7.80 (m, 1H), 7.15-6.60 (m, 3H), 6.55-6.38 (m, 1H), 5.85-5.50 (m, 1H), 5.22-5.00 (m, 1H), 4.40-3.51 (m, 10H), 3.08-2.30 (m, 7H), 2.20-1.95 (m, 3H), 1.55-1.30 (m, 3H). m/z=501[M+1]$^+$.

Example 24 5-(2-(2,5-difluorophenyl)pyrrolidin-1-yl)pyrazolo[1,5-a]pyrimidin-2-amine

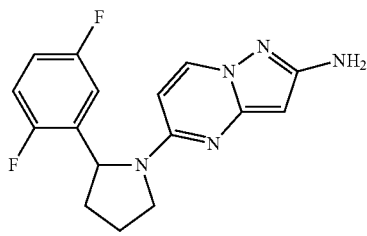 [SMILES: Nc1cc2nc(N3CCCC3c3cc(F)ccc3F)ccn2n1]

To ethyl 2-amino-5-(2-(2,5-difluorophenyl)pyrrolidin-1-yl)pyrazolo[1,5-a]pyrimidine-3-carboxylate (829 mg) solid in a round bottom flask was added 48% of sulfuric acid (20 mL) at room temperature, and refluxed at 100° C. for 12 h under stirring. After the completion of the reaction, the reaction solution was poured into ice water, made weakly basic with an aqueous sodium hydroxide solution, and then extracted with ethyl acetate. The organic phase was separated, dried over anhydrous sodium sulfate, and filtered. The filtrate was concentrated under reduced pressure, and the residue was purified by silica gel column chromatography to afford the title compound (376 mg).

$^1$H NMR (400 MHz, CDCl$_3$) δ 8.17-8.15 (d, J=6.8 Hz, 1H), 7.31-7.25 (m, 1H), 7.15-7.10 (m, 1H), 6.86-6.82 (m, 1H), 5.95-5.69 (m, 1H), 5.37-5.26 (m, 1H), 5.17 (brs, 2H), 5.11 (brs, 1H), 3.86 (t, J=8.4 Hz, 1H), 3.60-3.47 (m, 1H), 2.46-2.33 (m, 1H), 2.02-1.93 (m, 1H), 1.91-1.83 (m, 2H). m/z=316[M+1]$^+$.

Example 25 (R)-5-(2-(2,5-difluorophenyl)pyrrolidin-1-yl)pyrazolo[1,5-c]pyrimidin-2-amine

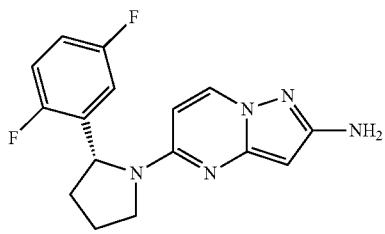 [SMILES: Nc1cc2nc(N3CCC[C@@H]3c3cc(F)ccc3F)ccn2n1]

To ethyl (R)-2-amino-5-(2-(2,5-difluorophenyl)pyrrolidin-1-yl)pyrazolo[1,5-a]pyrimidine-3-carboxylate (2.0 g) solid in a round bottom flask was added 48% of sulfuric acid (24 mL), and refluxed at 100° C. for 12 h under stirring. After the completion of the reaction, the reaction solution was poured into ice water, made weakly basic with an aqueous sodium hydroxide solution, and then extracted with ethyl acetate. The organic phase was separated, dried over anhydrous sodium sulfate, and filtered. The filtrate was concentrated under reduced pressure, and the residue was purified by silica gel column chromatography to afford the title compound (1.354 g).

$^1$H NMR (400 MHz, CDCl$_3$) δ 7.89 (d, J=7.6 Hz, 1H), 7.06-7.00 (m, 1H), 6.93-6.87 (m, 1H), 6.75-6.71 (m, 1H), 5.68 (brs, 1H), 5.46 (brs, 1H), 5.24 (brs, 1H), 4.22-3.63 (m, 4H), 3.50-2.41 (m, 1H), 2.05-1.92 (m, 3H). m/z=316[M+1]$^+$.

Example 26 ethyl 2-(5-(2-(2,5-difluorophenyl)pyrrolidin-1-yl)-2-((4-methoxybenzyl) amino)pyrazolo[1,5-a]pyrimidin-3-yl)oxazole-4-carboxylate

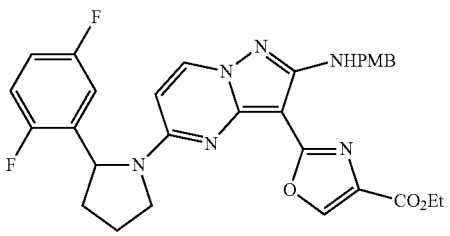

Step A: ethyl 2-amino-5-(2-(2,5-difluorophenyl)pyrrolidin-1-yl)pyrazolo[1,5-a]pyrimidine-3-carboxylate

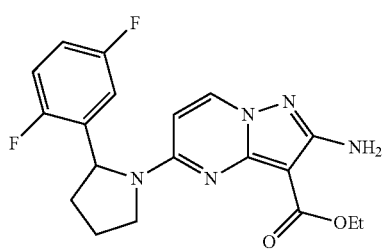 [SMILES: CCOC(=O)c1c(N)nn2ccc(N3CCCC3c3cc(F)ccc3F)nc12]

To a solution of ethyl 2-amino-5-chloropyrazolo[1,5-a]pyrimidine-3-carboxylate (3.0 g) and 2-(2,5-difluorophenyl)pyrrolidine (2.51) g) in n-butanol (20 mL) was added DIEA (4.2 mL) at room temperature, and the reaction mixture was heated to 160° C., and refluxed at this temperature for 8 h under stirring. After the completion of the reaction, the resulting mixture was concentrated under reduced pressure to remove n-butanol, and silica gel was added thereto to obtain the sample. Then the resulting mixture was purified by dry silica gel column chromatography to afford the title compound (4.56 g), which was directly used in a next step.

Step B: ethyl 5-(2-(2,5-difluorophenyl)pyrrolidin-1-yl)-2-(4-methoxybenzylamino)pyrazolo[1,5-a]pyrimidine-3-carboxylate

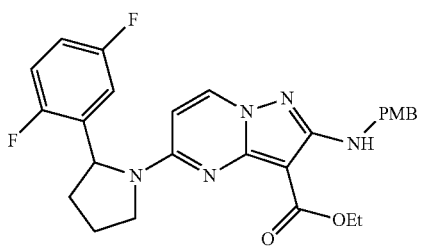

To a solution of ethyl 2-amino-5-(2-(2,5-difluorophenyl)pyrrolidin-1-yl)pyrazolo[1,5-a]pyrimidine-3-carboxylate (2.0 g) obtained in Step A in THF (20 mL) was slowly added 57% of sodium hydride (1.98 g) in portions at 0° C., and then warmed to room temperature and stirred for 1 h. The reaction system was cooled to 0° C. again. Then p-methoxybenzyl chloride (4.2 mL) was added to the reaction mixture, and warmed to 90° C. and refluxed for 12 h. The reaction was quenched by pouring ice water thereinto and then the resulting mixture was extracted with ethyl acetate. The organic phase was separated, dried over anhydrous sodium sulfate, and filtered. The filtrate was concentrated under reduced pressure, and the residue was purified by silica gel column chromatography to afford the title compound (1.366 g).

$^1$H NMR (400 MHz, CDCl$_3$) δ 8.05-7.93 (m, 1H), 7.35-7.24 (m, 2H), 7.09-6.98 (m, 1H), 6.95-6.81 (m, 3H), 6.79-6.70 (m, 1H), 6.56-6.41 (m, 1H), 6.23-5.52 (m, 1H), 5.28-5.06 (m, 1H), 4.49 (d, J=5.6 Hz, 2H), 4.42-4.18 (m, 2H), 4.13-3.92 (m, 2H), 3.78 (s, 3H), 2.61-2.34 (m, 1H), 2.07-1.95 (m, 3H), 1.53-1.18 (m, 3H). m/z=508[M+1]$^+$.

Step C: 5-(2-(2,5-difluorophenyl)pyrrolidin-1-yl)-2-(4-methoxybenzylamino)pyrazolo[1,5-a]pyrimidine-3-carboxamide

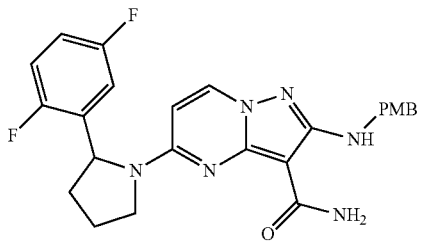

To a solution of ethyl 5-(2-(2,5-difluorophenyl)pyrrolidin-1-yl)-2-(4-methoxybenzyl amino)pyrazolo[1,5-a]pyrimidine-3-carboxylate (900 mg) in n-butanol (10 mL) in a sealed tube made of iron was added aqueous ammonia (10 mL) at room temperature, stirred and refluxed at 160° C. for 36 h. The resulting mixture was concentrated under reduced pressure, and then silica gel was directly added thereto to obtain the sample, which was purified by silica gel column chromatography to afford the title compound (143 mg).

$^1$H NMR (400 MHz, CDCl$_3$) δ 8.18-7.94 (m, 1H), 7.31-7.25 (m, 2H), 7.12-6.98 (m, 1H), 6.94-6.90 (m, 1H), 6.87-6.74 (m, 3H), 6.72-6.66 (m, 1H), 6.20-5.93 (m, 1H), 5.81-4.65 (m, 3H), 4.49 (d, J=6.0 Hz, 2H), 4.02-3.81 (m, 5H), 2.58-2.39 (m, 1H), 2.26-1.97 (m, 3H). m/z=479[M+1]$^+$.

Step D: ethyl 2-(5-(2-(2,5-difluorophenyl)pyrrolidin-1-yl)-2-((4-methoxybenzyl) amino)pyrazolo[1,5-a]pyrimidin-3-yl)oxazole-4-carboxylate

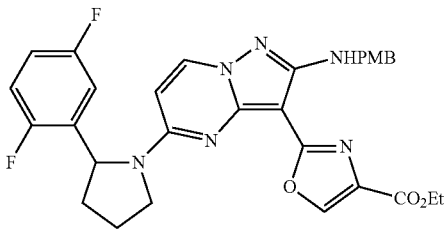

To a solution of 5-(2-(2,5-difluorophenyl)pyrrolidin-1-yl)-2-(4-methoxybenzyl amino)pyrazolo[1,5-a]pyrimidine-3-carboxamide (20 mg) in THF (3 mL) were added 80% of ethyl 3-bromopyruvate (12 mg) and sodium bicarbonate (11 mg) at room temperature, and then warmed to 90° C. and refluxed for 12 h. The resulting mixture was concentrated under reduced pressure, and then silica gel was directly added thereto to obtain the sample, which was purified by silica gel column chromatography to afford the title compound (2.12 mg).

$^1$H NMR (400 MHz, CDCl$_3$) δ 8.21-8.08 (m, 1H), 8.06-7.95 (m, 1H), 7.34 (d, J=8.8 Hz, 2H), 7.07-6.96 (m, 1H), 6.93-6.64 (m, 5H), 6.40-4.83 (m, 2H), 4.58 (d, J=10.0 Hz, 2H), 4.36 (dd, J=14.4 Hz, J=7.2 Hz, 2H), 4.11 (t, J=7.2 Hz, 2H), 3.78 (s, 3H), 2.61-2.38 (m, 1H), 2.16-1.99 (m, 3H), 1.42-1.05 (m, 3H). m/z=575[M+1]$^+$.

Example 27 5-(2-(2,5-difluorophenyl)pyrrolidin-1-yl)-3-(4-methyloxazol-2-yl)pyrazolo[1,5-c]pyrimidin-2-amine

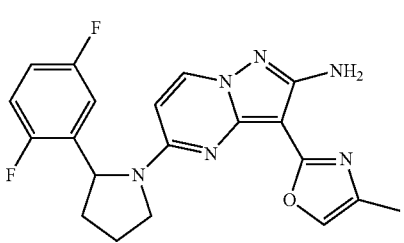 [SMILES: Cc1coc(-c2c(N)nn3ccc(N4CCCC4c4cc(F)ccc4F)nc23)n1]

Step A: 5-(2-(2,5-difluorophenyl)pyrrolidin-1-yl)-N-(4-methoxybenzyl)-3-(4-methyloxazol-2-yl)pyrazolo[1,5-c]pyrimidin-2-amine

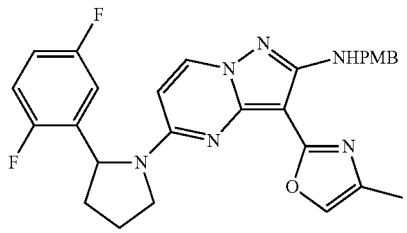

Referring to the experimental procedure in step D of Example 26, ethyl 3-bromopyruvate was replaced with 1-bromoacetone to afford a crude product of the title compound (5 mg), which was directly used in a next step without further purification.

Step B: 5-(2-(2,5-difluorophenyl)pyrrolidin-1-yl)-3-(4-methyloxazol-2-yl)pyrazolo[1,5-a]Pyrimidin-2-amine

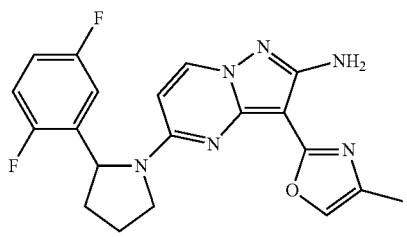 [SMILES: Cc1coc(-c2c(N)nn3ccc(N4CCCC4c4cc(F)ccc4F)nc23)n1]

To a solution of 5-(2-(2,5-difluorophenyl)pyrrolidin-1-yl)-N-(4-methoxybenzyl)-3-(4-methyloxazol-2-yl)pyrazolo[1,5-a]pyrimidin-2-amine (5 mg) in DCM (2 mL) was slowly added trifluoroacetate (0.5 mL) at 0° C., and then warmed to room temperature and stirred for 3 h. The resulting mixture was concentrated under reduced pressure to remove trifluoroacetic acid and dichloromethane. The residue was diluted with ethyl acetate, and washed with a saturated aqueous sodium bicarbonate solution and then a saturated saline solution. The organic phase was separated, dried over anhydrous sodium sulfate and filtered. The filtrate was concentrated under reduced pressure and the residue was purified by silica gel column chromatography to afford the title compound (2.65 mg).

$^1$H NMR (400 MHz, CDCl$_3$) δ 8.11-7.93 (m, 1H), 7.42-7.31 (m, 1H), 7.09-6.95 (m, 1H), 6.90-6.65 (m, 2H), 6.23-5.02 (m, 4H), 4.20-3.42 (m, 2H), 2.58-2.43 (m, 1H), 2.20 (s, 3H), 2.16-1.92 (m, 3H). m/z=397[M+1]$^+$.

Example 28 5-(2-(2,5-difluorophenyl)pyrrolidin-1-yl)-3-(4-methylthiazol-2-yl)pyrazolo[1,5-c]pyrimidin-2-amine

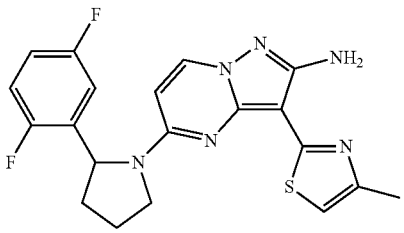 [SMILES: Cc1csc(-c2c(N)nn3ccc(N4CCCC4c4cc(F)ccc4F)nc23)n1]

Step A: 5-(2-(2,5-difluorophenyl)pyrrolidin-1-yl)-2-(4-methoxybenzylamino)pyrazolo[1,5-c]pyrimidine-3-thiocarboxamide

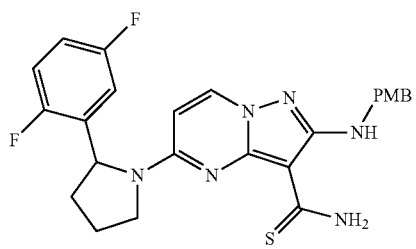

To a solution of 5-(2-(2,5-difluorophenyl)pyrrolidin-1-yl)-2-(4-methoxybenzyl amino)pyrazolo[1,5-a]pyrimidine-3-carboxamide (200 mg) in toluene (12 mL) was added Lawson's reagent (102 mg) at room temperature. The mixture was warmed to 100° C. and refluxed for 12 h under the protection of nitrogen gas, and then concentrated under reduced pressure. Silica gel was directly added thereto to obtain the sample, which was purified by silica gel column chromatography to afford the title compound (95 mg), which was directly used in a next step.

Step B: 5-(2-(2,5-difluorophenyl)pyrrolidin-1-yl)-N-(4-methoxybenzyl)-3-(4-methylthiazol-2-yl)pyrazolo[1,5-c]pyrimidin-2-amine

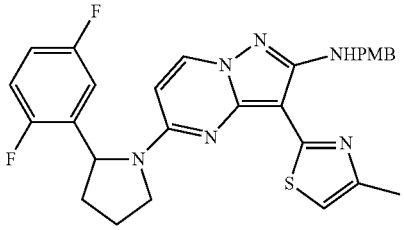

Referring to the experimental procedure in step D of Example 26, ethyl 3-bromopyruvate was replaced with 1-bromoacetone to afford a crude product of the title compound (34 mg), which was directly used in a next step without further purification.

Step C: 5-(2-(2,5-difluorophenyl)pyrrolidin-1-yl)-3-(4-methylthiazol-2-yl)pyrazolo[1,5-a]pyrimidin-2-amine

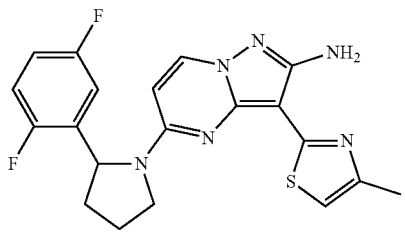 [SMILES: Cc1csc(-c2c(N)nn3ccc(N4CCCC4c4cc(F)ccc4F)nc23)n1]

Referring to the experimental procedure in step B of Example 27, 5-(2-(2,5-difluorophenyl)pyrrolidin-1-yl)-N-(4-methoxybenzyl)-3-(4-methyloxazol-2-yl)pyrazolo[1,5-a]pyrimidin-2-amine was replaced with 5-(2-(2,5-difluorophenyl) pyrrolidin-1-yl-N-(4-methoxybenzyl)-3-(4-methylthiazol-2-yl)pyrazolo[1,5-a]pyrimidin-2-amine to afford the title compound (10 mg).
$^1$H NMR (400 MHz, CDCl$_3$) δ 8.20-7.85 (m, 1H), 7.08-6.99 (m, 1H), 6.94-6.41 (m, 3H), 6.26-5.40 (m, 3.5H), 5.15-4.89 (m, 0.5H), 4.30-3.21 (m, 2H), 2.61-2.28 (m, 4H), 2.16-1.92 (m, 3H). m/z=413[M+1]$^+$.

Example 29 ethyl 2-(2-amino-5-(2-(2,5-difluorophenyl)pyrrolidin-1-yl)pyrazolo[1,5-a]pyrimidin-3-yl)thiazole-4-carboxylate

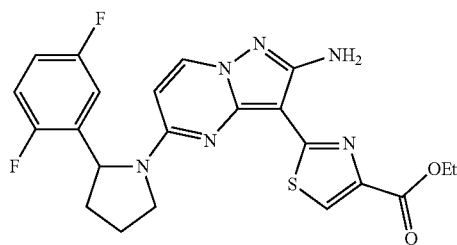 [SMILES: CCOC(=O)c1csc(-c2c(N)nn3ccc(N4CCCC4c4cc(F)ccc4F)nc23)n1]

Step A: ethyl 2-(5-(2-(2,5-difluorophenyl)pyrrolidin-1-yl)-2-((4-methoxybenzyl) amino)pyrazolo[1,5-a]pyrimidin-3-yl)thiazole-4-carboxylate

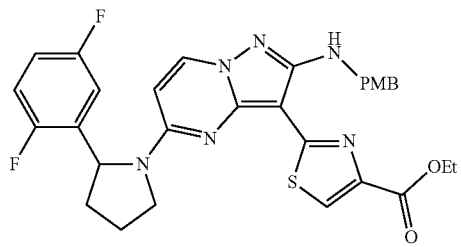

Referring to the experimental procedure in step D of Example 26, 5-(2-(2,5-difluorophenyl)pyrrolidin-1-yl)-2-(4-methoxybenzylamino)pyrazolo[1,5-a]pyrimidine-3-carboxamide was replaced with 5-(2-(2,5-difluorophenyl)pyrrolidin-1-yl)-2-(4-methoxybenzylamino)pyrazolo[1,5-a]pyrimidine-3-thiocarboxamide (115 mg) to afford crude product of the title compound (75 mg), which was directly used in a next step without further purification.

Step B: ethyl 2-(2-amino-5-(2-(2,5-difluorophenyl)pyrrolidin-1-yl)pyrazolo[1,5-a]pyrimidin-3-yl)thiazole-4-carboxylate

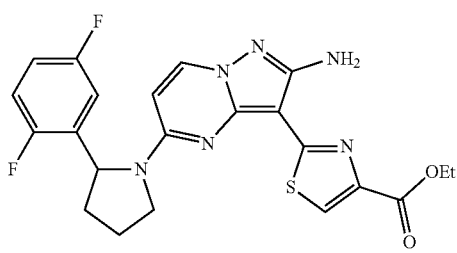 [SMILES: CCOC(=O)c1csc(-c2c(N)nn3ccc(N4CCCC4c4cc(F)ccc4F)nc23)n1]

Referring to the experimental procedure in step B of Example 27, 5-(2-(2,5-difluorophenyl)pyrrolidin-1-yl)-N-(4-methoxybenzyl)-3-(4-methyloxazol-2-yl)pyrazolo[1,5-c]pyrimidin-2-amine was replaced with ethyl 2-(5-(2-(2,5-difluorophenyl) pyrrolidine-1-yl)-2-((4-methoxybenzyl) amino)pyrazolo[1,5-c]pyrimidin-3-yl)thiazole-4-carboxylate (30 mg) to afford the title compound (13 mg).
$^1$H NMR (400 MHz, CDCl$_3$) δ 8.23-7.81 (m, 2H), 7.13-7.00 (m, 1H), 6.96-6.81 (m, 1H), 6.72 (brs, 1H), 6.28-5.42 (m, 3H), 5.17-5.02 (m, 1H), 4.39 (dd, J=13.2 Hz, J=6.4 Hz, 2H), 4.19-3.46 (m, 2H), 2.50 (m, 1H), 2.18-1.94 (m, 3H), 1.47-1.22 (m, 3H). m/z=471[M+1]$^+$.

Example 30 (2-(2-amino-5-(2-(2,5-difluorophenyl)pyrrolidin-1-yl)pyrazolo[1,5-a]pyrimidin-3-yl)thiazol-4-yl)((S)-3-hydroxypyrrolidin-1-yl)methanone

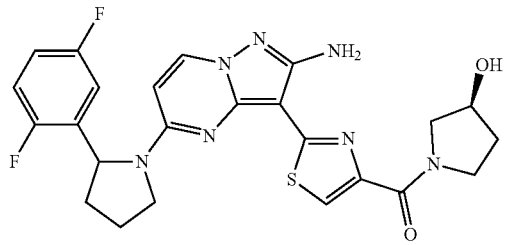 [SMILES: Nc1nn2ccc(N3CCCC3c3cc(F)ccc3F)nc2c1-c1nc(C(=O)N2CC[C@H](O)C2)cs1]

Step A: 2-(5-(2-(2,5-difluorophenyl)pyrrolidin-1-yl)-2-((4-methoxybenzyl)amino) pyrazolo[1,5-a]pyrimidin-3-yl)thiazole-4-carboxylic acid

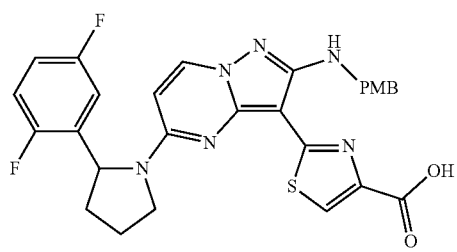

To a solid of ethyl 2-(5-(2-(2,5-difluorophenyl)pyrrolidin-1-yl)-2-(4-methoxybenzyl) amino)pyrazolo[1,5-a]pyrimidin-3-yl)thiazole-4-carboxylate (45 mg) in a round bottom flask was added methanol/water (V/V=3/1, 8 mL) at room temperature, and then cooled to 0° C. Sodium hydroxide (15 mg) was added and stirred at room temperature for 8 h. After the completion of the reaction, the resulting mixture was concentrated under reduced pressure to remove methanol, made acidic with hydrochloric acid, and then extracted with ethyl acetate. The organic phase was separated, dried over anhydrous sodium sulfate, and filtered. The filtrate was concentrated under reduced pressure to afford a crude product of the title compound (50 mg), which was directly used in a next step without purification.

Step B: (2-(2-amino-5-(2-(2,5-difluorophenyl)pyrrolidin-1-yl)pyrazolo[1,5-a]pyrimidin-3-yl)thiazol-4-yl)((S)-3-hydroxypyrrolidin-1-yl)methanone

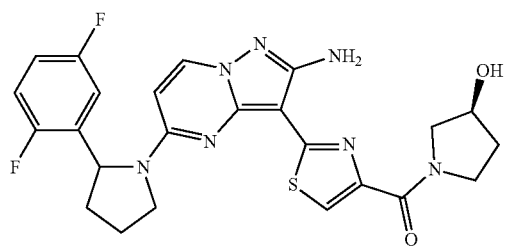 [SMILES: Nc1nn2ccc(N3CCCC3c3cc(F)ccc3F)nc2c1-c1nc(C(=O)N2CC[C@H](O)C2)cs1]

A crude product of 2-(5-(2-(2,5-difluorophenyl)pyrrolidin-1-yl)-2-(4-methoxybenzyl) amino)pyrazolo[1,5-a]pyrimidin-3-yl)thiazole-4-carboxylic acid (50 mg) obtained in the above step, (S)-3-hydroxypyrrolidine (9 mg) and DIEA (45 mg) were dissolved in DMF (5 mL) at room temperature. HATU (35 mg) was added to the reaction mixture at 0° C., and then warmed to room temperature and stirred for 16 h. Then, water was added thereto to quench the reaction. The resulting mixture was extracted with ethyl acetate, and the organic phase was washed with water, and then a saturated saline solution. The organic phase was separated, dried over anhydrous sodium sulfate and filtered. The filtrate was concentrated under reduced pressure to afford a crude product of the condensation product, which was then dissolved in DCM. TFA (1.0 mL) was added thereto and reacted for 3 h. The resulting mixture was concentrated under reduced pressure and the residue was purified by silica gel column chromatography to afford the title compound (15 mg).

$^1$H NMR (400 MHz, CDCl$_3$) δ 8.25-7.59 (m, 2H), 7.05 (brs, 1H), 6.95-6.56 (m, 2H), 6.18-5.96 (m, 0.5H), 5.93-5.42 (m, 1H), 5.24-5.01 (m, 0.5H), 4.55 (brs, 1H), 4.31-3.38 (m, 7H), 2.62-2.41 (m, 1H), 2.22-1.94 (m, 5H). m/z=512[M+1]$^+$.

Example 31 2-amino-5-(2-(2,5-difluorophenyl)pyrrolidin-1-yl)pyrazolo[1,5-a]pyrimidine-3-thioamide

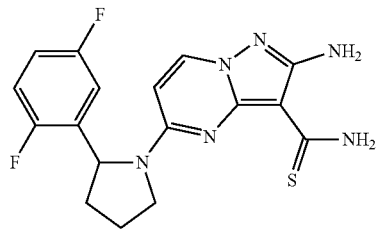 [SMILES: NC(=S)c1c(N)nn2ccc(N3CCCC3c3cc(F)ccc3F)nc12]

Step A: 5-(2-(2,5-difluorophenyl)pyrrolidin-1-yl)-2-(4-methoxybenzylamino)pyrazolo[1,5-a]pyrimidine-3-thiocarboxamide

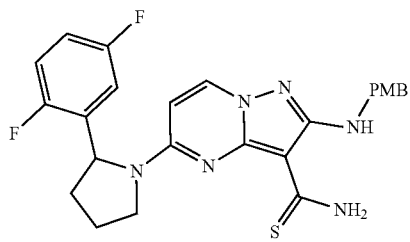

To a solution of 5-(2-(2,5-difluorophenyl)pyrrolidin-1-yl)-2-(4-methoxybenzyl amino)pyrazolo[1,5-a]pyrimidine-3-carboxamide (200 mg) in toluene (12 mL) was added Lawson's reagent (102 mg) at room temperature. The mixture was warmed to 100° C. and refluxed for 12 h under the protection of nitrogen gas, and then concentrated under reduced pressure. Silica gel was directly added thereto to obtain the sample, which was purified by silica gel column chromatography to afford the title compound (95 mg), which was directly used in a next step.

Step B: 2-amino-5-(2-(2,5-difluorophenyl)pyrrolidin-1-yl)pyrazolo[1,5-a]pyrimidine-3-thioamide

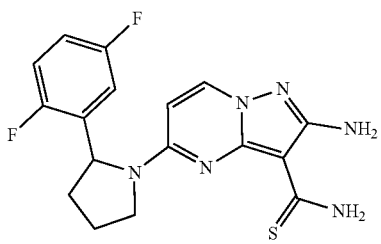 [SMILES: NC(=S)c1c(N)nn2ccc(N3CCCC3c3cc(F)ccc3F)nc12]

Referring to the experimental procedure in step B of Example 27, 5-(2-(2,5-difluorophenyl)pyrrolidin-1-yl)-N-(4-methoxybenzyl)-3-(4-methyloxazol-2-yl)pyrazolo[1,5-a]pyrimidin-2-amine was replaced with 5-(2-(2,5-difluorophenyl)pyrrolidin-1-yl)-2-(4-methoxybenzylamino)pyrazolo[1,5-a]pyrimidine-3-thiocarboxamide (30 mg) to afford the title compound (14 mg).

$^1$H NMR (400 MHz, CDCl$_3$) δ 9.64-9.38 (m, 0.4H), 8.75 (brs, 0.6H), 8.17-7.92 (m, 1H), 7.10-6.81 (m, 3H), 6.75-6.03

(m, 3H), 5.80-5.63 (m, 0.5H), 5.57-5.40 (m, 1H), 5.25-5.09 (m, 0.5H), 4.02-3.79 (m, 2H), 2.53 (m, 1H), 2.42-2.96 (m, 3H). m/z=375[M+1]⁺.

Example 32 (R)-3-bromo-5-(2-(2,5-difluorophenyl)pyrrolidin-1-yl)pyrazolo[1,5-c]pyrimidin-2-amine

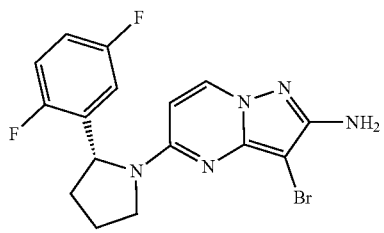 [SMILES: Nc1nn2ccc(N3CCC[C@@H]3c3cc(F)ccc3F)nc2c1Br]

To a solution of (R)-5-(2-(2,5-difluorophenyl)pyrrolidin-1-yl)pyrazolo[1,5-a]pyrimidin-2-amine (180 mg) in trichloromethane was slowly added NBS (122 mg) under stirring in an ice bath. After completion of the addition, the resulting mixture was reacted for 30 minutes, and then quenched with an appropriate amount of water, and extracted with dichloromethane. The combined organic phase was washed with a saturated saline solution, dried over anhydrous sodium sulfate and filtered. The filtrate was concentrated in vacuo, and the resulting residue was purified and separated by silica gel column chromatography to afford the title compound (114 mg).

¹H NMR (400 MHz, CDCl₃) δ 7.85 (d, J=7.0 Hz, 1H), 7.05-7.00 (m, 1H), 6.92-6.88 (m, 1H), 6.78-6.74 (m, 1H), 5.70 (brs, 1H), 5.30 (brs, 1H), 4.20-3.68 (m, 4H), 2.47 (m, 1H), 2.06-2.02 (m, 3H). m/z=394[M+1]⁺.

Example 33 5-(2-(2,5-difluorophenyl)pyrrolidin-1-yl)-3-(3-morpholinylphenyl)pyrazolo[1,5-a]pyrimidin-2-amine

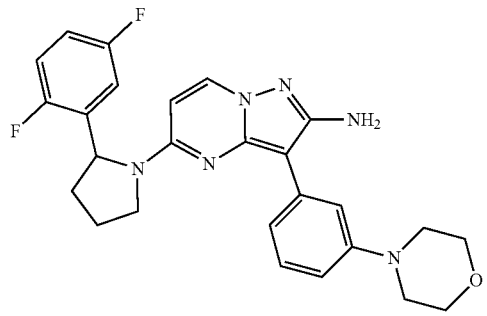 [SMILES: Nc1nn2ccc(N3CCCC3c3cc(F)ccc3F)nc2c1-c1cccc(N2CCOCC2)c1]

Step A: 5-(2-(2,5-difluorophenyl)pyrrolidin-1-yl)pyrazolo[1,5-c]pyrimidin-2-amine

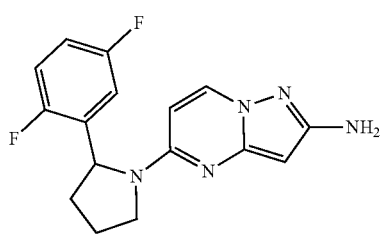 [SMILES: Nc1cc2nc(N3CCCC3c3cc(F)ccc3F)ccn2n1]

Referring to Example 9, (R)-2-(2,5-difluorophenyl)pyrrolidine was replaced with 2-(2,5-difluorophenyl)pyrrolidine to afford ethyl 2-acetylamino-5-(2-(2,5-difluoro phenyl)pyrrolidin-1-yl)pyrazolo[1,5-a]pyrimidine-3-carboxylate. Ethyl 2-acetylamino-5-(2-(2,5-difluorophenyl)pyrrolidin-1-yl)pyrazolo[1,5-a]pyrimidine-3-carboxylate (822 mg) was added to 48% of concentrated sulfuric acid under stirring in an ice bath. After completion of the addition, the resulting mixture was warmed to 100° C. and reacted for 6 h, and then cooled to room temperature. The reaction solution was poured into an ice, adjusted to about pH=8 with 1N sodium hydroxide solution, and then extracted with ethyl acetate. The combined organic phase was washed with a saturated saline solution, dried over anhydrous sodium sulfate and filtered. The filtrate was concentrated in vacuo, and the residue was purified by silica gel column chromatography to afford the title compound (483 mg).

¹H NMR (400 MHz, CDCl₃) δ 7.91 (d, J=7.6 Hz, 1H), 7.07-7.01 (m, 1H), 6.92-6.88 (m, 1H), 6.75-6.70 (m, 1H), 5.69 (s, 1H), 5.47 (s, 1H), 5.25 (brs, 1H), 3.92 (m, 1H), 3.75 (m, 1H), 2.45 (m, 1H), 2.12-1.92 (m, 3H). m/z=316[M+1]⁺.

Step B: 3-bromo-5-(2-(2,5-difluorophenyl)pyrrolidin-1-yl)pyrazolo[1,5-a]pyrimidin-2-amine

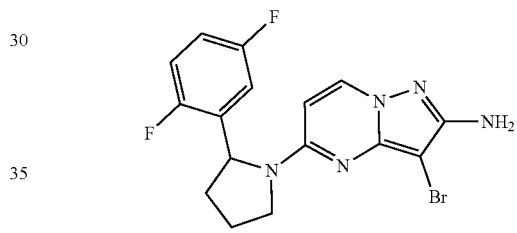

Referring to Example 32, (R)-5-(2-(2,5-difluorophenyl)pyrrolidin-1-yl)pyrazolo[1,5-a]pyrimidin-2-amine was replaced with 5-(2-(2,5-difluorophenyl)pyrrolidin-1-yl)pyrazolo[1,5-a]pyrimidin-2-amine to afford the title compound. Yield: 73%.

¹H NMR (400 MHz, CDCl₃) δ 7.85 (d, J=7.0 Hz, 1H), 7.06-7.01 (m, 1H), 6.92-6.87 (m, 1H), 6.78-6.74 (m, 1H), 5.70 (brs, 1H), 5.30 (brs, 1H), 4.21-3.68 (m, 4H), 2.46 (m, 1H), 2.06-2.01 (m, 3H). m/z=394[M+1]⁺.

Step C: 3-bromo-5-(2-(2,5-difluorophenyl)pyrrolidin-1-yl)pyrazolo[1,5-a]pyrimidine-2-tert-butoxycarbonylamino

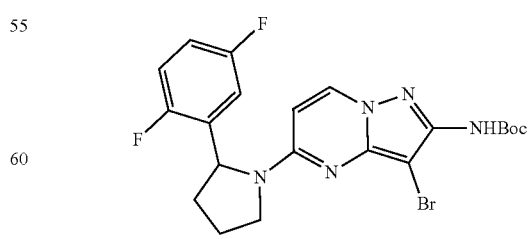

To a solution of 3-bromo-5-(2-(2,5-difluorophenyl)pyrrolidin-1-yl)pyrazolo[1,5-a]pyrimidin-2-amine (440 mg) and triethylamine (932 μL) in dichloromethane was slowly added (Boc)₂O (1.07 mL) dropwise under stirring in an ice bath, and then DMAP (13.6 mg) was added thereto. After completion of the addition, the resulting mixture was warmed to room temperature and reacted for 3 h, and then an appropriate amount of water was added thereto. The mixture was then extracted with dichloromethane. The combined organic phase was washed with a saturated saline solution, dried over anhydrous sodium sulfate and filtered. The filtrate was concentrated in vacuo, and the residue was separated by silica gel column chromatography to afford the title compound (379 mg).

m/z=494[M+1]⁺.

Step D: 5-(2-(2,5-difluorophenyl)pyrrolidin-1-yl)-3-(3-morpholinylphenyl)pyrazolo[1,5-a]pyrimidin-2-amine

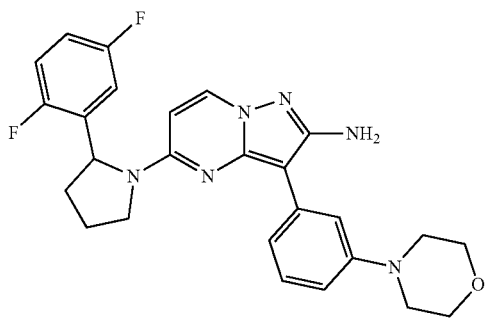 [SMILES: Nc1nn2ccc(N3CCCC3c3cc(F)ccc3F)nc2c1-c1cccc(N2CCOCC2)c1]

To a solution of 3-bromo-5-(2-(2,5-difluorophenyl)pyrrolidin-1-yl)pyrazolo[1,5-a]pyrimidine-2-tert-butoxycarbonylamino (30 mg) in a mixture of DME/water (V/V=1/1) were added (3-morpholinylphenyl)boronic acid (15 mg), potassium phosphate (26 mg) and tetra(triphenylphosphine) palladium (1.4 mg) in a sealed-tube reaction. The reaction mixture was purged with nitrogen gas, warmed to 110° C. and reacted overnight. Then, an appropriate amount of water was added thereto, and the resulting mixture was extracted with ethyl acetate. The combined organic phase was washed with a saturated saline solution, dried over anhydrous sodium sulfate and filtered. The filtrate was concentrated in vacuo, and the residue was purified and separated by thin layer chromatography to afford the title compound (1.52 mg).

¹H NMR (400 MHz, CDCl₃) δ 8.22 (brs, 1H), 7.05 (m, 2H), 6.91-6.89 (m, 2H), 6.77-6.75 (m, 2H), 5.83 (brs, 1H), 5.33 (brs, 1H), 4.53-4.14 (m, 2H), 4.00-3.63 (m, 5H), 3.19 (m, 4H), 2.44 (m, 1H), 2.08-2.01 (m, 3H). m/z=477[M+1]⁺.

Example 34 (R)-5-(2-(2,5-difluorophenyl)pyrrolidin-1-yl)-3-(1-methyl-1H-pyrazol-4-yl)pyrazolo[1,5-c]pyrimidin-2-amine

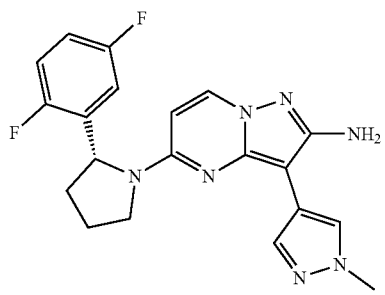 [SMILES: Cn1cc(-c2c(N)nn3ccc(N4CCC[C@@H]4c4cc(F)ccc4F)nc23)cn1]

Step A: (R)-3-bromo-5-(2-(2,5-difluorophenyl)pyrrolidin-1-yl)pyrazolo[1,5-a]pyrimidine-2-tert-butoxycarbonylamino

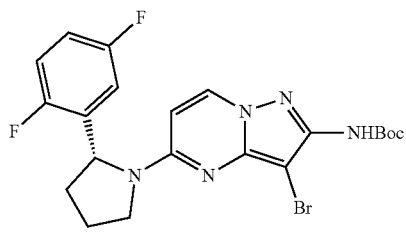 [SMILES: CC(C)(C)OC(=O)Nc1nn2ccc(N3CCC[C@@H]3c3cc(F)ccc3F)nc2c1Br]

Referring to Step C in Example 33, 3-bromo-5-(2-(2,5-difluorophenyl)pyrrolidin-1-yl)pyrazolo[1,5-c]pyrimidin-2-amine was replaced with (R)-3-bromo-5-(2-(2,5-difluorophenyl)pyrrolidin-1-yl)pyrazolo[1,5-c]pyrimidin-2-amine to afford the title compound. Yield: 56%.

m/z=494[M+1]⁺.

Step B: (R)-5-(2-(2,5-difluorophenyl)pyrrolidin-1-yl)-3-(1-methyl-1H-pyrazol-4-yl)pyrazolo[1,5-a]pyrimidine-2-tert-butoxycarbonylamino

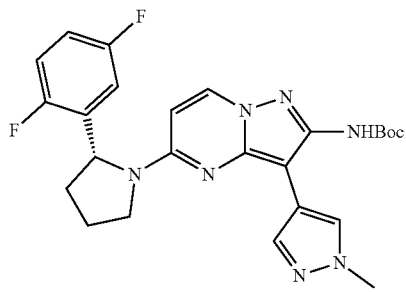 [SMILES: Cn1cc(-c2c(NC(=O)OC(C)(C)C)nn3ccc(N4CCC[C@@H]4c4cc(F)ccc4F)nc23)cn1]

To a solution of (R)-3-bromo-5-(2-(2,5-difluorophenyl)pyrrolidin-1-yl)pyrazolo[1,5-c]pyrimidine-2-tert-butoxycarbonylamino (40 mg) in a mixture of 1,4-dioxane/water (V/V=4/1) were added 1-methyl-4-pyrazole boronic acid pinacol ester (25 mg) potassium carbonate (22 mg) and tetra(triphenylphosphine) palladium (4.6 mg) in a microwave reaction. The reaction mixture was purged with nitrogen gas, and reacted under microwave at 120° C. for 1 h. Then, an appropriate amount of water was added thereto, and the resulting mixture was extracted with ethyl acetate. The combined organic phase was washed with a saturated saline solution, dried over anhydrous sodium sulfate and filtered. The filtrate was concentrated in vacuo, and the residue was purified and separated by thin layer chromatography to afford the title compound (30 mg).

m/z=496[M+1]⁺.

Step C: (R)-5-(2-(2,5-difluorophenyl)pyrrolidin-1-yl)-3-(1-methyl-1H-pyrazol-4-yl)pyrazolo[1,5-a]pyrimidin-2-amine

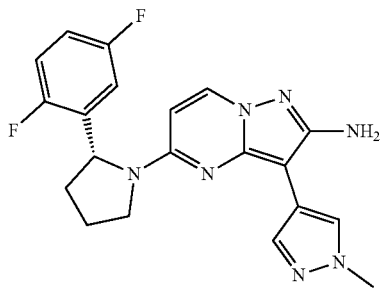 [SMILES: Cn1cc(-c2c(N)nn3ccc(N4CCC[C@@H]4c4cc(F)ccc4F)nc23)cn1]

To a solution of (R)-5-(2-(2,5-difluorophenyl)pyrrolidin-1-yl)-3-(1-methyl-1H-pyrazol-4-yl)pyrazolo[1,5-c]pyrimidine-2-tert-butoxycarbonylamino (30 mg) in dichloromethane was slowly added trifluoroacetic acid (1 mL) dropwise under stirring in an ice bath. After completion of the dropwise addition, the mixture was warmed to room temperature and reacted for 3 h. The solvent and trifluoroacetic acid were removed by distillation under reduced pressure. After addition of an appropriate amount of water, the resulting mixture was adjusted to about pH=8 with a saturated sodium carbonate solution, and then extracted with ethyl acetate. The combined organic phase was washed with a saturated saline solution, dried over anhydrous sodium sulfate and filtered. The filtrate was concentrated in vacuo, and the residue was purified and separated by thin layer chromatography to afford the title compound (14 mg).

$^1$H NMR (400 MHz, CDCl$_3$) δ 8.11 (s, 1H), 7.12-7.05 (m, 1H), 6.94-6.92 (m, 1H), 6.80-6.75 (m, 1H), 5.96 (brs, 1H), 5.55 (brs, 1H), 4.28 (brs, 2H), 4.02-3.63 (m, 5H), 2.59-2.41 (m, 1H), 2.11-2.05 (m, 3H). m/z=396[M+1]$^+$.

Example 35 ethyl 2-amino-5-((2R,4S)-2-(2,5-difluorophenyl)-4-fluoropyrrolidin-1-yl)pyrazolo[1,5-a]pyrimidine-3-carboxylate

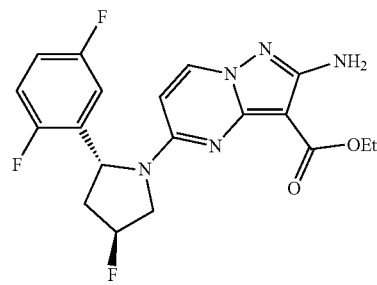

(2R,4S)-2-(2,5-difluorophenyl)-4-fluoropyrrolidine (108 mg), ethyl 2-amino-5-chloropyrazolo[1,5-a]pyrimidine-3-carboxylate (155 mg) and N,N-diisopropylethylamine (129 mg) were dissolved in n-butanol, and reacted at 160° C. overnight in a sealed tube. After monitoring the completion of the reaction, the solvent was removed. The resulting residue was purified by silica gel column chromatography (V/V:PE/EA=3/1) to afford the title compound (142 mg).

$^1$H NMR (400 MHz, CDCl$_3$) δ 7.98-7.84 (m, 1H), 7.04-6.94 (m, 3H), 5.70-5.90 (m, 1H), 5.24-5.50 (m, 4H), 4.85-4.45 (m, 1H), 4.42-4.21 (m, 2H), 4.11-3.93 (m, 1H), 2.85-3.10 (m, 1H), 2.04-2.30 (m, 1H), 1.40 (m, 3H). m/z=406 [M+1]$^+$.

Example 36 2-amino-5-((2R,4S)-2-(2,5-difluorophenyl)-4-fluoropyrrolidin-1-yl)pyrazolo[1,5-a]pyrimidine-3-carboxamide

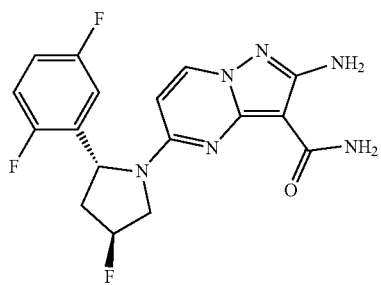 [SMILES: NC(=O)c1c(N)nn2ccc(N3C[C@@H](F)C[C@@H]3c3cc(F)ccc3F)nc12]

To a solution of ethyl 2-amino-5-((2R,4S)-2-(2,5-difluorophenyl)-4-fluoro pyrrolidin-1-yl)pyrazolo[1,5-a]pyrimidine-3-carboxylate (142 mg) in n-butanol were added aqueous ammonia (2 mL), a small amount of ammonium chloride and a catalytic amount of tetrabutylammonium iodide, and the reaction mixture was stirred at 160° C. for 30 h in a sealed tube made of iron. Then, the solvent was removed, and the resulting residue was purified by silica gel column chromatography (V/V:PE/EA=1.5/1) to afford the title compound (25 mg).

$^1$H NMR (400 MHz, CDCl$_3$) δ 8.23 (d, J=12.8 Hz, 1H), 8.02 (d, J=6.4 Hz, 1H), 7.02-7.08 (m, 1H), 6.92-6.96 (m, 1H), 6.82-6.86 (m, 1H), 5.93 (brs, 1H), 5.70-5.20 (m, 5H), 4.35-4.10 (m, 1H), 4.09-3.97 (m, 1H), 3.02-2.93 (m, 1H), 2.28-2.10 (m, 1H). m/z=377[M+1]$^+$.

Example 37 ethyl 2-amino-5-((2S,4S)-2-(2,5-difluorophenyl)-4-fluoropyrrolidin-1-yl)pyrazolo[1,5-a]pyrimidine-3-carboxylate

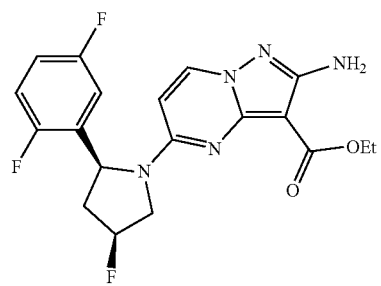 [SMILES: CCOC(=O)c1c(N)nn2ccc(N3C[C@@H](F)C[C@H]3c3cc(F)ccc3F)nc12]

Referring to Example 35, (2R,4S)-2-(2,5-difluorophenyl)-4-fluoropyrrolidine (Compound I3) was replaced with (2S,4S)-2-(2,5-difluorophenyl)-4-fluoropyrrolidine (Compound I4) to afford the title compound (70 mg).

1H NMR (400 MHz, CDCl3) δ 8.02-7.98 (m, 1H), 7.14-6.72 (m, 3H), 5.83 (m, 1H), 5.55-5.20 (m, 4H), 4.40-4.28 (m, 3H), 4.15-3.95 (m, 1H), 2.80-2.60 (m, 1H), 2.56-2.47 (m, 1H), 1.30-1.45 (m, 3H). m/z=406 [M+1]+.

Example 38 ethyl 2-amino-5-(2-(2,5-difluorophenyl)-4,4-difluoropyrrolidin-1-yl)pyrazolo[1,5-a]pyrimidine-3-carboxylate

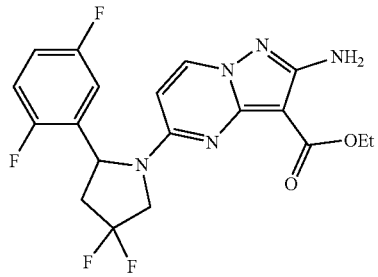 [SMILES: CCOC(=O)c1c(N)nn2ccc(N3CC(F)(F)CC3c3cc(F)ccc3F)nc12]

Referring to Example 35, (2R,4S)-2-(2,5-difluorophenyl)-4-fluoropyrrolidine (Compound I3) was replaced with 2-(2,5-difluorophenyl)-4,4-difluoropyrrolidine (Intermediate 15) to afford the title compound (1.3 mg). $^1$H NMR (400 MHz, CDCl$_3$) δ 8.15-7.98 (m, 1H), 7.14-6.85 (m, 3H), 5.83-5.79 (m, 1H), 5.58-5.20 (m, 3H), 4.45-4.20 (m, 4H), 3.20-3.00 (m, 1H), 2.65-2.45 (m, 1H), 1.30-1.45 (m, 3H). m/z=424[M+1]$^+$.

Example 39 2-amino-5-((2R,4S)-2-(2,5-difluorophenyl)-4-fluoropyrrolidin-1-yl)-N-methylpyrazolo[1,5-a]pyrimidine-3-carboxamide

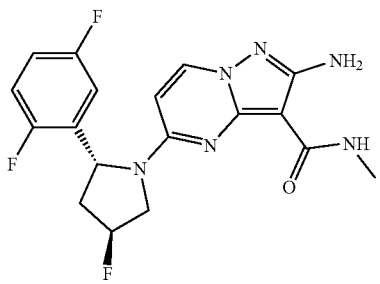 [SMILES: CNC(=O)c1c(N)nn2ccc(N3C[C@@H](F)C[C@@H]3c3cc(F)ccc3F)nc12]

Ethyl 2-amino-5-((2R,4S)-2-(2,5-difluorophenyl)-4-fluoropyrrolidin-1-yl)pyrazolo[1,5-a]pyrimidine-3-carboxylate (50 mg) was placed in a sealed tube reactor, and then a solution of methylamine in methanol (2 mL) was added and stirred at 100° C. for 40 h. The solvent was removed by evaporation under reduced pressure, and the resulting residue was purified by thin layer chromatography (EA) to afford the title compound (30 mg).

$^1$H NMR (400 MHz, CDCl$_3$) δ 8.04 (d, J=6.0 Hz, 1H), 7.10-6.81 (m, 3H), 6.10-5.80 (m, 1H), 5.70-5.20 (m, 4H), 4.40-3.90 (m, 2H), 3.02-2.93 (m, 5H), 2.23-2.04 (m, 1H). m/z=391[M+1]$^+$.

Example 40 (R)-2-amino-5-(2-(2,5-difluorophenyl)pyrrolidin-1-yl)-N-(2-hydroxyethoxy)pyrazolo[1,5-c]pyrimidine-3-carboxamide

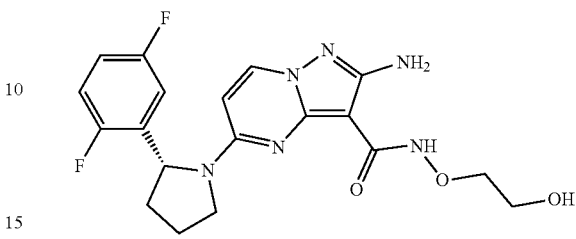

Referring to Example 3, methylamine hydrochloride was replaced with 1-[2-(aminooxy)ethoxy]ethylene, and the resulting mixture was washed with 1 N hydrochloric acid solution during extraction, and finally separated by thin layer chromatography to afford the title compound.

$^1$H NMR (400 MHz, CDCl$_3$) δ 9.36 (s, 1H), 8.11 (s, 1H), 7.11-7.05 (m, 1H), 6.97-6.93 (m, 1H), 6.75-6.72 (m, 1H), 6.15 (brs, 1H), 5.54 (brs, 1H), 5.33 (s, 2H), 4.01-3.81 (m, 7H), 2.53 (m, 1H), 2.30-1.99 (m, 3H). m/z=419[M+1]$^+$.

Example 41 2-amino-5-((2R,4S)-2-(2,5-difluorophenyl)-4-fluoropyrrolidin-1-yl)pyrazolo[1,5-c]pyrimidine-3-carbonitrile

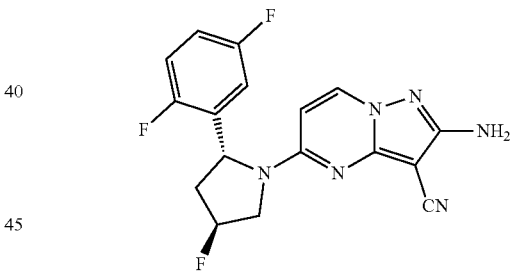

To a solution of 2-amino-5-((2R,4S)-2-(2,5-difluorophenyl)-4-fluoropyrrolidin-1-yl)pyrazolo[1,5-c]pyrimidine-3-carboxamide (45 mg) and triethylamine (100 μL) in dichloromethane (10 mL) was added a solution of trifluoroacetic anhydride (63 mg) in dichloromethane (2 mL) dropwise under stirring in an ice bath. The reaction mixture was reacted in an ice bath for 1 hour, and then quenched with a saturated sodium carbonate solution, extracted with dichloromethane, and then purified and separated by silica gel column chromatography to afford the title compound (22 mg).

$^1$H NMR (400 MHz, DMSO-d$_6$) δ 8.35 (s, 1H), 7.24-7.12 (m, 3H), 6.40 (brs, 0.5H), 6.10 (s, 2H), 5.91 (brs, 0.5H), 5.51 (d, J=52.4 Hz, 1H), 5.36 (m, 1H), 4.11-4.01 (m, 2H), 2.89-2.80 (m, 1H), 2.30-2.19 (m, 1H). m/z=359[M+1]$^+$.

Example 42 ethyl 2-amino-5-((4R)-2-(2,5-difluorophenyl)-4-hydroxypyrrolidin-1-yl)pyrazolo[1,5-c]pyrimidine-3-carboxylate

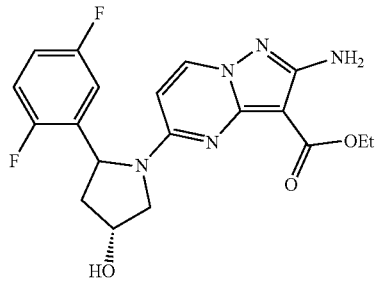 [SMILES: CCOC(=O)c1c(N)nn2ccc(N3C[C@H](O)CC3c3cc(F)ccc3F)nc12]

Referring to Step E of Example 1, (R)-2-(2,5-difluorophenyl)pyrrolidine was replaced with (3R)-5-(2,5-difluorophenyl)-3-hydroxypyrrolidine (Compound I6) to afford the title compound (yield: 66%).

$^1$H NMR (400 MHz, CDCl$_3$) δ 7.97 (s, 0.5H), 7.88 (d, J=7.4 Hz, 0.5H), 7.08-7.02 (m, 1.5H), 6.97-6.83 (m, 1.5H), 5.80 (d, J=7.2 Hz, 1H), 5.41 (m, 1H), 5.26 (s, 2H), 4.70 (d, J=17.8 Hz, 1H), 4.46-4.28 (m, 2H), 4.17-3.97 (m, 2H), 2.81-2.62 (m, 1H), 2.47 (brs, 0.5H), 2.25-2.15 (m, 1H), 1.76 (brs, 0.5H), 1.40 (t, J=7.0 Hz, 3H). m/z=404 [M+1]$^+$.

Example 43 ethyl 2-amino-5-(2-(2,5-difluorophenyl)-4-oxopyrrolidin-1-yl)pyrazolo[1,5-a]pyrimidine-3-carboxylate

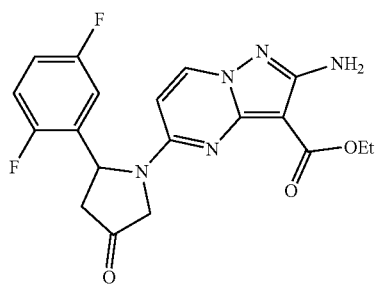

Referring to Step E of Example 1, (R)-2-(2,5-difluorophenyl)pyrrolidine was replaced with 5-(2,5-difluorophenyl)-pyrrolidin-3-one (Compound I7) to afford the title compound (yield: 4%).

$^1$H NMR (400 MHz, CDCl$_3$) δ 8.11 (d, J=7.4 Hz, 1H), 7.29-7.27 (m, 1H), 7.12-6.86 (m, 2H), 5.99 (d, J=7.4 Hz, 1H), 5.90 (m, 1H), 5.42 (s, 2H), 4.43 (q, J=7.0 Hz, 2H), 4.31-4.07 (m, 2H), 3.31 (dd, J=18.6, 10.6 Hz, 1H), 2.79 (d, J=18.6 Hz, 1H), 1.46 (t, J=7.0 Hz, 3H). m/z=402 [M+1]$^+$.

Example 44 2-amino-5-((2R,4S)-2-(2,5-difluorophenyl)-4-hydroxypyrrolidin-1-yl)pyrazolo[1,5-a]pyrimidine-3-carbonitrile

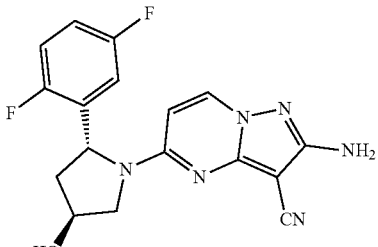

Step A: tert-butyl (2R,4S)-2-(2,5-difluorophenyl)-4-(4-nitrobenzoyloxy) pyrrolidine-1-carboxylate

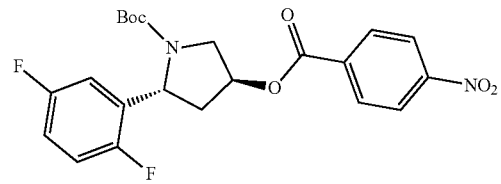 [SMILES: CC(C)(C)OC(=O)N1C[C@@H](OC(=O)c2ccc([N+](=O)[O-])cc2)C[C@@H]1c1cc(F)ccc1F]

To a solution of triphenylphosphine (4.55 g) in tetrahydrofuran (40 mL) was added diisopropyl azodicarboxylate (3.51 g) dropwise under stirring in an ice bath. Then the mixture was stirred at room temperature for about 30 minutes, and a large amount of solid was precipitated. To the reaction solution were sequentially added p-nitrobenzoic acid (2.66 g), and tert-butyl (4R)-2-(2,5-difluorophenyl)-4-hydroxy pyrrolidine-1-carboxylate (4.33 g, which was prepared by the step E in Example 3) dropwise. The resulting mixture was reacted at room temperature for 3 hours, quenched with water, extracted with dichloromethane, and then purified and separated by silica gel column chromatography to afford the title compound (2.84 g).

$^1$H NMR (400 MHz, CDCl$_3$) δ 8.35 (d, J=2.0 Hz, 2H), 8.23 (d, J=2.0 Hz, 2H), 7.08-6.89 (m, 3H), 5.59 (s, 1H), 5.38-5.12 (m, 1H), 4.15-3.83 (m, 2H), 2.74 (q, J=8.0 Hz, 1H), 2.33-2.18 (m, 1H), 1.53-1.15 (m, 9H). m/z=449[M+1]$^+$.

Step B: (3S,5R)-5-(2,5-difluorophenyl)pyrrolidin-3-yl-4-nitrobenzoate hydrochloride

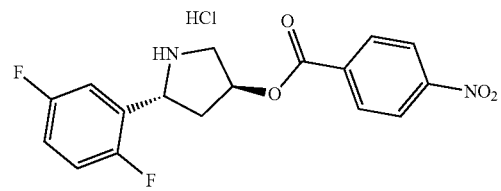 [SMILES: Cl ; O=C(O[C@@H]1CN[C@@H](c2cc(F)ccc2F)C1)c1ccc([N+](=O)[O-])cc1]

To a solution of tert-butyl (2R,4S)-2-(2,5-difluorophenyl)-4-(4-nitrobenzoyloxy) pyrrolidine-1-carboxylate (0.74 g) in dioxane (3 mL) was added a concentrated hydrochloric acid (0.7 mL) dropwise under stirring in an ice bath, and then heated to 80° C. and reacted for 20 min under stirring. The resulting mixture was concentrated to remove the solvent, and the resulting crude product (0.64 g) was directly used in a next step.

$^1$H NMR (400 MHz, DMSO-d$_6$) δ 10.71 (brs, 1H), 9.75 (brs, 1H), 8.38-8.35 (m, 4H), 7.70-7.60 (m, 1H), 7.44-7.33 (m, 2H), 5.73 (t, J=4.0 Hz, 1H), 5.13 (q, J=6.4 Hz, 1H), 3.84 (dd, J=4.0, 8.0 Hz, 1H), 3.60 (d, J=12 Hz, 1H), 2.80-2.60 (m, 2H). m/z=349[M+1]$^+$.

Step C: (3S,5R)-1-(2-amino-3-cyanopyrazolo[1,5-c]pyrimidin-5-yl)-5-(2,5-difluorophenyl)pyrrolidin-3-yl-4-nitrobenzoate

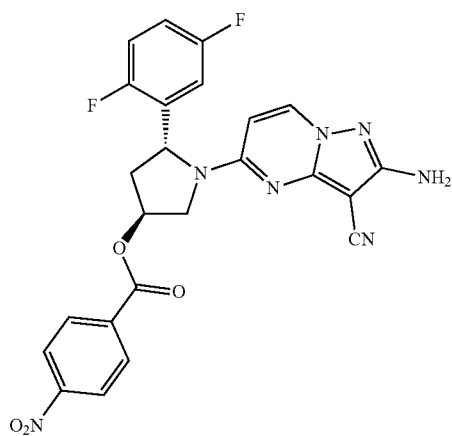 [SMILES: N#Cc1c(N)nn2ccc(N3C[C@@H](OC(=O)c4ccc([N+](=O)[O-])cc4)C[C@@H]3c3cc(F)ccc3F)nc12]

(3S,5R)-5-(2,5-difluorophenyl)pyrrolidin-3-yl-4-nitrobenzoate hydrochloride (0.64 g), diisopropylethylamine (1.1 g) and N,N-dimethylformamide (5 ml) were added to a 100 mL of dried single-necked bottle, and stirred at room temperature for 10 min. Then, benzotriazole-1-tris(trimethylamino)-trifluorophosphate (0.88 g) was added thereto, and the reaction system changed from turbid to transparent. Thereto was added 2-amino-5-oxo-4,5-dihydropyrazolo[1,5-c]pyrimidine-3-carbonitrile (0.35 g, which was prepared with reference to the step C of Example 1 by replacing ethyl 3,5-diamino-1H-pyrazole-4-carboxylate with 3,5-diamino-1H-pyrazole-4-carbonitrile). The above solution was maintained at 100° C. and reacted for 2 h. The solvent was removed by distillation under reduced pressure, and the residue was dissolved with dichloromethane, and then purified and separated by silica gel column chromatography to afford the title compound (0.59 g)

$^1$H NMR (400 MHz, CDCl$_3$) δ 8.30 (d, J=4.0 Hz, 2H), 8.20 (d, J=4.0 Hz, 2H), 7.93 (d, J=8.0 Hz, 1H), 7.14-6.84 (m, 3H), 6.00-5.30 (m, 3H), 4.45 (brs, 3H), 4.24 (dd, J=4, 12 Hz, 1H), 3.00-2.85 (m, 1H), 2.56-2.44 (m, 1H). m/z=506[M+1]$^+$.

Step D: 2-amino-5-((2R,4S)-2-(2,5-difluorophenyl)-4-hydroxypyrrolidin-1-yl)pyrazolo[1,5-c]pyrimidine-3-carbonitrile

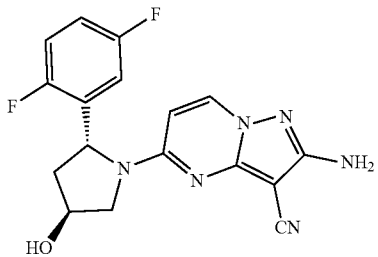 [SMILES: N#Cc1c(N)nn2ccc(N3C[C@@H](O)C[C@@H]3c3cc(F)ccc3F)nc12]

To a solution of (3S,5R)-1-(2-amino-3-cyanopyrazolo[1,5-c]pyrimidine-5-yl)-5-(2,5-difluorophenyl)pyrrolidin-3-yl-4-nitrobenzoate (0.51 g) in methanol (3 mL) was added 4N sodium hydroxide solution (1.5 mL) dropwise under stirring in an ice bath, and then stirred at room temperature for about 1 hour. The resulting mixture was made neutral with 4N hydrochloric acid in an ice bath, extracted with dichloromethane, and then purified and separated by silica gel column chromatography to afford the title compound (0.32 g).

$^1$H NMR (400 MHz, DMSO-d$_6$) δ 8.40-8.16 (m, 1H), 7.35-6.95 (m, 3H), 6.18-5.92 (m, 2H), 5.78 (brs, 1H), 5.42-5.12 (m, 2H), 4.50-4.35 (m, 1H), 4.02-3.80 (m, 1.5H), 3.45 (brs, 0.5H), 2.43-2.28 (m, 1H), 2.08-1.93 (m, 1H). m/z=357[M+1]$^+$.

Example 45 2-amino-5-((2R,4S)-2-(2,5-difluorophenyl)-4-hydroxypyrrolidin-1-yl)pyrazolo[1,5-c]pyrimidine-3-carboxamide

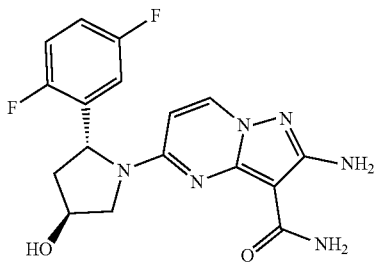

Step A: (3S,5R)-1-(2-amino-3-carbamoyl-pyrazolo[1,5-c]pyrimidin-5-yl)-5-(2,5-difluorophenyl)pyrrolidin-3-yl-4-nitrobenzoate

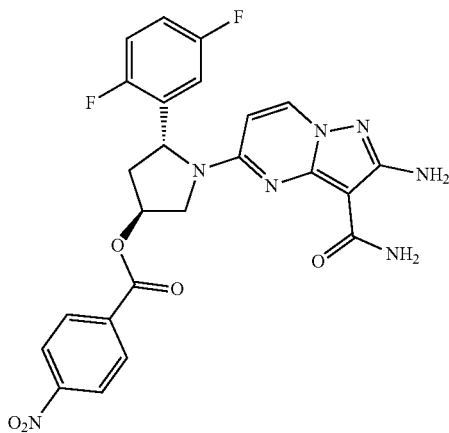 [SMILES: NC(=O)c1c(N)nn2ccc(N3C[C@@H](OC(=O)c4ccc([N+](=O)[O-])cc4)C[C@@H]3c3cc(F)ccc3F)nc12]

The title compound (50 mg) obtained in the step C of Example 44 was suspended in 98% of concentrated sulfuric acid (1.5 mL), stirred and reacted at room temperature for 1 hour. The reaction solution was poured into an ice water, and the pH of the system was adjusted to be weakly basic with a 4N sodium hydroxide solution. The resulting mixture was then extracted with dichloromethane, dried and filtered, and the filtrate was concentrated to afford a crude product (43 mg), which was directly used in a next step. m/z=524[M+1]$^+$.

Step B: 2-amino-5-((2R,4S)-2-(2,5-difluorophenyl)-4-hydroxypyrrolidin-1-yl)pyrazolo[1,5-c]pyrimidine-3-carboxamide

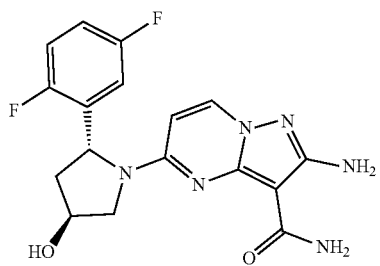 [SMILES: NC(=O)c1c(N)nn2ccc(N3C[C@@H](O)C[C@@H]3c3cc(F)ccc3F)nc12]

Referring to the step D of Example 44, (3S,5R)-1-(2-amino-3-cyanopyrazolo[1,5-a]pyrimidin-5-yl)-5-(2,5-difluorophenyl)pyrrolidin-3-yl-4-nitrobenzoate was replaced with (3S,5R)-1-(2-amino-3-carbamoyl-pyrazolo[1,5-c]pyrimidin-5-yl)-5-(2,5-difluorophenyl)pyrrolidin-3-yl-4-nitrobenzoate to afford the title compound (yield: 66%).

$^1$H NMR (400 MHz, CD$_3$OD) δ 8.18-7.95 (m, 1H), 7.12-6.80 (m, 3H), 6.38-6.20 (m, 1H), 5.48-5.37 (m, 1H), 4.58-4.45 (m, 1H), 4.02-3.85 (m, 1H), 3.70-3.55 (m, 1H), 2.55-2.24 (m, 1H), 2.11-1.98 (m, 1H). m/z=375[M+1]$^+$.

Example 46 2-amino-5-((2S,4S)-2-(2,5-difluorophenyl)-4-hydroxypyrrolidin-1-yl)pyrazolo[1,5-c]pyrimidine-3-carbonitrile

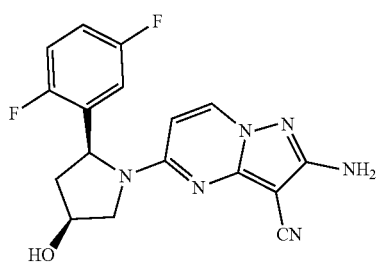 [SMILES: N#Cc1c(N)nn2ccc(N3C[C@@H](O)C[C@H]3c3cc(F)ccc3F)nc12]

Step A: (3S,5S)-5-(2,5-difluorophenyl)pyrrolidin-3-yl-4-nitrobenzoate Hydrochloride

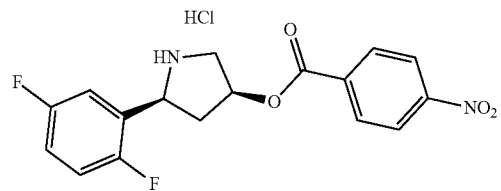 [SMILES: Cl ; O=C(O[C@@H]1CN[C@H](c2cc(F)ccc2F)C1)c1ccc([N+](=O)[O-])cc1]

Referring to the step B of Example 44, tert-butyl (2R,4S)-2-(2,5-difluorophenyl)-4-(4-nitrobenzoyloxy)pyrrolidine-1-carboxylate was replaced with tert-butyl (2S,4S)-2-(2,5-difluorophenyl)-4-(4-nitrobenzoyloxy)pyrrolidine-1-carboxylate (which was obtained in the step A of Example 44) to afford the title compound (yield: 100%).

$^1$H NMR (400 MHz, DMSO-d$_6$) δ 10.71 (brs, 1H), 10.10 (brs, 1H), 8.38-8.35 (m, 4H), 7.780-7.69 (m, 1H), 7.44-7.35 (m, 2H), 5.75 (s, 1H), 5.04 (t, J=8.0 Hz, 1H), 3.88-3.65 (m, 2H), 3.02-2.95 (m, 1H), 2.51-2.38 (m, 1H). m/z=349[M+1]$^+$.

Step B: (3S,5S)-1-(2-amino-3-cyanopyrazolo[1,5-c]pyrimidin-5-yl)-5-(2,5-difluorophenyl)pyrrolidin-3-yl-4-nitrobenzoate

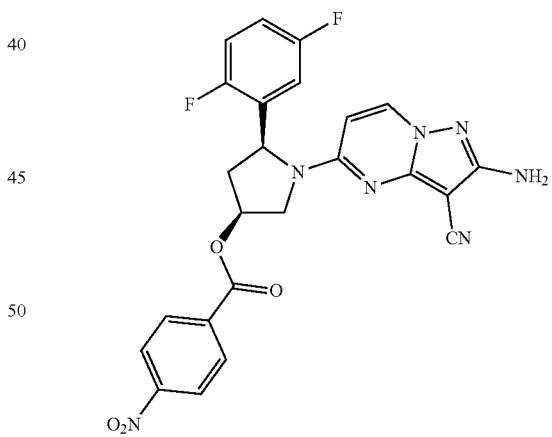

Referring to the step C of Example 44, (3S,5R)-5-(2,5-difluorophenyl)pyrrolidin-3-yl-4-nitrobenzoate hydrochloride was replaced with (3S,5S)-5-(2,5-difluorophenyl) pyrrolidin-3-yl-4-nitrobenzoate hydrochloride to afford a crude product of the title compound (yield: 60%), which was directly used in a next step. m/z=506 [M+1]$^+$.

Step C: 2-amino-5-((2S,4S)-2-(2,5-difluorophenyl)-4-hydroxypyrrolidin-1-yl)pyrazolo[1,5-c]pyrimidine-3-carbonitrile

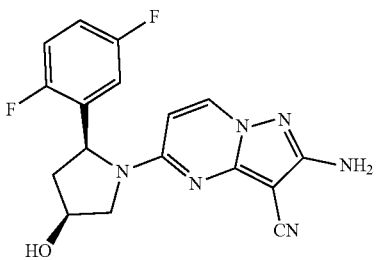 [SMILES: N#Cc1c(N)nn2ccc(N3C[C@@H](O)C[C@H]3c3cc(F)ccc3F)nc12]

Referring to the step D of Example 44, (3S,5R)-1-(2-amino-3-cyanopyrazolo[1,5-a]pyrimidin-5-yl)-5-(2,5-difluorophenyl)pyrrolidin-3-yl-4-nitrobenzoate was replaced with (3S,5S)-1-(2-amino-3-cyanopyrazolo[1,5-a]pyrimidin-5-yl)-5-(2,5-difluorophenyl)pyrrolidin-3-yl-4-nitrobenzoate to afford the title compound (yield: 70%).

$^1$H NMR (400 MHz, CD$_3$OD) δ 8.13-7.92 (m, 1H), 7.11-6.81 (m, 3H), 6.33-5.60 (m, 1H), 5.55-5.15 (m, 1H), 4.56-4.48 (m, 1H), 3.95-3.60 (m, 2H), 2.71-2.55 (m, 1H), 2.16-1.95 (m, 1H). m/z=357[M+1]$^+$.

Example 47 2-amino-5-((2R,4S)-2-(2,5-difluorophenyl)-4-hydroxypyrrolidin-1-yl)pyrazolo[1,5-a]pyrimidine-3-carboxamide

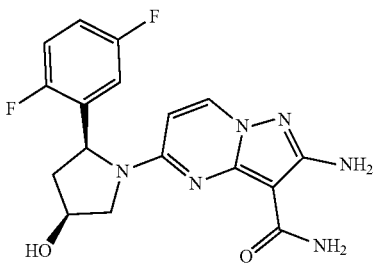 [SMILES: NC(=O)c1c(N)nn2ccc(N3C[C@@H](O)C[C@H]3c3cc(F)ccc3F)nc12]

Step A: (3S,5S)-1-(2-amino-3-carbamoyl-pyrazolo[1,5-a]pyrimidin-5-yl)-5-(2,5-difluorophenyl)pyrrolidin-3-yl-4-nitrobenzoate

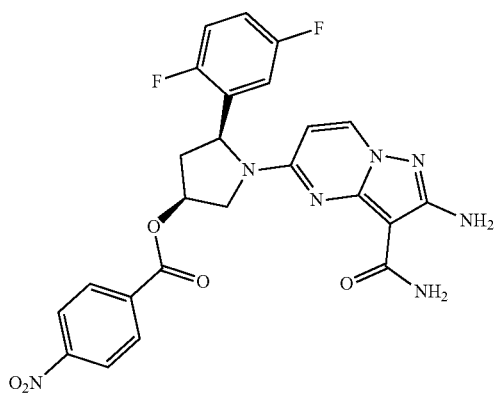 [SMILES: NC(=O)c1c(N)nn2ccc(N3C[C@@H](OC(=O)c4ccc([N+](=O)[O-])cc4)C[C@H]3c3cc(F)ccc3F)nc12]

Referring to the step A of Example 45, (3S,5R)-1-(2-amino-3-cyanopyrazolo[1,5-a]pyrimidin-5-yl)-5-(2,5-difluorophenyl)pyrrolidin-3-yl-4-nitrobenzoate was replaced with (3S,5S)-1-(2-amino-3-cyanopyrazolo[1,5-a]pyrimidin-5-yl)-5-(2,5-difluorophenyl) pyrrolidin-3-yl-4-nitrobenzoate to afford a crude product of the title compound (yield: 75%), which was directly used in the next step. m/z=524[M+1]$^+$.

Step B: 2-amino-5-((2R,4S)-2-(2,5-difluorophenyl)-4-hydroxypyrrolidin-1-yl)pyrazolo[1,5-c]pyrimidine-3-carboxamide

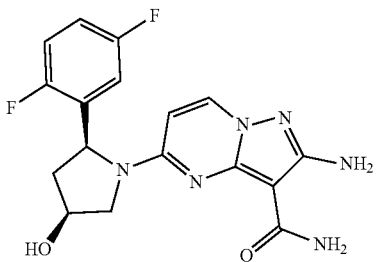

Referring to the step D of Example 44, (3S,5R)-1-(2-amino-3-carbamoyl-pyrazolo[1,5-a]pyrimidin-5-yl)-5-(2,5-difluorophenyl)pyrrolidin-3-yl-4-nitrobenzoate was replaced with (3S,5S)-1-(2-amino-3-carbamoyl-pyrazolo[1,5-c]pyrimidin-5-yl)-5-(2,5-difluorophenyl)pyrrolidin-3-yl-4-nitrobenzoate to afford the title compound (yield: 80%).

$^1$H NMR (400 MHz, CDCl$_3$) δ 8.10-7.98 (m, 1H), 7.15-6.90 (m, 3H), 6.08-5.78 (m, 1H), 5.61-4.92 (m, 5H), 4.80-4.71 (m, 1H), 4.05-3.84 (m, 2H), 2.80-2.71 (m, 1H), 2.25-2.13 (m, 1H), 1.80 (brs, 1H). m/z=375 [M+1]$^+$.

Example 48 ethyl 2-amino-5-((4S)-2-(2,5-difluorophenyl)-4-hydroxypyrrolidin-1-yl)pyrazolo[1,5-c]pyrimidine-3-carboxylate

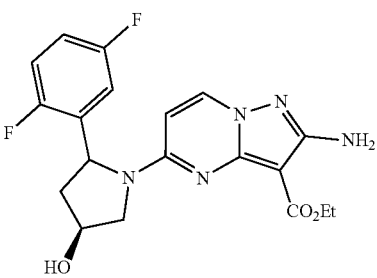 [SMILES: CCOC(=O)c1c(N)nn2ccc(N3C[C@@H](O)CC3c3cc(F)ccc3F)nc12]

Step A: ethyl 2-amino-5-((4S)-2-(2,5-difluorophenyl)-4-(4-nitrobenzoyloxy) pyrrolidin-1-yl)pyrazolo[1,5-c]pyrimidine-3-carboxylate

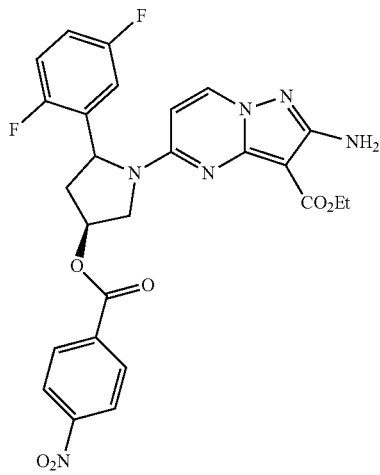 [SMILES: CCOC(=O)c1c(N)nn2ccc(N3C[C@@H](OC(=O)c4ccc([N+](=O)[O-])cc4)CC3c3cc(F)ccc3F)nc12]

To a solution of ethyl 2-amino-5-((4R)-2-(2,5-difluorophenyl)-4-hydroxypyrrolidin-1-yl)pyrazolo[1,5-c]pyrimidine-3-carboxylate (50 mg, Example 42), p-nitrobenzoic acid (41 mg) and diisopropyl azodicarboxylate (47 uL) in dichloromethane was slowly added triphenylphosphine (81 mg) under stirring in an ice bath. The reaction mixture was then warmed to room temperature and reacted overnight. The resulting mixture was concentrated by distillation under reduced pressure, and the residue was separated by silica gel column chromatography to afford the title compound (55 mg).

m/z=553[M+1]$^+$.

Step B: ethyl 2-amino-5-((4S)-2-(2,5-difluorophenyl)-4-hydroxypyrrolidin-1-yl)pyrazolo[1,5-c]pyrimidine-3-carboxylate

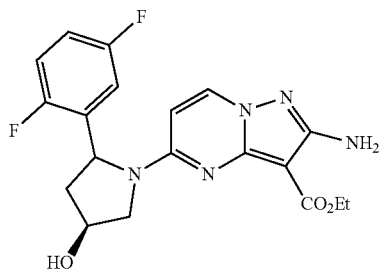 [SMILES: CCOC(=O)c1c(N)nn2ccc(N3C[C@@H](O)CC3c3cc(F)ccc3F)nc12]

To a solution of ethyl 2-amino-5-((4S)-2-(2,5-difluorophenyl)-4-(4-nitrobenzoyloxy) pyrrolidin-1-yl)pyrazolo[1,5-a]pyrimidine-3-carboxylate (200 mg) in methanol was slowly added a sodium hydroxide solution (1 N, 2 mL) dropwise under stirring in an ice bath. The reaction mixture was then warmed to room temperature and reacted for 2 hours. Then, the methanol solvent was removed by distillation under reduced pressure, and the resulting mixture was extracted with dichloromethane. The organic phase was combined, dried over anhydrous sodium sulfate, concentrated by distillation under reduced pressure, and the residue was then separated and purified by silica gel column chromatography to afford the title compound (103 mg).

$^1$H NMR (400 MHz, CDCl$_3$) δ 7.99 (s, 1H), 7.01 (m, 3H), 5.83 (brs, 1H), 5.32-5.30 (m, 3H), 4.71 (m, 1H), 4.34-4.02 (m, 4H), 2.75-2.69 (m, 1H), 2.24-2.05 (m, 1H), 1.40 (t, J=7.0 Hz, 3H). m/z=404[M+1]$^+$.

Example 49 2-amino-5-((2R,4S)-2-(2,5-difluorophenyl)-4-fluoropyrrolidin-1-yl)-N-(2-hydroxyethyl)pyrazolo[1,5-a]pyrimidine-3-carboxamide

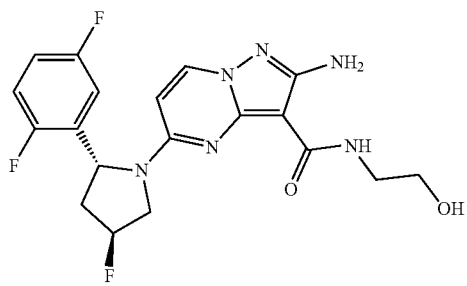 [SMILES: Nc1nn2ccc(N3C[C@@H](F)C[C@@H]3c3cc(F)ccc3F)nc2c1C(=O)NCCO]

Step A: 2-amino-5-((2R,4S)-2-(2,5-difluorophenyl)-4-fluoropyrrolidin-1-yl)pyrazolo[1,5-a]pyrimidine-3-carboxylic Acid

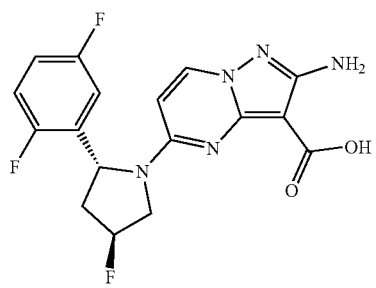 [SMILES: Nc1nn2ccc(N3C[C@@H](F)C[C@@H]3c3cc(F)ccc3F)nc2c1C(=O)O]

Referring to Example 2, the title compound (160 mg) was prepared from ethyl 2-amino-5-((2R,4S)-2-(2,5-difluorophenyl)-4-fluoropyrrolidin-1-yl)pyrazolo[1,5-a]pyrimidine-3-carboxylate (300 mg, which was prepared in Example 35).

$^1$H NMR (400 MHz, DMSO-d$_6$) δ 10.98 (brs, 1H), 8.25 (s, 1H), 7.33-6.89 (m, 3H), 6.24 (brs, 0.5H), 5.89 (s, 2H), 5.66 (brs, 0.5H), 5.39 (d, J=53.4 Hz, 1H), 5.25-5.23 (m, 1H), 4.10-4.01 (m, 2H), 2.72 (m, 1H), 2.29-1.99 (m, 1H). m/z=378[M+1]$^+$.

Step B: 2-amino-5-((2R,4S)-2-(2,5-difluorophenyl)-4-fluoropyrrolidin-1-yl)-N-(2-hydroxyethyl) pyrazolo[1,5-a]pyrimidine-3-carboxamide

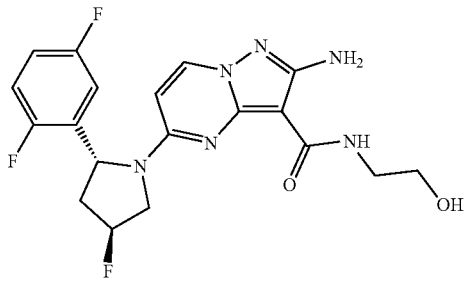 [SMILES: Nc1nn2ccc(N3C[C@@H](F)C[C@@H]3c3cc(F)ccc3F)nc2c1C(=O)NCCO]

Referring to Example 3, (R)-2-amino-5-(2-(2,5-difluorophenyl)pyrrolidin-1-yl)pyrazolo[1,5-a]pyrimidine-3-carboxylic acid was replaced with 2-amino-5-((2R,4S)-2-(2,5-difluorophenyl)-4-fluoropyrrolidin-1-yl)pyrazolo[1,5-a]pyrimidine-3-carboxylic acid (100 mg), and methylamine hydrochloride was replaced with ethanolamine (160 mg) to afford the title compound (18 mg).

$^1$H NMR (400 MHz, CDCl$_3$) δ 8.03 (s, 1H), 7.53 (brs, 1H), 7.13-6.79 (m, 3H), 5.96 (brs, 1H), 5.49-5.30 (m, 4H), 4.14-3.92 (m, 2H), 3.78-3.73 (m, 2H), 3.55-3.53 (m, 2H), 2.98-2.94 (m, 1H), 2.31-1.99 (m, 1H). m/z=421[M+1]$^+$.

Example 50 2-amino-5-((2R,4S)-2-(2,5-difluorophenyl)-4-fluoropyrrolidin-1-yl)-N-(2-hydroxyethoxy) pyrazolo[1,5-a]pyrimidine-3-carboxamide

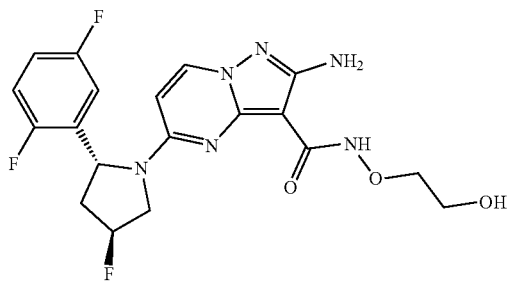 [SMILES: Nc1nn2ccc(N3C[C@@H](F)C[C@@H]3c3cc(F)ccc3F)nc2c1C(=O)NOCCO]

Referring to Example 3, (R)-2-amino-5-(2-(2,5-difluorophenyl)pyrrolidin-1-yl)pyrazolo[1,5-a]pyrimidine-3-carboxylic acid and methylamine hydrochloride were replaced with 2-amino-5-((2R,4S)-2-(2,5-difluorophenyl)-4-fluoropyrrolidin-1-yl)pyrazolo[1,5-a]pyrimidine-3-carboxylic acid and 1-[2-(aminooxy)ethoxy]ethylene, respectively, and the mixture was washed with 1 N hydrochloric acid during extraction, and finally separated by thin layer chromatography to afford the title compound.

$^1$H NMR (400 MHz, CDCl$_3$) δ 9.23 (brs, 1H), 8.04 (s, 1H), 7.18-6.78 (m, 3H), 6.00 (brs, 1H), 5.50-5.11 (m, 4H), 4.10-4.00 (m, 4H), 3.88-3.71 (m, 2H), 2.98-2.96 (m, 1H), 2.22-2.01 (m, 1H). m/z=437[M+1]$^+$.

Example 51 2-amino-N-cyclopropyl-5-((2R,4S)-2-(2,5-difluorophenyl)-4-fluoropyrrolidin-1-yl)pyrazolo[1,5-a]pyrimidine-3-carboxamide

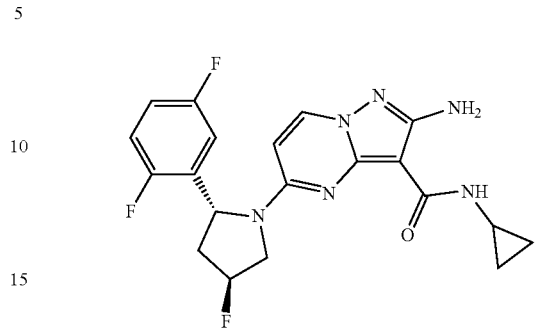

Referring to Example 3, (R)-2-amino-5-(2-(2,5-difluorophenyl)pyrrolidin-1-yl)pyrazolo[1,5-a]pyrimidine-3-carboxylic acid was replaced with 2-amino-5-((2R,4S)-2-(2,5-difluorophenyl)-4-fluoropyrrolidin-1-yl)pyrazolo[1,5-a]pyrimidine-3-carboxylic acid, and methylamine hydrochloride was replaced with cyclopropylamine to afford the title compound.

$^1$H NMR (400 MHz, CDCl$_3$) δ 8.03 (d, J=5.2 Hz, 1H), 7.65-7.19 (m, 1H), 7.18-7.06 (m, 1H), 7.05-6.92 (m, 1H), 6.83-6.79 (m, 1H), 5.92 (brs, 1H), 5.53-5.35 (m, 4H), 4.25 (brs, 1H), 4.06-3.94 (m, 1H), 3.06-2.96 (m, 1H), 2.76 (brs, 1H), 2.26-2.10 (m, 1H), 0.88-0.82 (m, 2H), 0.56-0.54 (m, 2H). m/z=417[M+1]$^+$.

Example 52 2-amino-5-((2R,4S)-2-(2,5-difluorophenyl)-4-fluoropyrrolidin-1-yl)-N-(1-(hydroxymethyl)cyclopropyl)pyrazolo[1,5-a]pyrimidine-3-carboxamide

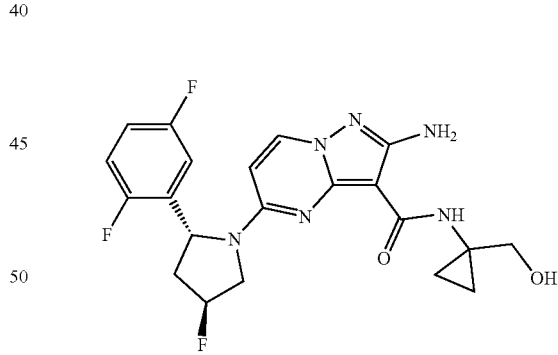

Referring to Example 3, (R)-2-amino-5-(2-(2,5-difluorophenyl)pyrrolidin-1-yl)pyrazolo[1,5-a]pyrimidine-3-carboxylic acid was replaced with 2-amino-5-((2R,4S)-2-(2,5-difluorophenyl)-4-fluoropyrrolidin-1-yl)pyrazolo[1,5-c]pyrimidine-3-carboxylic acid, and methylamine hydrochloride was replaced with 1-aminocyclopropanemethanol hydrochloride to afford the title compound.

$^1$H NMR (400 MHz, CDCl$_3$) δ 8.04 (brs, 1H), 7.95-7.31 (m, 1H), 7.10-7.04 (m, 1H), 6.99-6.94 (m, 1H), 6.88-6.84 (m, 1H), 6.23-5.62 (m, 1H), 5.48-5.35 (m, 4H), 5.09-4.47 (m, 1H), 4.42-4.15 (m, 1H), 4.07-3.95 (m, 1H), 3.82-3.25 (m, 2H), 3.06-2.96 (m, 1H), 2.22-2.12 (m, 1H), 1.06-0.83 (m, 4H). m/z=447[M+1]$^+$.

Bioactivity Assays

1. Assay for Inhibitory Activity ($IC_{50}$) Against NTRK Kinase

A testing platform for TrkA, TrkB and TrkC kinase activity was established based on Homogeneous Time-Resolved Fluorescence (HTRF) assay, and the activities of the compounds were tested using the platform. The compounds were subjected to three-fold gradient dilution with 100% DMSO with a starting concentration of 1 mM (11 concentrations in total). 4 μL of diluted sample for each concentration was added to 96 μL of reaction buffer (50 mM HEPES, pH7.4, 5 mM $MgCl_2$, 1 mM $NaVO_3$, 0.001% Tween-20, 0.01% BSA and 1 mM DTT) and mixed homogeneously to be used as a 4* compound. The reaction buffer was used to formulate 2* TrkA, TrkB and TrkC kinases (purchased from Carna Biosciences 08-186, 08-187, 08-197, and the final concentrations thereof were 0.5 nM, 0.1 nM, and 1 nM, respectively) and 4* substrate mixture (ATP+TK peptide) (wherein the final concentrations of ATP were 40 μM, 50 μM, and 20 μM, respectively; TK peptide, HTRF® KinEASE™-TK, was purchased from Cisbio, and the final concentration thereof was 100 nM) for use. 2.5 μL of the 4* compound was added to a 384-well plate (OptiPlate-384, purchased from PerkinElmer), and then 5 μL of the 2* TrkA, TrkB and TrkC kinases were added, and mixed homogeneously by centrifugation. Then 2.5 μL of the 4* substrate mixture was added to initiate the reaction (the total reaction volume is 10 μL). The 384-well plate was placed in an incubator and incubated for 60 min at 23° C. Then the reaction was terminated by adding 5 μL of Eu3+ cryptate-labeled anti-phosphotyrosine antibody (HTRF® KinEASE™-TK, purchased from Cisbio), and 5 μL of Streptavidin-XL-665 (HTRF® KinEASE™-TK, purchased from Cisbio). After incubated for 1 hr in the incubator, the fluorescence values were read on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 11 concentrations, and $IC_{50}$ values of the compounds were obtained by calculating the data using GraFit6.0 software (Erithacus Software).

2. Assay for Inhibitory Activity ($IC_{50}$) Against JAK2 Kinase

A testing platform for JAK2 kinase activity was established based on Homogeneous Time-Resolved Fluorescence (HTRF) assay, and the activities of the compounds were tested using the platform. The compounds were subjected to three-fold gradient dilution with 100% DMSO with a starting concentration of 1 mM (11 concentrations in total). 4 μL of diluted sample for each concentration was added to 96 μL of reaction buffer (50 mM HEPES, pH7.4, 10 mM $MgCl_2$, 1 mM EDTA, 0.01% Tween-20, 0.005% BSA and 2 mM DTT) and mixed homogeneously. 2.5 μL of the resulting liquid was then added to a 384-well plate (OptiPlate-384, purchased from PerkinElmer), and 5 μL of JAK2 kinase (purchased from Carna, and the final concentration thereof is 0.05 nM) was added, and mixed homogeneously by centrifugation. Then 2.5 μL of a mixture of ATP (the final concentration is 5 μM) and TK peptide (HTRF® KinEASE™-TK, purchased from Cisbio, and the final concentration is 100 nM) was added to initiate the reaction (the total reaction volume is 10 μL). The 384-well plate was placed in an incubator to incubate for 120 min at 23° C. Then the reaction was terminated by adding 5 μL of Eu3+ cryptate-labled anti-phosphotyrosine antibody (purchased from Cisbio), and 5 μL of Streptavidin-XL-665 (HTRF® KinEASE™-TK, purchased from Cisbio). After incubated for 1 hr in the incubator, the fluorescence values were read on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 11 concentrations, and $IC_{50}$ values of the compounds were obtained by calculating the data using GraFit6.0 software (Erithacus Software).

3. Assay for Inhibitory Activity ($IC_{50}$) Against $TrkA^{G667C}$ Kinase $TrkA^{G667C}$ (Kinase domain) kinase was expressed in Sf9 cells (purchased from Invitrogen) using pIEX-Bac-4 (purchased from Merck), and purified by using Ni column affinity chromatography on AKTA Purifier (GE company). A testing platform for $TrkA^{G667C}$ kinase activity was established based on Homogeneous Time-Resolved Fluorescence (HTRF) assay, and the activities of the compounds were tested using the platform. The compounds were subjected to five-fold gradient dilution with 100% DMSO with a starting concentration of 1 mM (8 concentrations in total). 4 μL of diluted sample for each concentration was added to 96 μL of reaction buffer (50 mM HEPES, pH7.4, 5 mM $MgCl_2$, 1 mM $NaVO_3$, 0.001% Tween-20, 0.01% BSA and 1 mM DTT) and mixed homogeneously to be used as a 4* compound. The reaction buffer was used to formulate 2* $TrkA^{G667C}$ kinases (the final concentration was 0.5 nM) and a 4* substrate mixture (ATP+TK peptide) (wherein, the final concentration of ATP was 15 μM; TK peptide, HTRF® KinEASE™-TK, was purchased from Cisbio, and the final concentration thereof was 100 nM) for use. 2.5 μL of the 4* compound was added to a 384-well plate (OptiPlate-384, purchased from PerkinElmer), and then 5 μL of the 2* $TrkA^{G667C}$ kinases were added, and mixed homogeneously by centrifugation. Then 2.5 μL of the 4* substrate mixture was added to initiate the reaction (the total reaction volume is 10 μL). The 384-well plate was placed in an incubator to incubate for 60 min at 23° C. Then the reaction was terminated by adding 5 μL of Eu3+ cryptate-labeled anti-phosphotyrosine antibody (HTRF KinEASE™-TK, purchased from Cisbio), and 5 μL of Streptavidin-XL-665 (HTRF® KinEASE™-TK, purchased from Cisbio). After incubated for 1 h in the incubator, the fluorescence values were read on Envision (purchased from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 8 concentrations, and $IC_{50}$ values of the compounds were obtained by calculating the data using GraFit6.0 software (Erithacus Software).

In the foregoing activity experiments, unless otherwise specified, the following terms have the following meanings:

"*" means multiplication, and indicates multiples.

"3-fold gradient dilution" means that 2 volumes of a diluent solution was added to 1 volume of a stock solution 1 to obtain a stock solution 2; and then 1 volume of the stock solution 2 was taken and thereto 2 volumes of the diluent solution was added to obtain a stock solution 3. Different concentrations of solutions were obtained in a similar manner.

"5-fold gradient dilution" means that 4 volumes of a diluent solution was added to 1 volume of a stock solution 1 to obtain a stock solution 2; and then 1 volume of the stock solution 2 was taken and thereto 4 volumes of the diluent solution was added to obtain a stock solution 3. Different concentrations of solutions were obtained in a similar manner.

The "final concentration" refers to a concentration in a whole reaction system at the time of initiating a reaction, and is a concentration based on a total reaction volume.

"%" means mass concentration fraction.

"Tween-20" refers to Tween 20.

"BSA" refers to bovine serum albumin.

"DTT" refers to dithiothreitol.

"EDTA" refers to ethylenediamine tetraacetic acid.

The compounds prepared in the above Examples were analyzed according to the biological methods described in the present application, and the results are as follows:

TABLE 1

Inhibitory activity ($IC_{50}$) of compounds against TrkA kinase

| Example No. | TrkA $IC_{50}$ (nM) |
|---|---|
| 1 | <1 |
| 2 | <100 |
| 3 | <1 |
| 4 | <1 |
| 5 | <1 |
| 6 | <1 |
| 7 | <100 |
| 9 | <25 |
| 10 | <25 |
| 11 | <1 |
| 12 | <1 |
| 13 | <1 |
| 14 | <1 |
| 15 | <25 |
| 16 | <1 |
| 17 | <1 |
| 18 | <1 |
| 19 | <1 |
| 20 | <1000 |
| 21 | <500 |
| 22 | <100 |
| 23 | <100 |
| 24 | <500 |
| 25 | <25 |
| 26 | <100 |
| 27 | <25 |
| 28 | <25 |
| 29 | <1 |
| 30 | <1 |
| 31 | <1 |
| 32 | <25 |
| 33 | <25 |
| 34 | <1 |
| 35 | <1 |
| 36 | <1 |
| 37 | <500 |
| 38 | <25 |
| 39 | <1 |
| 40 | <1 |
| 41 | <1 |
| 42 | <25 |
| 43 | <25 |
| 44 | <25 |
| 45 | <25 |
| 47 | <1000 |
| 48 | <500 |
| 49 | <1 |
| 50 | <1 |
| 51 | <1 |
| 52 | <1 |

TABLE 2

Inhibitory activity ($IC_{50}$) of compounds against TrkA/TrkB/TrkC/JAK2 kinase

| Example No. | TrkA $IC_{50}$ (nM) | TrkB $IC_{50}$ (nM) | TrkC $IC_{50}$ (nM) | JAK2 $IC_{50}$ (nM) |
|---|---|---|---|---|
| 4 | <1 | <10 | <10 | >2000 |
| 12 | <1 | <1 | <1 | >20 |
| 14 | <1 | <10 | <10 | >500 |
| 36 | <1 | <1 | <1 | >100 |
| 39 | <1 | <1 | <1 | >10 |

The compounds of the Examples exhibit excellent inhibitory activity against TrkA, TrkB and TrkC. Moreover, the compounds of the Examples have a highly selective inhibition against Trk as compared with JAK2.

TABLE 3

Inhibitory activity ($IC_{50}$) of compounds against mutant TrkA kinase

| Example No. | TrkA$^{G667C}$ $IC_{50}$ (nM) |
|---|---|
| 12 | <1 |
| 36 | <10 |
| 39 | <10 |

The compounds of the Examples also exhibit excellent inhibitory activity against the mutant TrkA.

Pharmacokinetic Assay

Male SD rats were available from Beijing Vital River Laboratory Animal Technology Co., Ltd. The rats were allocated with three rats per group, and separately administered the suspension of a sample to be tested (5 mg/kg) by single intragastric administration. Before the experiment, the animals were fasted overnight, and the fasting time was from 10 hrs before administration to 4 hrs after administration. After administration, a blood sample was taken at 0.25 hr, 0.5 hr, 1 hr, 2 hrs, 4 hrs, 6 hrs, 8 hrs and 24 hrs. After the animals were narcotized with isoflurane using an anaesthesia machine for small animals, 0.3 mL of whole blood was taken from fundus venous plexus, and placed in a heparin anticoagulant tube. At 4° C., the sample was centrifuged at 4000 rpm for 5 min, and plasma was transferred to a centrifuge tube and preserved at −80° C. until the analysis was started. The sample in plasma was extracted by the protein precipitation method, and the extracted liquid was analyzed by LC/MS/MS.

TABLE 3

PK of compounds in rats

| PK in Rat | Example 36 | Example 39 |
|---|---|---|
| Oral dose (mg/kg) | 5 | 5 |
| $T_{1/2}$(hr) | 3.09 | 1.46 |
| Tmax(hr) | 1.00 | 1.67 |
| Cmax(ng/mL) | 488 | 276 |
| $AUC_{INF\_obs}$(hr*ng/mL) | 2244 | 876 |

What is claimed is:

1. A compound of Formula I or a pharmaceutically acceptable salt thereof:

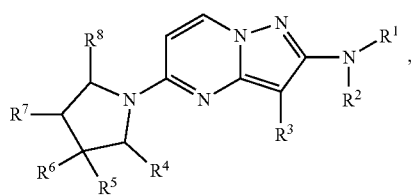

Formula I wherein:
R¹ is hydrogen;
R² is selected from the group consisting of hydrogen, $C_{1-10}$ alkyl, —C(=O)R⁹, —C(=O)NHR⁹ and —S(=O)₂R⁹, wherein the $C_{1-10}$ alkyl is optionally substituted by one or more substituents independently selected from the group consisting of halo, nitro, hydroxy, cyano, $C_{1-6}$ alkyl, $C_{1-6}$ alkoxy, optionally substituted 3- to 6-membered cycloalkyl, optionally substituted 3- to 6-membered aliphatic heterocyclyl, optionally substituted 6- to 10-membered aryl and an optionally substituted 5- to 10-membered aromatic heterocyclyl;
R³ is selected from the group consisting of hydrogen, halo, cyano, hydroxy, nitro, —C(=O)R¹⁰, —C(=O)NR¹⁰R¹¹, —C(=S)NR¹⁰R¹¹, 6- to 10-membered aryl and 5- to 10-membered aromatic heterocyclyl, wherein the 6- to 10-membered aryl and 5- to 10-membered aromatic heterocyclyl are each independently optionally substituted by one or more substituents independently selected from the group consisting of $C_{1-6}$ alkyl, $C_{1-6}$ alkoxycarbonyl, optionally substituted pyrrolidinyl, optionally substituted morpholinyl and optionally substituted pyrrolidinylcarbonyl;
R⁴ and R⁷ are independently selected from the group consisting of hydrogen;
R⁵ and R⁶ are independently selected from the group consisting of hydrogen, halo, nitro, hydroxy, amino and cyano, or R⁵ and R⁶ together form oxo;
R⁸ is selected from the group consisting of phenyl, pyridyl, pyridonyl and pyrazinyl, wherein the phenyl, pyridyl, pyridonyl and pyrazinyl are each independently optionally substituted by one or more substituents independently selected from the group consisting of halo, nitro, hydroxy, cyano, $C_{1-4}$ alkyl and $C_{1-4}$ alkoxy;
R⁹ is selected from the group consisting of $C_{1-10}$ alkyl and phenyl, wherein the $C_{1-10}$ alkyl and phenyl are each independently optionally substituted by one or more substituents independently selected from the group consisting of halo, nitro, hydroxy, cyano, $C_{1-6}$ alkyl and $C_{1-6}$ alkoxy;
R¹⁰ and R¹¹ are independently selected from the group consisting of hydrogen, hydroxy, $C_{1-6}$ alkyl, $C_{1-6}$ alkoxy, 3- to 6-membered cycloalkyl and 6- to 10-membered aryl, wherein the $C_{1-6}$ alkyl, $C_{1-6}$ alkoxy, 3- to 6-membered cycloalkyl and 6- to 10-membered aryl are each independently optionally substituted by one or more substituents independently selected from the group consisting of halo, hydroxy, nitro, cyano, $C_{1-4}$ alkyl, and hydroxy($C_{1-6}$ alkyl), 2,2-dimethyl-1,3-dioxolan-4-yl and N,N-di($C_{1-4}$ alkyl) amino;
or
R¹⁰ and R¹¹ taken together with the N to which they are attached form a 5- to 10-membered alicyclic heterocyclyl, wherein the 5- to 10-membered alicyclic heterocyclyl is optionally substituted by one or more substituents independently selected from the group consisting of halo, hydroxy, nitro and cyano.

2. The compound according to claim 1, wherein:
R¹ is hydrogen;
R² is selected from the group consisting of hydrogen, $C_{1-6}$ alkyl, —C(=O)R⁹, —C(=O)NHR⁹ and —S(=O)₂R⁹, wherein the $C_{1-6}$ alkyl is optionally substituted by one or more substituents independently selected from the group consisting of halo, nitro, hydroxy, cyano, $C_{1-4}$ alkyl, $C_{1-4}$ alkoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholinyl, thiomorpholinyl, tetrahydrothiophenyl, phenyl, 4-methylphenyl, 4-methoxyphenyl, furyl, pyrrolyl and pyrazinyl;
R³ is selected from the group consisting of hydrogen, halo, cyano, hydroxy, nitro, —C(=O)R¹⁰, —C(=O)NR¹⁰R¹¹, —C(=S)NR¹⁰R¹¹, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of $C_{1-4}$ alkyl, $C_{1-4}$ alkoxycarbonyl, pyrrolidin-1-yl, 3-hydroxypyrrolidin-1-yl, morpholin-4-yl and 3-hydroxypyrrolidin-1-ylcarbonyl;
R⁴ and R⁷ are independently selected from the group consisting of hydrogen;
R⁵ and R⁶ are independently selected from the group consisting of hydrogen, fluoro, chloro, bromo, iodo, nitro, hydroxy, amino and cyano, or R⁵ and R⁶ together form oxo;
R⁸ is selected from the group consisting of phenyl, pyridyl, pyridonyl and pyrazinyl, wherein the phenyl, pyridyl, pyridonyl and pyrazinyl are each independently optionally substituted by one or more substituents independently selected from the group consisting of halo, nitro, hydroxy, cyano, $C_{1-4}$ alkyl and $C_{1-4}$ alkoxy;
R⁹ is selected from the group consisting of $C_{1-6}$ alkyl and phenyl, wherein the $C_{1-6}$ alkyl and phenyl are each independently optionally substituted by one or more substituents independently selected from the group consisting of halo, nitro, hydroxy, cyano, $C_{1-4}$ alkyl and $C_{1-4}$ alkoxy;
R¹⁰ and R¹¹ are independently selected from the group consisting of hydrogen, hydroxy, methyl, ethyl, n-propyl, isopropyl, methoxy, ethoxy, n-propoxy, cyclopropyl, cyclobutyl, cyclopentyl, cyclohexyl and phenyl, wherein the methyl, ethyl, n-propyl, isopropyl, methoxy, ethoxy, n-propoxy, cyclopropyl, cyclobutyl, cyclopentyl, cyclohexyl and phenyl are each independently optionally substituted by one or more substituents independently selected from the group consisting of halo, hydroxy, nitro, cyano, methyl, ethyl, n-propyl, isopropyl, hydroxymethyl, 2-hydroxyethyl, 3-hydroxy-n-propyl, 2,2-dimethyl-1,3-dioxolan-4-yl, N,N-dimethylamino and N,N-diethylamino;
or
R¹⁰ and R¹¹ taken together with the N to which they are attached form pyrrolidin-1-yl, wherein the pyrrolidin-1-yl is optionally substituted by one or more substituents independently selected from the group consisting of halo and hydroxy.

3. The compound according to claim 2, wherein:

$R^1$ is hydrogen;

$R^2$ is selected from the group consisting of hydrogen, methyl, ethyl, n-propyl, isopropyl, —C(=O)$R^9$, —C(=O)NH$R^9$ and —S(=O)$_2R^9$, wherein the methyl, ethyl, n-propyl and isopropyl are each independently optionally substituted by one or more substituents independently selected from the group consisting of fluoro, chloro, bromo, iodo, nitro, hydroxy, cyano, methyl, ethyl, methoxy, ethoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholin-4-yl, thiomorpholin-4-yl, tetrahydrothiophenyl, phenyl, 4-methylphenyl, 4-methoxyphenyl, furanyl, pyrrolyl and pyrazinyl;

$R^3$ is selected from the group consisting of hydrogen, fluoro, chloro, bromo, iodo, cyano, hydroxy, nitro, —C(=O)$R^{10}$, —C(=O)N$R^{10}R^{11}$, —C(=S)NH$_2$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of methyl, ethyl, n-propyl, isopropyl, methoxycarbonyl, ethoxycarbonyl, pyrrolidin-1-yl, 3-hydroxypyrrolidin-1-yl, morpholin-4-yl and 3-hydroxypyrrolidin-1-ylcarbonyl;

$R^4$ and $R^7$ are independently selected from the group consisting of hydrogen;

$R^5$ and $R^6$ are independently selected from hydrogen, fluoro, chloro, bromo, iodo, and hydroxy, or $R^5$ and $R^6$ together form oxo;

$R^8$ is selected from the group consisting of phenyl, pyridyl, pyridonyl and pyrazinyl, wherein the phenyl, pyridyl, pyridonyl and pyrazinyl are each independently optionally substituted by one or more substituents independently selected from the group consisting of fluoro, chloro, bromo, iodo, hydroxy, methoxy and ethoxy;

$R^9$ is selected from the group consisting of methyl, ethyl, n-propyl, isopropyl and phenyl, wherein the methyl, ethyl, n-propyl, isopropyl and phenyl are each independently optionally substituted by one or more substituents independently selected from the group consisting of fluoro, chloro, bromo, iodo, methyl, ethyl, methoxy and ethoxy;

$R^{10}$ and $R^{11}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, chloro, bromo, iodo, hydroxy, methyl, ethyl, hydroxymethyl, 2-hydroxyethyl, 2,2-dimethyl-1,3-dioxolan-4-yl, N,N-dimethylamino and N,N-diethylamino;

or $R^{10}$ and $R^{11}$ taken together with the N to which they are attached form pyrrolidin-1-yl, wherein the pyrrolidin-1-yl is optionally substituted by one or more substituents independently selected from the group consisting of fluoro, chloro, bromo, iodo, and hydroxy.

4. The compound according to claim 1, wherein the compound of Formula I has a structure represented by Formula II:

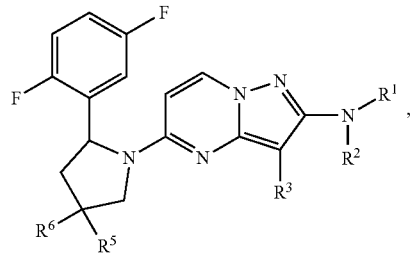

Formula II wherein $R^1$, $R^2$, $R^3$, $R^5$ and $R^6$ are as defined in claim 1.

5. The compound according to claim 4, wherein the compound of Formula II has a structure represented by Formula III:

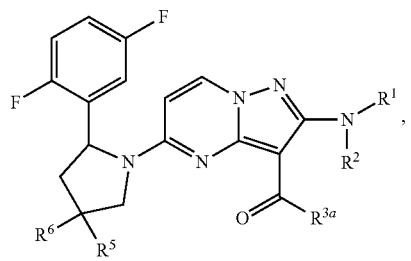

Formula III wherein:

$R^1$, $R^2$, $R^5$ and $R^6$ are as defined in claim 4;

$R^{3a}$ is selected from the group consisting of $R^{7a}$ and N$R^{7a}R^{8a}$;

$R^{7a}$ and $R^{8a}$ are independently selected from the group consisting of hydrogen, hydroxy, $C_{1-6}$ alkyl, $C_{1-6}$ alkoxy, 3- to 6-membered cycloalkyl and 6- to 10-membered aryl, wherein the $C_{1-6}$ alkyl, $C_{1-6}$ alkoxy, 3- to 6-membered cycloalkyl and 6- to 10-membered aryl are each independently optionally substituted by one or more substituents independently selected from the group consisting of halo, hydroxy, nitro, cyano, $C_{1-4}$ alkyl, $C_{1-6}$ alkyl substituted by hydroxy, 2,2-dimethyl-1,3-dioxolan-4-yl and —N($C_{1-4}$ alkyl)$_2$;

or $R^{7a}$ and $R^{8a}$ taken together with the N to which they are attached form a 5- to 10-membered aliphatic heterocyclyl, wherein the 5- to 10-membered aliphatic heterocyclyl is optionally substituted by one or more substituents independently selected from the group consisting of halo, hydroxy, nitro and cyano.

6. The compound according to claim 5, wherein:

$R^{7a}$ and $R^{8a}$ are independently selected from the group consisting of hydrogen, hydroxy, methyl, ethyl, n-propyl, isopropyl, methoxy, ethoxy, n-propoxy, cyclopropyl, cyclobutyl, cyclopentyl, cyclohexyl and phenyl, wherein the methyl, ethyl, n-propyl, isopropyl, methoxy, ethoxy, n-propoxy, cyclopropyl, cyclobutyl, cyclopentyl, cyclohexyl and phenyl are each independently optionally substituted by one or more substituents independently selected from the group consisting of halo, hydroxy, nitro, cyano, methyl, ethyl, n-propyl, isopropyl, hydroxymethyl, 2-hydroxyethyl, 3-hydroxyn-propyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more substituents independently selected from the group consisting of halo and hydroxy.

7. The compound according to claim 6, wherein:

$R^{7a}$ and $R^{8a}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, chloro, bromo, iodo, hydroxy, methyl, ethyl, hydroxymethyl, 2-hydroxyethyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more substituents independently selected from the group consisting of fluoro, chloro, bromo, iodo, and hydroxy.

8. The compound according to claim 7, wherein:

$R^1$ is hydrogen;

$R^2$ is selected from the group consisting of hydrogen, methyl, ethyl, —C(=O)$R^{6a}$, —C(=O)NH$R^{6a}$ and —S(=O)$_2R^{6a}$, wherein the methyl and ethyl are each independently optionally substituted by one or more substituents independently selected from the group consisting of pyrrolidin-1-yl, piperidin-1-yl, piperidin-4-yl, morpholin-4-yl, thiomorpholin-4-yl, phenyl, 4-methylphenyl and 4-methoxyphenyl;

$R^{3a}$ is selected from the group consisting of $R^{7a}$ and $NR^{7a}R^{8a}$;

$R^5$ and $R^6$ are independently selected from the group consisting of hydrogen, fluoro and hydroxy;

or $R^5$ and $R^6$ together form oxo;

$R^{6a}$ is selected from the group consisting of methyl, ethyl and 4-methylphenyl;

$R^{7a}$ and $R^{8a}$ are independently selected from the group consisting of hydrogen, hydroxy, methyl, ethyl, methoxy, ethoxy, cyclopropyl, cyclohexyl and phenyl, wherein the methyl, ethyl, methoxy, ethoxy, cyclopropyl, cyclohexyl and phenyl are each independently optionally substituted by one or more substituents independently selected from the group consisting of fluoro, hydroxy, methyl, hydroxymethyl, 2,2-dimethyl-1,3-dioxolan-4-yl, N,N-dimethylamino and N,N-diethylamino;

or $R^{7a}$ and $R^{8a}$ taken together with the N to which they are attached form pyrrolidin-1-yl, wherein the pyrrolidin-1-yl is optionally substituted by one or more hydroxy.

9. The compound according to claim 5, wherein the compound of Formula III has a structure represented by Formula IIIa:

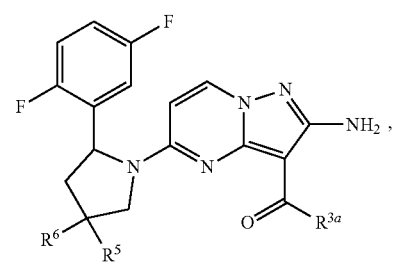

Formula IIIa wherein $R^{3a}$, $R^5$ and $R^6$ are as defined in claim 5.

10. The compound according to claim 1, wherein the compound of Formula I has a structure represented by Formula IV:

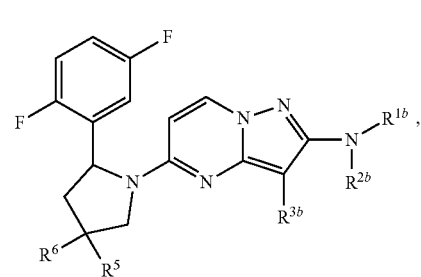

Formula IV wherein:

$R^5$ and $R^6$ are as defined in claim 1;

$R^{1b}$ is hydrogen;

$R^{2b}$ is selected from the group consisting of hydrogen and $C_{1-10}$ alkyl, wherein the $C_{1-10}$ alkyl is optionally substituted by one or more substituents independently selected from the group consisting of halo, nitro, hydroxy, cyano, $C_{1-6}$ alkyl, $C_{1-6}$ alkoxy, optionally substituted 3- to 6-membered cycloalkyl, optionally substituted 3- to 6-membered aliphatic heterocyclyl, optionally substituted 6- to 10-membered aryl and optionally substituted 5- to 10-membered aromatic heterocyclyl;

$R^{3b}$ is selected from the group consisting of hydrogen, halo, cyano, hydroxy, nitro, —C(=S)NH$_2$, 6- to 10-membered aryl and 5- to 10-membered aromatic heterocyclyl, wherein the 6- to 10-membered aryl and 5- to 10-membered aromatic heterocyclyl are each independently optionally substituted by one or more substituents independently selected from the group consisting of $C_{1-6}$ alkyl, $C_{1-6}$ alkoxycarbonyl, optionally substituted pyrrolidinyl, optionally substituted morpholinyl and optionally substituted pyrrolidinylcarbonyl.

11. The compound according to claim 10, wherein $R^{1b}$ is hydrogen;

$R^{2b}$ is selected from the group consisting of hydrogen and $C_{1-6}$ alkyl, wherein the $C_{1-6}$ alkyl is optionally substituted by one or more substituents independently selected from the group consisting of halo, nitro, hydroxy, cyano, $C_{1-4}$ alkyl, $C_{1-4}$ alkoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholinyl, thiomorpholinyl, tetrahydrothiophenyl, phenyl, 4-methylphenyl, 4-methoxyphenyl, furyl, pyrrolyl and pyrazinyl;

$R^{3b}$ is selected from the group consisting of hydrogen, halo, cyano, hydroxy, nitro, —C(=S)NH$_2$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of C$_{1-4}$ alkyl, C$_{1-4}$ alkoxycarbonyl, pyrrolidin-1-yl, 3-hydroxypyrrolidin-1-yl, morpholin-4-yl and 3-hydroxypyrrolidin-1-ylcarbonyl.

12. The compound according to claim 10, wherein:
$R^{1b}$ is hydrogen;
$R^{2b}$ is selected from the group consisting of hydrogen, methyl and ethyl, wherein the methyl and ethyl are each independently optionally substituted by phenyl, 4-methylphenyl or 4-methoxyphenyl;
$R^{3b}$ is selected from the group consisting of hydrogen fluoro, chloro, bromo, iodo, cyano, —C(=S)NH$_2$, phenyl,

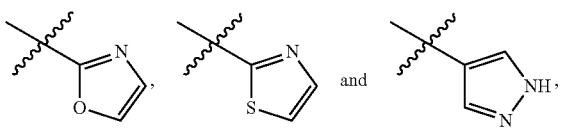 [SMILES: *c1ncco1 ; *c1nccs1 ; *c1cn[nH]c1]

wherein the phenyl,

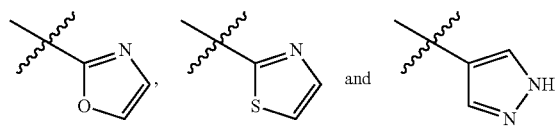 [SMILES: *c1ncco1 ; *c1nccs1 ; *c1cn[nH]c1]

are each independently optionally substituted by one or more substituents independently selected from the group consisting of methyl, ethyl, methoxycarbonyl, ethoxycarbonyl, pyrrolidin-1-yl, morpholin-4-yl and 3-hydroxypyrrolidin-1-ylcarbonyl.

13. A method for treating a disease mediated by Trk tyrosine kinase receptor in a mammal, comprising administering to the mammal in need thereof a therapeutically effective amount of the compound according to claim 1 or a pharmaceutically acceptable salt thereof, wherein the disease is a tumor.

14. The compound according to claim 1, wherein:
$R^2$ is selected from the group consisting of hydrogen, C$_{1-6}$ alkyl, —C(=O)R$^9$, —C(=O)NHR$^9$ and —S(=O)$_2$R$^9$, wherein the C$_{1-6}$ alkyl is optionally substituted by one or more substituents independently selected from the group consisting of halo, nitro, hydroxy, cyano, C$_{1-4}$ alkyl, C$_{1-4}$ alkoxy, cyclopropyl, cyclobutyl, cyclopentyl, cyclohexyl, tetrahydrofuranyl, dihydrofuranyl, pyrrolidinyl, N-methylpyrrolidinyl, pyrazolidinyl, piperidinyl, piperazinyl, morpholinyl, thiomorpholinyl, tetrahydrothiophenyl, phenyl, 4-methylphenyl, 4-methoxyphenyl, furyl, pyrrolyl and pyrazinyl.

15. The compound according to claim 1, wherein:
$R^3$ is selected from the group consisting of hydrogen, halo, cyano, hydroxy, nitro, —C(=O)R$^{10}$, —C(=O)NR$^{10}$R$^{11}$, —C(=S)NR$^{10}$R$^{11}$, phenyl, oxazolyl, isoxazolyl, thiazolyl and pyrazolyl, wherein the phenyl, oxazolyl, isoxazolyl, thiazolyl and pyrazolyl are each independently optionally substituted by one or more substituents independently selected from the group consisting of C$_{1-4}$ alkyl, C$_{1-4}$ alkoxycarbonyl, pyrrolidin-1-yl, 3-hydroxypyrrolidin-1-yl, morpholin-4-yl and 3-hydroxypyrrolidin-1-ylcarbonyl.

16. The compound according to claim 3, wherein $R^8$ is phenyl substituted by one or more fluoro.

17. The compound according to claim 16, wherein $R^8$ is 2,5-difluorophenyl.

18. The compound according to claim 1, wherein the compound or a pharmaceutically acceptable salt thereof is selected from:

1

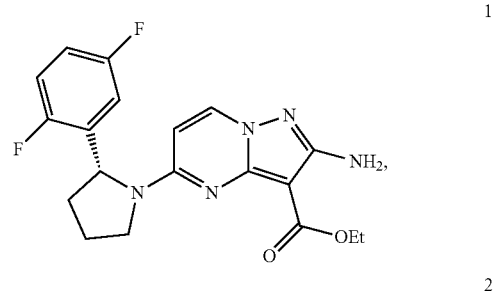

2

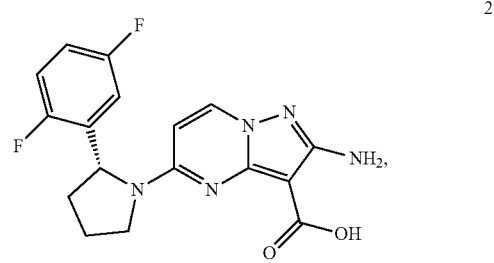

3

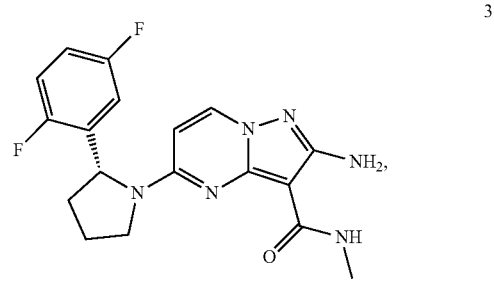

4

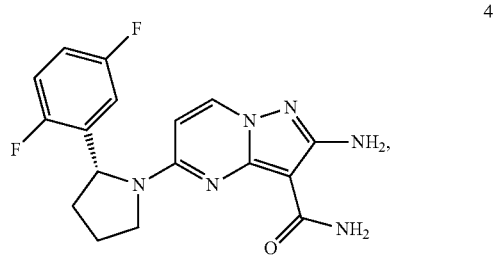

5

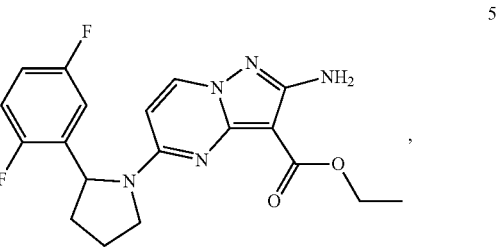

103
6 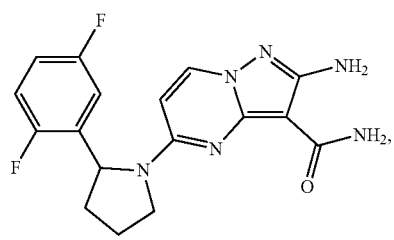
7 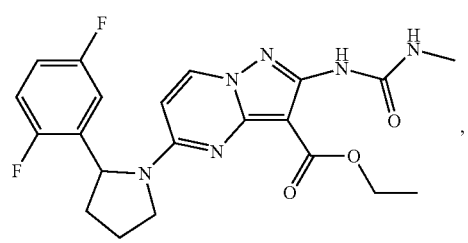
8 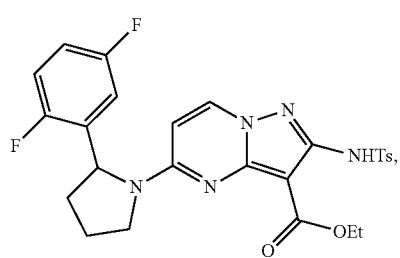
9 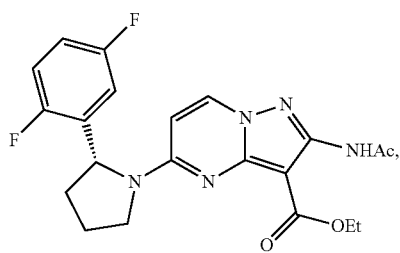
10 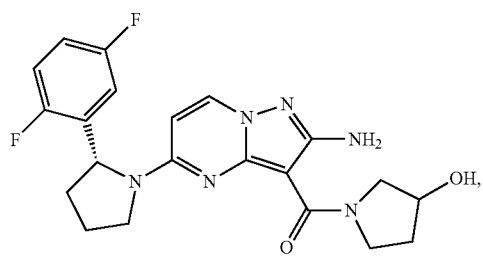
11 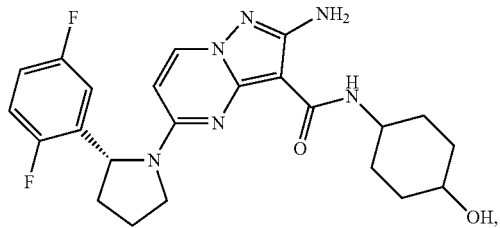
104
12 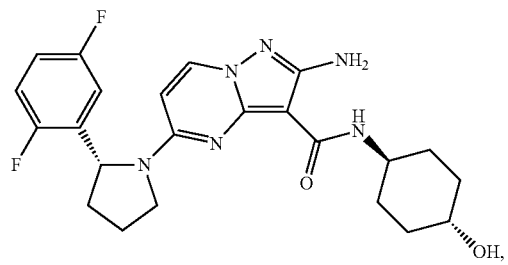
13 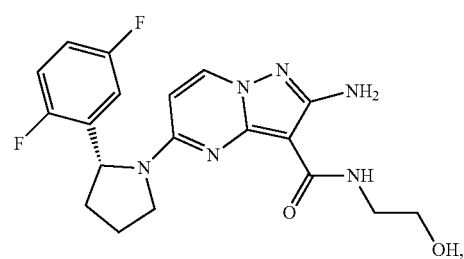
14 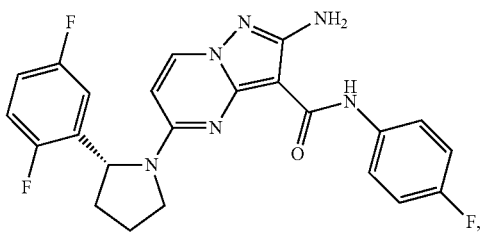
15 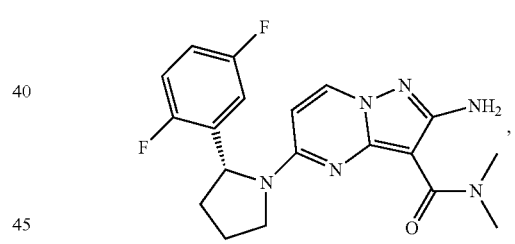
16 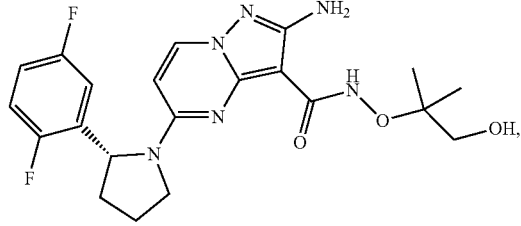
17 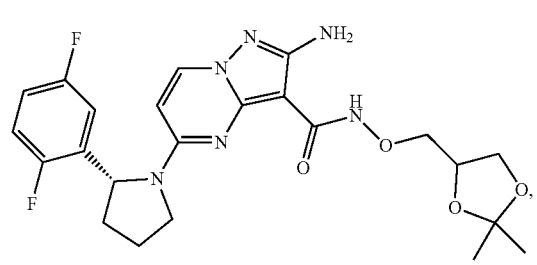

18
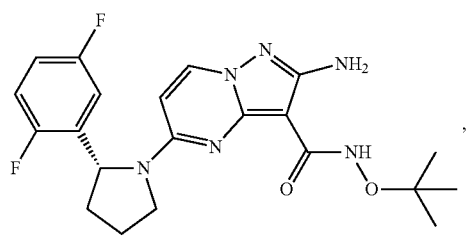
19
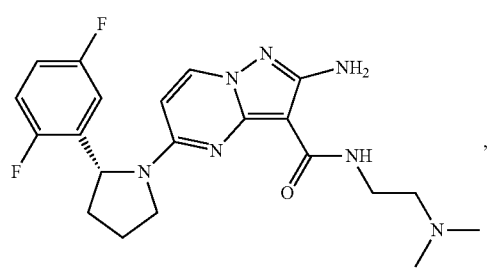
20
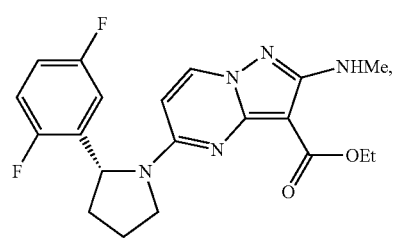
21
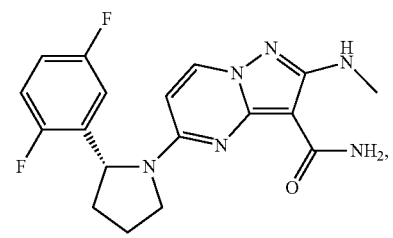
22
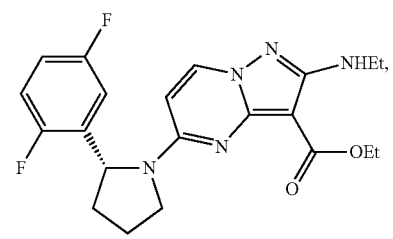
23
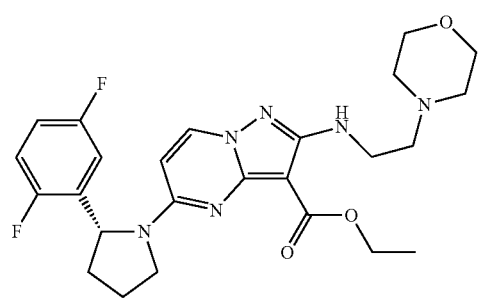
24
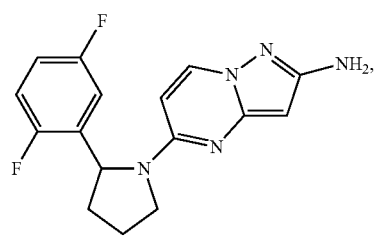
25
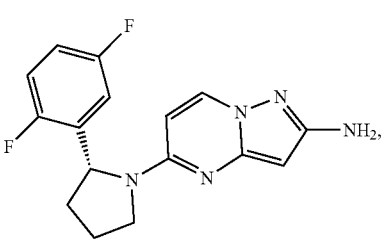
26
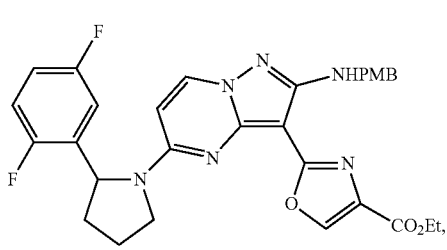
27
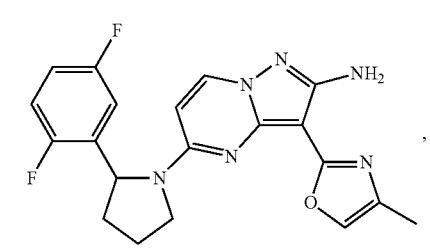
28
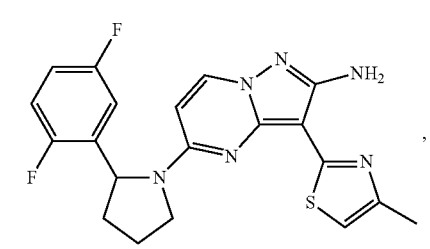
29
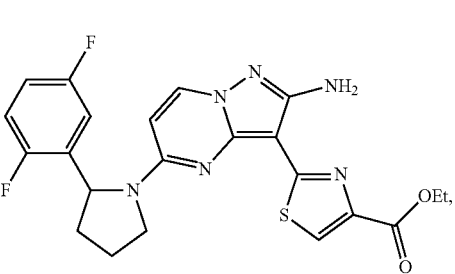

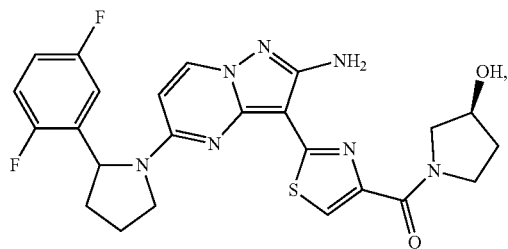
30
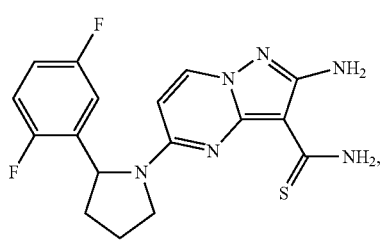
31
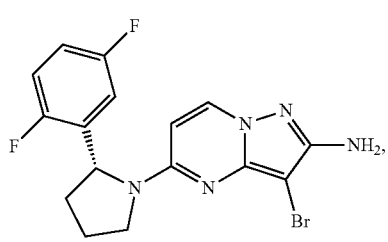
32
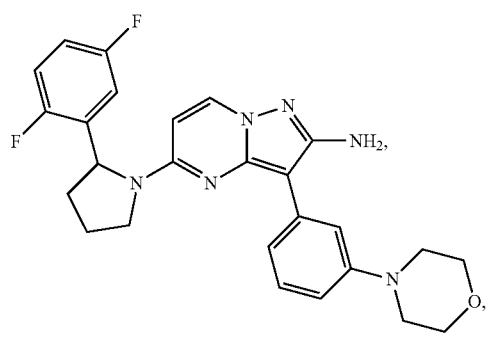
33
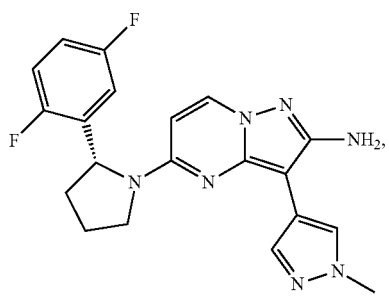
34
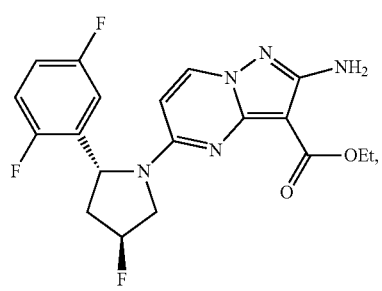
35
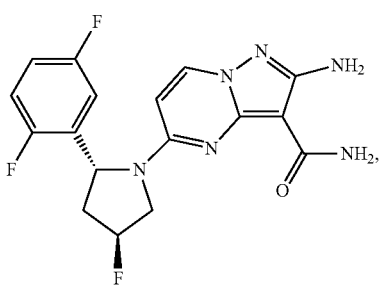
36
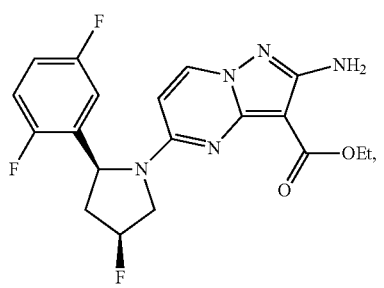
37
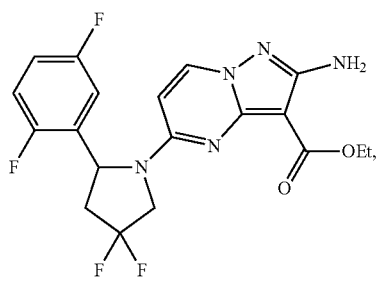
38
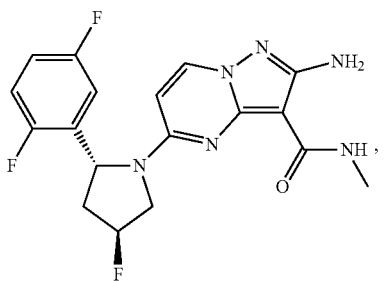
39
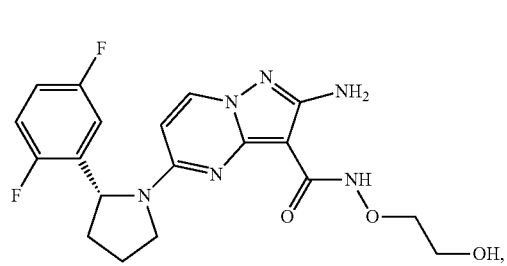
40

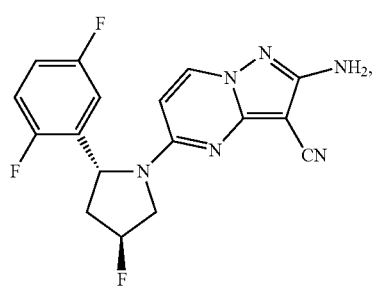
41
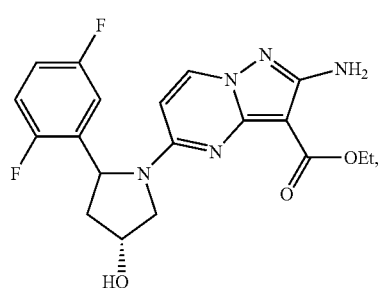
42
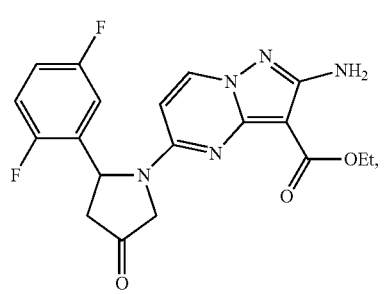
43
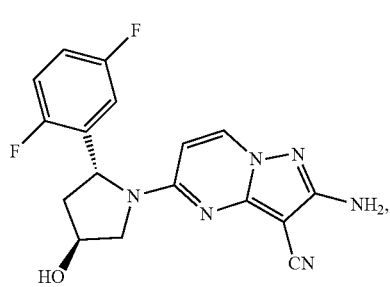
44
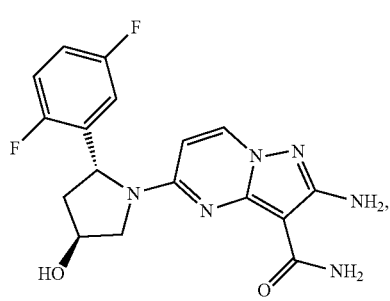
45
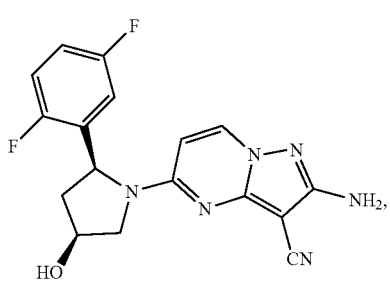
46
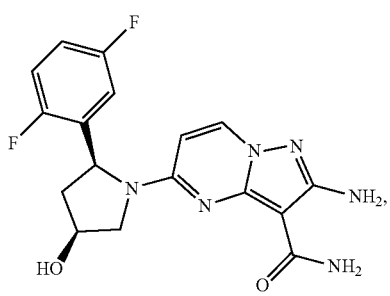
47
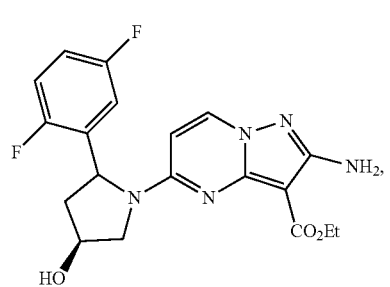
48
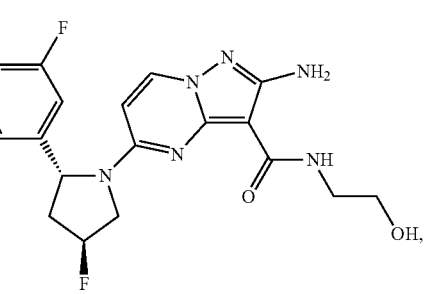
49
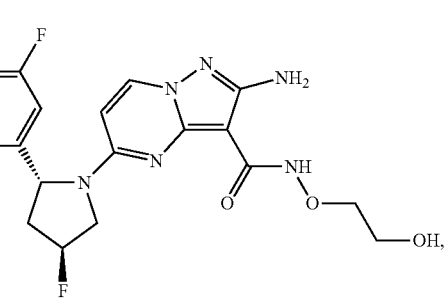
50

51
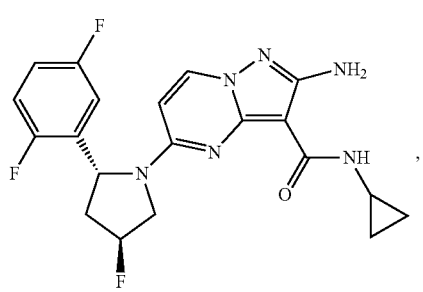
52
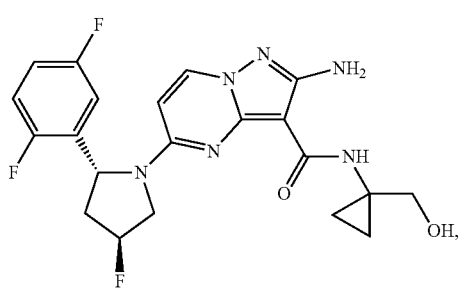
or a pharmaceutically acceptable salt thereof.
19. A pharmaceutical composition comprising the compound according to claim 1 or a pharmaceutically acceptable salt thereof.
20. The method according to claim 13, wherein the disease is a solid tumor.
* * * * *